United States Patent
Olsen et al.

(10) Patent No.: US 11,066,557 B2
(45) Date of Patent: Jul. 20, 2021

(54) PROTEIN-SURFACTANT-MONOMER/POLYMER BLENDS AND COPOLYMERS FOR PROTEIN-BASED PLASTICS

(71) Applicant: Massachusetts Institute of Technology, Cambridge, MA (US)

(72) Inventors: Bradley David Olsen, Arlington, MA (US); Wui Yarn Chan, Cambridge, MA (US)

(73) Assignee: Massachusetts Institute of Technology, Cambridge, MA (US)

(*) Notice: Subject to any disclaimer, the term of this patent is extended or adjusted under 35 U.S.C. 154(b) by 181 days.

(21) Appl. No.: 16/106,561

(22) Filed: Aug. 21, 2018

(65) Prior Publication Data
US 2019/0062556 A1 Feb. 28, 2019

Related U.S. Application Data

(60) Provisional application No. 62/548,531, filed on Aug. 22, 2017.

(51) Int. Cl.
| | |
|---|---|
| *C08L 89/00* | (2006.01) |
| *C08L 33/08* | (2006.01) |
| *C08L 33/14* | (2006.01) |
| *C08K 5/3445* | (2006.01) |
| *C08K 5/09* | (2006.01) |
| *C07K 14/76* | (2006.01) |
| *C07K 14/46* | (2006.01) |
| *C07K 14/78* | (2006.01) |

(Continued)

(52) U.S. Cl.
CPC ............ *C08L 89/00* (2013.01); *C07K 14/461* (2013.01); *C07K 14/4717* (2013.01); *C07K 14/76* (2013.01); *C07K 14/78* (2013.01); *C08H 1/00* (2013.01); *C08K 5/09* (2013.01); *C08K 5/3445* (2013.01); *C08L 33/08* (2013.01); *C08L 33/14* (2013.01); *C08L 33/26* (2013.01); *C07K 16/00* (2013.01)

(58) Field of Classification Search
CPC .......... C08L 89/00; C08L 33/08; C08L 33/14; C07K 14/76; C08K 5/3445; C08K 5/09
See application file for complete search history.

(56) References Cited

U.S. PATENT DOCUMENTS

2017/0009184 A1* 1/2017 Schubert ............. C11D 17/047

OTHER PUBLICATIONS

Fairley et al., "Mechanical Properties and Water Vapor Permeability of Edible Films from Whey Protein Isolate and Sodium Dodecyl Sulfate," J. Agric. Food Chem., 44:438-443 (1996).

(Continued)

*Primary Examiner* — Robert D Harlan
(74) *Attorney, Agent, or Firm* — Foley Hoag LLP; Dana M. Gordon; Lawrence P. Tardibono

(57) ABSTRACT

Disclosed are copolymers comprising a modified protein first monomer, a surfactant, and a second monomer. Methods of making copolymers comprising a modified protein first monomer, a surfactant, and a second monomer are described. Also disclosed are articles comprising the copolymers. Disclosed are blends comprising a protein, a surfactant, and a second monomer. Methods of making blends comprising a protein, a surfactant, and a second monomer are described. Also disclosed are articles comprising the blends.

15 Claims, 32 Drawing Sheets

(51) Int. Cl.
  *C08H 1/00*   (2006.01)
  *C07K 14/47*  (2006.01)
  *C08L 33/26*  (2006.01)
  *C07K 16/00*  (2006.01)

(56) References Cited

OTHER PUBLICATIONS

Farrugia et al., "Multi-enzyme cascade reactions using protein—polymer surfactant self-standing films," Chem Commun., 53:2094-2097 (2017).
Gao et al., "In situ growth of a stoichiometric PEG-like conjugate at a protein's N-terminus with significantly improved pharmacokinetics," PNAS, 106(36):15231-15236 (2009).
Huang et al., "Highly Active Biocatalytic Coatings from Protein-Polymer Diblock Copolymers," ACS Appl. Mater. Interfaces, 7:14660-14669 (2015).
Liu et al., "Liquefaction of Biopolymers: Solvent-free Liquids and Liquid Crystals from Nucleic Acids and Proteins," Accounts of Chemical Research, 50:1212-1221 (2017).
Liu et al., "Thermotropic liquid crystals from biomacromolecules," PNAS, 111(52):18596-18600 (2014).
Schmidt et al., "Thermal stability of films formed by soy protein isolate-sodium dodecyl sulfate," Polymer Degradation and Stability 87:25-31 (2005).
Stenzel, "Bioconjugation Using Thiols: Old Chemistry Rediscovered to Connect Polymers with Nature's Building Blocks," ACS Macro Letters, 2:14-18 (2013).

* cited by examiner

PROTEIN-SURFACTANT-MONOMER/POLYMER BLENDS AND COPOLYMERS FOR PROTEIN-BASED PLASTICS

CROSS-REFERENCE TO RELATED APPLICATION

This application claims benefit of priority to U.S. Provisional Application No. 62/548,531 filed Aug. 22, 2017.

BACKGROUND

Polyurethanes are copolymers of isocyanates and alcohols that have excellent load bearing capacity, flexibility, abrasion and impact resistance, and a wide range of hardness. The polymers are formed from diol prepolymers, short diols, and diisocyanates, where the prepolymers form soft blocks and the diisocyanates and short diols react to form urethane bond-rich rigid blocks. At their working temperatures, soft domains of polyurethanes are rubbery and contribute to their extensibility, while the hard domains associate into crystalline regions that play the role of fillers and crosslinks, imparting stiffness and strength to the material[1,2]. This morphology and the advantageous properties of these materials are driven by incompatibility between hard and soft domains and extensive hydrogen bonding between the hard blocks[2]. Variation in the chemistry of the three components or in the proportion of prepolymer and small molar mass diol chain extender leads to easy customization of the properties[2]. However, the isocyanates used in polyurethane synthesis are known to be sensitizers and require careful handling[3]. This has led to a great deal of interest in developing non-isocyanate replacements for polyurethanes, for example hydroxyurethanes from the reaction of polycylic carbonates and polyamines[4,5].

In addition to the development of lower toxicity non-isocyanate polyurethanes, there is also substantial interest in the use of renewable feedstocks in these materials[6]. Demand for sustainable chemistry and bio-based macromolecular materials continues to grow, motivated by concerns regarding fossil fuel reliance, climate change, and waste, disposal problems[7,8]. Commonly investigated sustainable polyols are sourced from widely available plant based oils[9-11] and liquefied lignin[12]. Besides their low price, vegetable oils are also attractive as they have been shown to increase hydrophobicity of non-isocyanate hydroxyurethanes that are typically more hydrophilic than conventional polyurethanes[13]. Lignin[14] and amino acids[15] are also among the renewable materials investigated for hard segments and chain extenders, respectively. The preparation of polyurethane elastomers using primarily biomass materials through the use of lignin as the hard block and soybean oil have been reported[16].

Among the myriad of underutilized natural and sustainable materials derived from agricultural by-products or industrial surpluses, proteins have attracted much interest[17,18]. The stiffness resulting from inter- and intra-molecular associations in dry proteins have been exploited in material design targeted at commodity products and engineering plastics. In composites, proteins blended into rubbers and elastomers have been shown to aggregate, forming reinforcing networks similar to carbon black fillers[19]. The capability of proteins to form strong continuous matrices has led to the utilization of agricultural proteins in packaging materials[18,20], composites[21], fibers[22], and adhesives[23]. However, due to the extensive intermolecular interactions through hydrogen bonding, electrostatic forces, hydrophobic interactions, and disulfide bonding[24], protein based materials are generally stiff and brittle. This necessitates modification and plasticization to achieve useful materials[25], which typically allow protein materials to be more processable[26]. However, stiffness and strength are usually sacrificed for small improvements in extensibility, and the material has poor resistance to humidity, compounded by the use of hydrophilic plasticizers. Therefore, despite many structural and chemical analogies between proteins and synthetic polyurethanes, it remains challenging to develop strong and tough materials out of proteins for application as elastomers or engineering plastics.

Proteins, with their wide range of functionalities and structural confirmations, are amenable to conjugations to synthetic polymers. Grafting polymers onto proteins has been explored in various contexts that harness the biodegradability, renewability, and catalytic activity of proteins, including for biomedical applications[27], pharmaceutical synthesis[28], and defense[29]. Incorporation of peptide motifs into-polymer hybrids, particularly the β-sheet, has been of interest for their mechanical reinforcement as demonstrated in the synthesis of silk-mimetic polymers[30]. Graft polymerization has also been employed in the preparation of inexpensive multicomponent films where monomers were polymerized in the presence of proteins, as seen in the preparation of feather films[31,32]. These films, like many other bio-based materials facing challenges that limit their industrial applications, have relatively poor mechanical properties due to their low strength, or low toughness. Further efforts are therefore needed to develop a novel protein-based material with similar performance, structure, and morphology as polyurethanes using straightforward and controllable protein grafting strategies.

SUMMARY

In one aspect, the disclosure provides a copolymer comprising:
 (i) a plurality of a first monomer, wherein the first monomer is a modified protein comprising a protein and at least one functional group selected from the group consisting of an acrylate, a siloxane, a glycidyl ether, a vinyl group, an epoxy group, and a maleimide group;
 (ii) a plurality of a surfactant; and
 (iii) a plurality of a second monomer, wherein the second monomer is selected from the group consisting of an acrylate, a siloxane, a glycidyl ether, a monomer comprising a vinyl group, a monomer comprising an epoxy group, and a monomer comprising a maleimide group.

In one aspect, the disclosure provides a blend comprising:
 (i) a plurality of a protein;
 (ii) a plurality of a surfactant; and
 (iii) a plurality of a second monomer, wherein the second monomer is selected from the group consisting of an acrylate, a siloxane, a glycidyl ether, a monomer comprising a vinyl group, a monomer comprising an epoxy group, and a monomer comprising a maleimide group.

In another aspect, the disclosure provides a method of making a copolymer, comprising the steps of:
 a) combining a first monomer, a surfactant, and a second monomer, thereby forming a mixture;
 b) initiating polymerization of the mixture, thereby forming a copolymer comprising the
  (i) a plurality of a first monomer, wherein the first monomer is a modified protein comprising a protein and at least one functional group selected from the group consisting of an acrylate, a siloxane, a glycidyl ether, a vinyl group, an epoxy group, and a maleimide group;

(ii) a plurality of a surfactant; and (iii) a plurality of a second monomer, wherein the second monomer is selected from the group consisting of an acrylate, a siloxane, a glycidyl ether, a monomer comprising a vinyl group, a monomer comprising an epoxy group, and a monomer comprising a maleimide group.

In another aspect, the disclosure provides methods of making a blend disclosed herein, comprising the steps of:

a) combining a protein, a surfactant, and a second monomer, thereby forming a mixture;

b) initiating polymerization of the mixture, thereby forming a blend comprising (i) a plurality of a protein;

(ii) a plurality of a surfactant; and (iii) a plurality of a second monomer, wherein the second monomer is selected from the group consisting of an acrylate, a siloxane, a glycidyl ether, a monomer comprising a vinyl group, a monomer comprising an epoxy group, and a monomer comprising a maleimide group.

In some embodiments, the disclosure provides an article comprising the copolymers disclosed herein.

In some embodiments, the disclosure provides an article comprising the blends disclosed herein.

DETAILED DESCRIPTION

Overview

Figure 1:
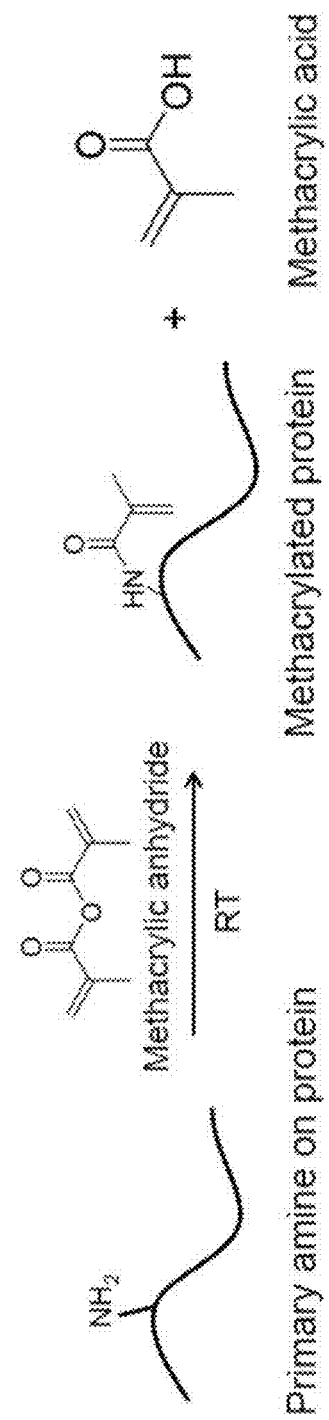
FIG. 1 is a schematic representation of preparing an exemplary modified protein.

The use of biomass-based feedstocks in chemical and material manufacturing has been widely investigated as an approach to reduce dependence on fossil fuel-derived chemicals. As proteins are abundant in biomass sources such as agricultural and forestry feedstocks, plant and animal based agricultural byproducts, and municipal wastes, transformation of proteins into value-added products can contribute to material sustainability. Proteins have many potential uses in plastic applications due to their capability to form continuous matrices and the abundance of reactive functional groups that are amenable to chemical modification. Proteins have great potential as biomass-derived feedstocks for material synthesis and can form strong materials due to their highly hydrogen bonded nature. However, in the absence of protein modification or plasticizers, proteins are known to be too brittle to handle and form.

Plasticization is a commonly employed strategy that increases processability of protein-based materials and enables them to be thermoformed. The plasticizers reduce glass transitions or softening temperatures of proteins by disrupting polymer-polymer interactions and increasing the free volume of protein chains. Various hydrophilic small molecule plasticizers such as water, ethylene glycol, sorbitol, and glycerol have typically been explored to allow proteins to be processed at lower temperatures that limit decomposition. While surfactants are generally regarded as poor plasticizers on their own, complexing ionic surfactants with charged proteins has been studied by others to prepare low melting point proteins, where the disruption of electrostatic interactions between proteins has allowed proteins with catalytic activity to be liquefied even in the absence of solvent. In protein-based materials, plasticizers are crucial for ease of processing and molding, but the increase in flexibility is typically achieved at the cost of reduced mechanical strength.

The mechanical properties of protein-based materials are also usually strongly dependent on the humidity of the environment due to their hydrophilicity. This is often compounded by the use of hydrophilic plasticizers, which greatly limit material applications and versatility. As lowering hydrophilicity of protein-based materials, among other desirable properties, can greatly increase their utility, many previous studies have explored incorporating hydrophobic plasticizers such as lipids, long chain fatty acids, and waxes to limit moisture absorption of protein films. Although these molecules reduce material sensitivity to humidity, incompatibility between plasticizer and protein due to solubility differences can lead to ineffective plasticization and poor solvation of plasticizer in the polymer. The insolubility of unmodified proteins in most organic solvents and common monomers in the absence of salts or other mediators also presents a major challenge for formulating blends and conjugates with non-water soluble plasticizers or polymers. This issue is also encountered in protein biocatalysis, where performing reactions in organic solvents or even in solvent free conditions can be of high value. Methods such as protein chemical modification, immobilization on solid surfaces, co-lyophilization with protectants, and surfactant complexation have been widely explored to address these solubility challenges.

Proteins are a widely available biomass source for synthesizing strong and tough engineering polymers due to their propensity to hydrogen bond, chemically stable amide backbone, and demonstrated efficacy at forming relevant material structures in nature. Because the properties of polypeptides in many ways mimic urethane bonds and hard domains, herein proteins are explored as a replacement for isocyanates in the formation of polyurethane-like elastomers to decrease toxicity and improve sustainability. The polymers comprise covalently bonded protein and flexible polymer with a hydrophobic component.

Polymeric materials comprised partially or fully of renewable protein sources have great potential at improving sustainability in the polymer industry and reducing the environmental and energy impact. In addition, the development of protein-based engineering resins also valorizes underutilized protein-based waste streams in agriculture. This disclosure reports the development of a family of protein based formulations that allows protein-based resins to be processed, polymerized, and cured with surfactants as the compatibilizer. Proteins are first mixed with surfactants to prepare low melting point protein-surfactant complexes, then copolymerized and cured with additional monomers or prepolymers to prepare hydrophobic resins. Surfactant compatibilizers enable proteins to be miscible with a larger range of compounds both in the presence and absence of solvents. Materials with a wide range of stiffness have been prepared by varying the fraction of protein macrocrosslinkers in the materials. The protein copolymers are stronger and tougher than unreinforced homopolymers and more extensible than unmodified proteins. Materials with low crosslink densities prepared using proteins modified at low methacrylation levels are also stiffer than protein-polymer blends. Above an optimal protein methacrylation level, increasing chemical crosslink densities led to lower extents of protein aggregation and decreased moduli.

Proteins can be difficult to formulate and process, so the disclosure provides a strategy to increase feasibility and address challenges in formulating protein-based materials. In some embodiments, proteins can be liquefied with surfactant. In some embodiments, the polymer is formed without solvent. In some embodiments, surfactants lower the softening point of proteins and compatibilize mixtures of proteins and hydrophobic monomers. In some embodiments, proteins mimic hard domains of polymers. In some embodiments, proteins acting as hard domains enhance mechanical performance of polymers.

A solvent free, bulk polymerization approach allows materials to be prepared using conventional melt processing methods such as injection molding and compression molding, but requires all components of the starting raw materials to be above their melting temperature. Since most dry proteins' softening temperatures are high and too close to their decomposition temperature, this is achieved by plasticizing the proteins with surfactants. Surfactants investigated include ionic surfactants (both cationic and anionic surfactants), surfactants with and without polymerizable groups consisting of vinyl moieties, non-ionic surfactants, and zwitterionic surfactants. Blends can be prepared by directly mixing the surfactant with proteins, or dissolving both in a common solvent such as water, ethanol, propanol, and drying off the solvent. Based on the choice of surfactants, resulting protein-surfactant complex can have glass transition temperatures below their decomposition temperature, and can appear to be optically clear.

Agricultural proteins are of particular interest for formulating materials due to their abundance and low cost. Proteins that would be a likely source of the materials include milk proteins casein and whey, wheat, silk, soy, zein, algal and fish proteins, peptides from agricultural protein hydrolysates, and recombinant proteins. Other proteins may also be available from organic waste sources in the future as organic waste recycling technology develops. Prior to blending with surfactants, proteins can be modified to contain polymerizable groups such as acrylamides, where the acrylamides are formed from acrylate anhydride-amine reactions. Polymerizable groups allow the proteins to be cross-linked or attached to other monomers. Other polymerizable groups include but are not limited to glycidyl ethers and vinyl groups.

The protein-surfactant complex can then be blended with a second monomer, for example, with vinyl or acrylate groups, that can be polymerized via free radical polymerization to prepare a copolymer. Proteins are typically slightly hygroscopic, and are often plasticized with water-soluble small molecules or polymers to promote processability. This results in hydrophilic materials that have undesirable mechanical property dependence on humidity. In this invention, surfactants serve as compatibilizers that allow proteins to be blended with a variety of monomers to prepare materials with large ranges of properties and hydrophobicities. Elastomeric or rubbery materials can be prepared by selecting monomers that have low homopolymer glass transition temperature, while glassy materials can be prepared using monomers with high homopolymer glass transition temperature.

Polymerization of the second monomer is initiated by thermal free radical initiators or photoinitiators. This allows the complete formulation containing protein, surfactant, second monomer, and initiator to be pre-blended and to remain stable at storage conditions. Materials are fabricated by applying heat or irradiation to initiate the polymerization and curing process.

Resins can also be prepared by blending or reacting the protein-surfactant complex with pre-formed polymers using common bioconjugation chemistries.[58] The reactive group on the protein can either be natural functionalities (e.g., amines, cysteins, tyrosines, etc.) or unnatural functionalities that are usually more reactive and chemoselective. When multiple reactive groups are present on proteins and polymers, they can react to form longer chains through step-growth polymerization. Some examples of these bioconjugation reactions include glycidyl ether-amine reaction,[59] thiol-ene coupling,[60] N-terminus oxime ligation,[61] Michael addition reactions,[62] and many more.

In certain embodiments, provided herein is a facile chain growth polymerization strategy for formulating strong and tough protein-based copolymers with ionic surfactants, polymerizable surfactants, non-ionic surfactants, and zwitterionic surfactants for applications including as a potential isocyanate-free polyurethane alternative.

Exemplary Copolymers and Blends

In some embodiments, the copolymers disclosed herein are elastomers. In some embodiments, the elastomers comprise a plurality of proteins and a plurality of second monomers. In some embodiments, the copolymers comprise a hydrophobic monomer.

In one aspect, provided herein is a copolymer comprising:
(i) a plurality of a first monomer, wherein the first monomer is a modified protein comprising a protein and at least one functional group selected from the group consisting of an acrylate, a siloxane, a glycidyl ether, a vinyl group, an epoxy group, a maleimide group, and an N-hydroxysuccinimide ester;
(ii) a plurality of a surfactant; and
(iii) a plurality of a second monomer, wherein the second monomer is selected from the group consisting of an acrylate, a siloxane, a glycidyl ether, an amine, a monomer comprising a vinyl group, a monomer comprising an epoxy group, and a monomer comprising a maleimide group.

In another aspect, provided herein is a blend comprising:
(i) a plurality of a protein;
(ii) a plurality of a surfactant; and
(iii) a plurality of a second monomer, wherein the second monomer is selected from the group consisting of an acrylate, a siloxane, a glycidyl ether, an amine, a monomer comprising a vinyl group, a monomer comprising an epoxy group, and a monomer comprising a maleimide group.

In some embodiments of the copolymers disclosed herein, at least two instances of the first monomer form a protein aggregate. In some embodiments of the blends disclosed herein, at least two instances of the protein form a protein aggregate. In some embodiments of the copolymers and the blends disclosed herein, the protein aggregate forms an α-helix. In some embodiments, the protein aggregate forms a β-sheet.

In some embodiments, the first monomer is a modified protein comprising a protein and at least one functional group selected from the group consisting of an acrylate, a siloxane, a glycidyl ether, a vinyl group, an epoxy group, and a maleimide group.

In some embodiments, the first monomer comprises an acrylate.

In some embodiments, the first monomer comprises a vinyl group. In some embodiments, the first monomer comprising a vinyl group is selected from the group consisting of an acrylate, a maleimide group, and an alkene group.

In some embodiments, the first monomer comprises an epoxy group.

In some embodiments, the first monomer comprises a maleimide group.

In some embodiments, the first monomer comprises an N-hydroxysuccinimide ester.

In some embodiments, the protein is selected from the group consisting of gelatin A, gelatin B, whey protein concentrate, whey protein isolate, β-lactoglobulin, α-lactalbumin, serum albumin, immunoglobin, casein, wheat, silk, soy, zein, algal proteins, fish proteins, lysozyme, synthetic proteins, protein hydrolysates from agricultural crops, recombinant proteins, and a mixture of any of them. In some embodiments, the protein is selected from the group consisting of whey protein concentrate, whey protein isolate, β-lactoglobulin, α-lactalbumin, serum albumin, immunoglobin, casein, wheat, silk, soy, zein, algal proteins, fish proteins, synthetic proteins, protein hydrolysates from agricultural crops, recombinant proteins, and a mixture of any of them. In some embodiments, the protein is selected from the group consisting of whey protein concentrate, whey protein isolate, β-lactoglobulin, α-lactalbumin, serum albumin, immunoglobin, casein, wheat, silk, soy, zein, algal proteins, fish proteins, synthetic proteins, protein hydrolysates from agricultural crops, and a mixture of any of them. In some embodiments, the protein is selected from the group consisting of gelatin A, gelatin B, whey protein concentrate, whey protein isolate, β-lactoglobulin, α-lactalbumin, serum albumin, immunoglobin, casein, wheat, silk, soy, zein, algal proteins, fish proteins, lysozyme, and a mixture of any of them. In some embodiments, the protein is selected from the group consisting of whey protein concentrate, whey protein isolate, β-lactoglobulin, α-lactalbumin, serum albumin, immunoglobin, and a mixture of any of them. In some embodiments, the protein is selected from the group consisting of gelatin A, gelatin B, whey protein concentrate, whey protein isolate, β-lactoglobulin, α-lactalbumin, serum albumin, immunoglobin, zein, lysozyme, and a mixture of any of them. In some embodiments, the protein hydrolysates from agricultural crops include but are not limited to protein hydrolysates from barley, canola, potato, rapeseed, soy, sunflower, wheat, and wheat germ.

In some embodiments, the protein is whey protein isolate or β-lactoglobulin. In some embodiments, the protein is whey protein isolate. In some embodiments of the copolymers disclosed herein, the modified protein comprises an amide; and the amide is formed from an anhydride and an unmodified protein comprising an amine. In some embodiments, the second monomer comprises a polymerizable group, including acrylates. In some embodiments, the anhydride is acrylic anhydride. In some embodiments, the anhydride is methacrylic anhydride. In some embodiments, the modified protein comprises an acrylamide; and the acrylamide is formed from an anhydride and an unmodified protein comprising an amine. In some embodiments, a first monomer is a protein was first modified using a reaction with methacrylic anhydride to allow it to be polymerizable, followed by a polymerization step that allows the protein to be randomly copolymerized along with (meth)acrylate second monomers that make up the flexible soft segment in the material. Whey protein isolate (WPI), a well-studied mixture of proteins composed primarily of β-lactoglobulin (BLG), α-lactalbumin, serum albumin, and immunoglobulins was chosen as a model of crude protein biomass. Materials synthesized using WPI and BLG were compared to study the effects of protein purity. Effects of protein content and crosslink density, and structure-property relationships of the copolymer were investigated, and mechanical properties of the elastomers were compared to those of polyurethanes.

In some embodiments, the modified protein is charged.

In some embodiments, the surfactant is an ionic surfactant.

In some embodiments, the ionic surfactant has the opposite charge of the modified protein. Surfactant serves as a compatibilizer that allows proteins to be miscible with monomers with various properties and hydrophobicity, enabling the preparation of hydrophobic protein-based materials. This is important because most current protein-based materials are too hygroscopic to be interesting for any real applications.

In some embodiments, the surfactant has a low melting point.

In some embodiments, a low melting point protein-surfactant complex is prepared by blending a charged protein at a pH below or above its pI with ionic surfactants that have an opposite charge. In some embodiments, the ionic surfactant lowers the temperature of the softening point of proteins. In some embodiments, the low melting point of the surfactant, of the mixture comprising a modified protein and a surfactant, or of the mixture comprising a protein and a surfactant is less than about 250° C. In some embodiments, the melting point is less than about 240° C., less than about 230° C., less than about 220° C., less than about 210° C., less than about 200° C., less than about 195° C., less than about 190° C., less than about 185° C., less than about 180° C., less than about 175° C., less than about 170° C., less than about 165° C., less than about 160° C., less than about 155° C., less than about 150° C., less than about 145° C., less than about 140° C., less than about 135° C., less than about 130° C., less than about 125° C., less than about 120° C., less than about 115° C., less than about 110° C., less than about 105° C., less than about 100° C., less than about 95° C., less than about 90° C., less than about 85° C., less than about 80° C., less than about 75° C., less than about 70° C., less than about 65° C., less than about 60° C., less than about 55° C., less than about 50° C., less than about 45° C., less than about 40° C., less than about 35° C., less than about 30° C., less than about 25° C., less than about 20° C., or less than about 15° C. In some embodiments, the melting point is less than about 200° C. In some embodiments, the melting point is less than about 100° C. In some embodiments, the melting point is less than about 80° C.

In some embodiments, the melting point of the surfactant, of the mixture comprising a modified protein and a surfactant, or of the mixture comprising a protein and a surfactant is between about 10° C. and about 250° C. In some embodiments, the melting point is selected from the group consisting of about 10° C., about 11° C., about 12° C., about 13° C., about 14° C., about 15° C., about 16° C., about 17° C., about 18° C., about 19° C., about 20° C., about 21° C., about 22° C., about 23° C., about 24° C., about 25° C., about 26° C., about 27° C., about 28° C., about 29° C., about 30° C., about 31° C., about 32° C., about 33° C., about 34° C., about 35° C., about 36° C., about 37° C., about 38° C., about 39° C., about 40° C., about 41° C., about 42° C., about 43° C., about 44° C., about 45° C., about 46° C., about 47° C., about 48° C., about 49° C., about 50° C., about 51° C., about 52° C., about 53° C., about 54° C., about 55° C., about 56° C., about 57° C., about 58° C., about 59° C., about 60° C., about 61° C., about 62° C., about 63° C., about 64° C., about 65° C., about 66° C., about 67° C., about 68° C., about 69° C., about 70° C., about 71° C., about 72° C., about 73° C., about 74° C., about 75° C., about 76° C., about 77° C., about 78° C., about 79° C., about 80° C., about 81° C., about 82° C., about 83° C., about 84° C., about 85° C., about 86° C., about 87° C., about 88° C., about 89° C., about 90° C., about 91° C., about 92° C., about 93° C., about 94° C., about 95° C., about 96° C., about 97° C., about 98° C., about 99° C., about 100° C., about 105° C., about 110° C., about 115° C., about 120° C., about 125° C., about 130° C., about 135° C., about 140° C., about 145° C., about 150° C., about 155° C., about 160° C., about 165° C., about 170° C., about 175° C., about 180° C., about 185° C., about 190° C., about 195° C., about 200° C., about 205° C., about 210° C., about 215° C., about 220° C., about 225° C., about 230° C., about 235° C., about 240° C., about 245° C., and about 250° C. In some embodiments, the melting point is between about 10° C. and about 240° C. In some embodiments, the melting point is between about 10° C. and about 200° C. In some embodiments, the melting point is between about 10° C. and about 100° C. In some embodiments, the melting point is between about 15° C. and about 90° C. In some embodiments, the melting point is between about 20° C. and about 80° C.

In some embodiments, the modified protein is cationic. In some embodiments, the ionic surfactant is an anionic surfactant. In some embodiments, the ionic surfactant is selected from the group consisting of a sulfate, an alkyl sulfate, a carboxylate, and an alkyl carboxylic acid: In some embodiments, the ionic surfactant is selected from the group consisting of an alkyl sulfate (e.g., sodium dodecyl sulfate) and an alkyl carboxylic acid (e.g., polyoxyethylene octyl ether carboxylic acid). In some embodiments, the ionic surfactant is selected from the group consisting of sodium dodecyl sulfate, ammonium dodecyl sulfate, sodium laurate, sodium lauryl ether sulfate, poly(ethylene glycol) 4-nonylphenyl-3-sulfopropyl ether potassium salt, sodium stearate, sodium dodecylbenzenesulfonate, sodium oleate, dioctyl sulfosuccinate, and a mixture of any of them. In some embodiments, the ionic surfactant is selected from the group consisting of sodium dodecyl sulfate, ammonium dodecyl sulfate, sodium laurate, sodium lauryl ether sulfate, sodium stearate, sodium dodecylbenzenesulfonate, poly(ethylene glycol) 4-nonylphenyl-3-sulfopropyl ether potassium salt, and a mixture of any of them. In some embodiments, the ionic surfactant is selected from the group consisting of poly(ethylene glycol) 4-nonylphenyl-3-sulfopropyl ether potassium salt, sodium oleate, dioctyl sulfosuccinate, and a mixture of any of them. In some embodiments, the ionic surfactant is sodium oleate. In some embodiments, the ionic surfactant is dioctyl sulfosuccinate.

In some embodiments, the ionic surfactant has the following structural formula:

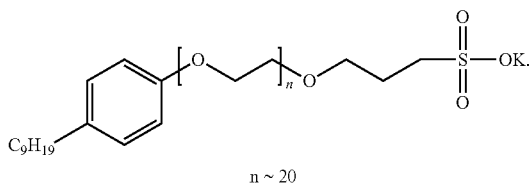

In some embodiments, the ionic surfactant has the following structural formula:

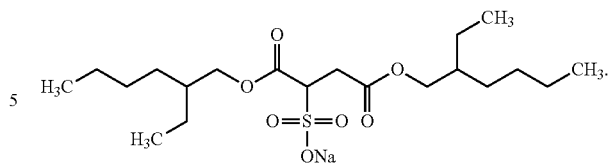

In some embodiments, the modified protein is anionic. In some embodiments, the ionic surfactant is a cationic surfactant. In some embodiments, the ionic surfactant is a cationic quaternary ammonium surfactant. In some embodiments, the ionic surfactant is selected from the group consisting of a cationic quaternary amine, an alkyl pyridinium, and an imidazolium. In some embodiments, the imidazolium is polymerizable. In some embodiments, the ionic surfactant is selected from the group consisting of a benzalkonium chloride, benzethonium chloride, cetylpyridinium chloride, cetyltrimethylammonium bromide, cetryltrimethylammonium chloride, didecyldimethylammonium chloride, dioctadecyldimethylammonium bromide, docosyltrimethylammonium chloride, octenidine dihydrochloride, 1-vinyl-3-dodecylimidazolium bromide, and a mixture of any of them. In some embodiments, the ionic surfactant is selected from the group consisting of a benzalkonium chloride, benzethonium chloride, cetylpyridinium chloride, cetyltrimethylammonium bromide, cetryltrimethylammonium chloride, didecyldimethylammonium chloride, dioctadecyldimethylammonium bromide, docosyltrimethylammonium chloride, octenidine dihydrochloride, and a mixture of any of them. In some embodiments, the ionic surfactant is selected from the group consisting of a benzalkonium chloride, cetylpyridinium chloride, 1-vinyl-3-dodecylimidazolium bromide, and a mixture of any of them.

In some embodiments, the ionic surfactant has the following structural formula:

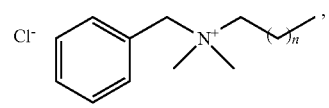

wherein n is an integer from 2 to 22. In some embodiments, n is selected from the group consisting of 8, 10, 12, 14, 16, and 18.

In some embodiments, the ionic surfactant has the following structural formula:

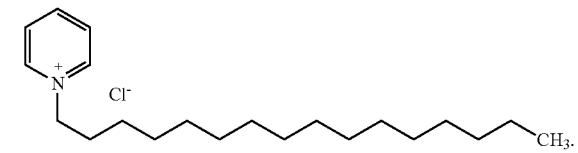

In some embodiments, the ionic surfactant is selected from the group consisting of a benzalkonium chloride, cetylpyridinium chloride, 1-vinyl-3-dodecylimidazolium bromide, sodium oleate, dioctyl sulfosuccinate, and a mixture of any of them.

In some embodiments, the surfactant comprises a polymerizable group selected from the group consisting of an acrylate, a siloxane, a glycidyl ether, a vinyl group, an epoxy group, and a maleimide group. In some embodiments, the surfactant comprises a polymerizable group selected from the group consisting of an acrylate, a siloxane, a glycidyl ether, a vinyl group, and an epoxy group. In some embodiments, the surfactant comprises a polymerizable group, wherein the polymerizable group is a vinyl group. In some embodiments, the surfactant is selected from the group consisting of phosphate esters of polypropylene glycol (PPG) monomethacrylate (e.g., SIPOMER®Pam-200), polyoxyethylene alkylphenyl ether ammonium sulfates (e.g., HITENOL® BC), and ammonium polyoxyalkylene alkenyl ether sulfates (e.g., LATEMUL®PD-104). In some embodiments, the surfactant is selected from the group consisting of the following structural formulas:

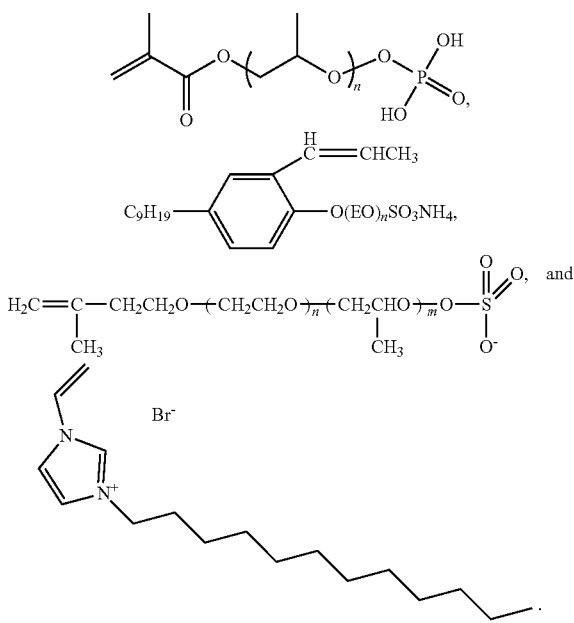

In some embodiments, the surfactant is selected from the group consisting of the following structural formulas:

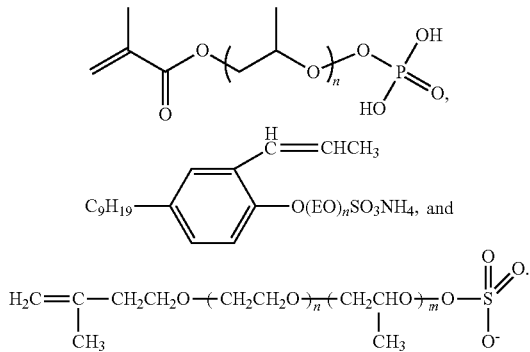

In some embodiments, the surfactant is 1-vinyl-3-dodecylimidazolium bromide.

In some embodiments, the surfactant is a non-ionic surfactant. In some embodiments, the non-ionic surfactant is selected from the group consisting of polyethylene glycol alkyl ethers, polypropylene glycol alkyl ethers, glucoside alkyl ethers, polyethylene glycol octylphenyl ethers (e.g., Triton X-100), glycerol alkyl ethers, polysorbates, sorbitan alkyl esters, and poloxamers.

In some embodiments, the non-ionic surfactant has the following structural formula:

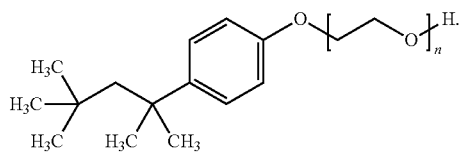

In some embodiments, the surfactant is a zwitterionic surfactant. In some embodiments, the zwitterionic surfactant is selected from the group consisting of amine oxides (e.g., lauryldimethylamine oxide and myristamine oxide), amphoacetates (e.g., sodium lauroamphoacetate), betaines, 3-[(3-cholamidopropyl)dimethylammonio]-1-propanesulfonate, cocamidopropyl betaine, cocamidopropyl hydroxysultaine, glycerophospholipids (e.g., phosphatidylcholine, phosphatidylethanolamine, phosphatidylinositol, phophatidic acid, and dipalmitoylphosphatidylcholine), hydroxysultaines, and lechithins (e.g., soy lecithin).

In some embodiments, the zwitterionic surfactant has the following structural formula:

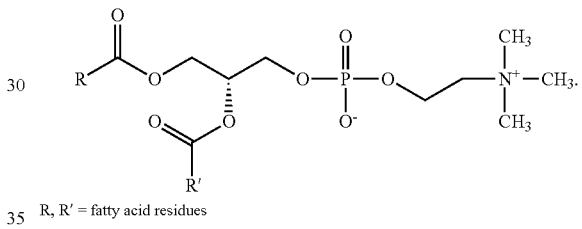

R, R' = fatty acid residues

In some embodiments of the copolymers disclosed herein, the molar ratio of surfactant to modified protein or the molar ratio of surfactant to protein is about 0.1 to about 15. In some embodiments, the molar ratio of surfactant to modified protein or the molar ratio of surfactant to protein is selected from the group consisting of about 0.1, about 0.2, about 0.3, about 0.4, about 0.5, about 0.6, about 0.7, about 0.8, about 0.9, about 1.0, about 1.1, about 1.2, about 1.3, about 1.4, about 1.5, about 1.6, about 1.7, about 1.8, about 1.9, about 2.0, about 2.1, about 2.2, about 2.3, about 2.4, about 2.5, about 2.6, about 2.7, about 2.8, about 2.9, about 3.0, about 3.1, about 3.2, about 3.3, about 3.4, about 3.5, about 3.6, about 3.7, about 3.8, about 3.9, about 4.0, about 4.1, about 4.2, about 4.3, about 4.4, about 4.5, about 4.6, about 4.7, about 4.8, about 4.9, about 5.0, about 5.1, about 5.2, about 5.3, about 5.4, about 5.5, about 5.6, about 5.7, about 5.8, about 5.9, about 6.0, about 6.1, about 6.2, about 6.3, about 6.4, about 6.5, about 6.6, about 6.7, about 6.8, about 6.9, about 7.0, about 7.1, about 7.2, about 7.3, about 7.4, about 7.5, about 7.6, about 7.7, about 7.8, about 7.9, about 8.0, about 8.5, about 9.0, about 9.5, about 10.0, about 10.5, about 11.0, about 11.5, about 12.0, about 12.5, about 13.0, about 13.5, about 14.0, about 14.5, and about 15.0. In some embodiments, the molar ratio of surfactant to modified protein or the molar ratio of surfactant to protein is about 0.1 to about 10. In some embodiments, the molar ratio of surfactant to modified protein or the molar ratio of surfactant to protein is about 0.1 to about 5. In some embodiments, the molar ratio of surfactant to modified protein or the molar ratio of surfactant to protein is about 1.0 to about 3.0. In some embodiments, the molar ratio of surfactant to modified protein or the molar ratio of surfactant to protein is about 2.0.

In some embodiments of the copolymers disclosed herein, the second monomer is selected from the group consisting of an acrylate, a siloxane, a glycidyl ether, a monomer comprising a vinyl group, a monomer comprising an epoxy group, and a monomer comprising a maleimide group.

In some embodiments of the copolymers disclosed herein, the second monomer is selected from the group consisting of acrylamide, dimethylacrylamide, methyl methacrylate, ethyl acrylate, n-butyl acrylate, glycidyl methacrylate, hydroxyl ethyl methacrylate, ethylene glycol diacrylate, acrylic acid, methacrylic acid, poly(ethylene glycol) methyl ether methacrylate (PEGMA), hydroxypropyl acrylate (HPA), poly(ethylene glycol) diacrylate (PEGDA), 2-vinyl pyridine, 4-vinyl pyridine, p-divinylbenzene, m-divinylbenzene, sty-lene, styrene, trivinlytrimethylcyclotrisiloxane, tetravinylte-tramethylcyclotetrasiloxane, trivinyltrimethylcyclo-trisila-zane, tetravinyltetramethylcyclotetrasilazane, and a mixture of any of them. In some embodiments, the second monomer is selected from the group consisting of methyl methacry-late, ethyl acrylate, n-butyl acrylate, glycidyl methacrylate, hydroxyl ethyl methacrylate, ethylene glycol diacrylate, methacrylic acid, PEGMA, HPA, PEGDA, 2-vinyl pyridine, 4-vinyl pyridine, p-divinylbenzene, m-divinylbenzene, sty-lene, trivinlytrimethylcyclotrisiloxane, tetravinyltetrameth-ylcyclotetrasiloxane, trivinyltrimethylcyclo-trisilazane, tet-ravinyltetramethylcyclotetrasilazane, and a mixture of any of them. In some embodiments, the second monomer is selected from the group consisting of acrylamide, dimethy-lacrylamide, methyl methacrylate, n-butyl acrylate, glycidyl methacrylate, hydroxyl ethyl methacrylate, ethylene glycol diacrylate, acrylic acid, methacrylic acid, PEGMA, HPA, PEGDA, styrene, and a mixture of any of them. In some embodiments, the second monomer is selected from the group consisting of acrylamide, dimethylacrylamide, n-butyl acrylate, acrylic acid, methacrylic acid, PEGMA, styrene, and a mixture of any of them.

In some embodiments, the second monomer is an acry-late. In some embodiments, the second monomer is selected from the group consisting of methyl methacrylate, n-butyl acrylate, glycidyl methacrylate, hydroxyl ethyl methacry-late, ethylene glycol diacylate, methacrylic acid, PEGMA, HPA, PEGDA, and a mixture of any of them. In some embodiments, the second monomer is n-butyl acrylate.

In some embodiments of the copolymers disclosed herein, the ratio of first monomer (modified protein) to second monomer or the ratio of protein to second monomer is about 10,000:1 to about 0.1:1. In some embodiments, the ratio of first monomer to second monomer is selected from the group consisting of about 10,000:1, about 9,900:1, about 9,800:1, about 9,700:1, about 9,600:1, about 9,500:1, about 9,400:1, about 9,300:1, about 9,200:1, about 9,100:1, about 9,000:1, about 8,900:1, about 8,800:1, about 8,700:1, about 8,600:1, about 8,500:1, about 8,400:1, about 8,300:1, about 8,200:1, about 8,100:1, about 8,000:1, about 7,900:1, about 7,800:1, about 7,700:1, about 7,600:1, about 7,500:1, about 7,400:1, about 7,300:1, about 7,200:1, about 7,100:1, about 7,000:1, about 6,900:1, about 6,800:1, about 6,700:1, about 6,600:1, about 6,500:1, about 6,400:1, about 6,300:1, about 6,200:1, about 6,100:1, about 6,000:1, about 5,900:1, about 5,800:1, about 5,700:1, about 5,600:1, about 5,500:1, about 5,400:1, about 5,300:1, about 5,200:1, about 5,100:1, about 5,000:1, about 4,900:1, about 4,800:1, about 4,700:1, about 4,600:1, about 4,500:1, about 4,400:1, about 4,300:1, about 4,200:1, about 4,100:1, about 4,000:1, about 3,900:1, about 3,800:1, about 3,700:1, about 3,600:1, about 3,500:1, about 3,400:1, about 3,300:1, about 3,200:1, about 3,100:1, about 3,000:1, about 2,900:1, about 2,800:1, about 2,700:1, about 2,600:1, about 2,500:1, about 2,400:1, about 2,300:1, about 2,200:1, about 2,100:1, about 2,000:1, about 1,900:1, about 1,800:1, about 1,700:1, about 1,600:1, about 1,500:1, about 1,400:1, about 1,300:1, about 1,200:1, about 1,100:1, about 1,000:1, about 950:1, about 900:1, about 850:1, about 800:1, about 750:1, about 700:1, about 650:1, about 600:1, about 550:1, about 500:1, about 450:1, about 400:1, about 350:1, about 300:1, about 250:1, about 200:1, about 150:1, about 100:1, about 50:1, about 25:1, about 20:1, about 19:1, about 18:1, about 17:1, about 16:1, about 15:1, about 14:1, about 13:1, about 12:1, about 11:1, about 10:1, about 9:1, about 8:1, about 7:1, about 6:1, about 5:1, about 4:1, about 3:1, about 2:1, about 1.5:1, about 1:1, about 0.95:1, about 0.9:1, about 0.85:1, about 0.8:1, about 0.75:1, about 0.7:1, about 0.65:1, about 0.6:1, about 0.55:1, about 0.5:1, about 0.45:1, about 0.4:1, about 0.35:1, about 0.33:1, about 0.3:1, about 0.25:1, about 0.2:1, about 0.15:1, and about 0.1:1. In some embodi-ments, the ratio of first monomer to second monomer or the ratio of protein to second monomer is about 1,000:1 to about 0.1:1. In some embodiments, the ratio of first monomer to second monomer or the ratio of protein to second monomer is about 500:1 to about 0.1:1. In some embodiments, the ratio of first monomer to second monomer or the ratio of protein to second monomer is about 100:1 to about 0.1:1. In some embodiments, the ratio of first monomer to second monomer or the ratio of protein to second monomer is about 20:1 to about 0.1:1. In some embodiments, the ratio of first monomer to second monomer or the ratio of protein to second monomer is about 1:1 to about 0.1:1. In some embodiments, the ratio of first monomer to second monomer or the ratio of protein to second monomer is about 0.33:1.

Methods of Making Copolymers and Blends

Provided herein are methods of making a copolymer comprising the steps of:
 a) combining a first monomer, a surfactant, and a second monomer, thereby forming a mixture;
 b) initiating polymerization of the mixture, thereby forming a copolymer comprising
  (i) a plurality of a first monomer, wherein the first monomer is a modified protein comprising a protein and at least one functional group selected from the group consisting of an acrylate, a siloxane, a glycidyl ether, a vinyl group, an epoxy group, and a maleimide group;
  (ii) a plurality of a surfactant; and
  (iii) a plurality of a second monomer, wherein the second monomer is selected from the group consisting of an acrylate, a siloxane, a glycidyl ether, a monomer comprising a vinyl group, a monomer comprising an epoxy group, and a monomer comprising a maleimide group.

Provided herein are methods of making a blend comprising the steps of:
 a) combining a protein, a surfactant, and a second monomer, thereby forming a mixture;
 b) initiating polymerization of the mixture, thereby forming a blend comprising
  (i) a plurality of a protein;
  (ii) a plurality of a surfactant; and
  (iii) a plurality of a second monomer, wherein the second monomer is selected from the group consisting of an acrylate, a siloxane, a glycidyl ether, a monomer comprising a vinyl group, a monomer comprising an epoxy group, and a monomer comprising a maleimide group.

In some embodiments, of the methods disclosed herein, prior to step a), a first monomer, a surfactant, and a second monomer or a protein, a surfactant, and a second monomer are combined and heated. In some embodiments, prior to step a), a first monomer, a surfactant, and a second monomer or a protein, a surfactant, and a second monomer are combined and heated to >100° C.

In some embodiments, of the methods disclosed herein, the modified protein comprises an amide; and the amide is formed from an anhydride and an unmodified protein comprising an amine. In some embodiments, the anhydride is acrylic anhydride or methacrylic anhydride. In some embodiments, the anhydride is acrylic anhydride. In some embodiments, the anhydride is methacrylic anhydride.

In some embodiments, of the methods disclosed herein, the molar ratio of anhydride to protein is about 0.5 to about 15. In some embodiments, the molar ratio of anhydride to protein is selected from the group consisting of about 0.5, about 0.6, about 0.7, about 0.8, about 0.9, about 1.0, about 1.1, about 1.2, about 1.3, about 1.4, about 1.5, about 1.6, about 1.7, about 1.8, about 1.9, about 2.0, about 2.1, about 2.2, about 2.3, about 2.4, about 2.5, about 2.6, about 2.7, about 2.8, about 2.9, about 3.0, about 3.1, about 3.2, about 3.3, about 3.4, about 3.5, about 3.6, about 3.7, about 3.8, about 3.9, about 4.0, about 4.1, about 4.2, about 4.3, about 4.4, about 4.5, about 4.6, about 4.7, about 4.8, about 4.9, about 5.0, about 5.1, about 5.2, about 5.3, about 5.4, about 5.5, about 5.6, about 5.7, about 5.8, about 5.9, about 6.0, about 6.1, about 6.2, about 6.3, about 6.4, about 6.5, about 6.6, about 6.7, about 6.8, about 6.9, about 7.0, about 7.1, about 7.2, about 7.3, about 7.4, about 7.5, about 7.6, about 7.7, about 7.8, about 7.9, about 8.0, about 8.5, about 9.0, about 9.5, about 10.0, about 10.5, about 11.0, about 11.5, about 12.0, about 12.5, about 13.0, about 13.5, about 14.0, about 14.5, and about 15.0. In some embodiments, the molar ratio of anhydride to protein is about 1 to about 10. In some embodiments, the molar ratio of anhydride to protein is about 1 to about 7.

In some embodiments of the copolymers disclosed herein, the number of modification sites on the modified protein is about 0.5 to about 15. In some embodiments, the number of modification sites on the modified protein is selected from the group consisting of about 0.5, about 1, about 1.5, about 2.0, about 2.5, about 3.0, about 3.5, about 4.0, about 4.5, about 5.0, about 5.5, about 6.0, about 6.5, about 7.0, about 7.5, about 8.0, about 8.5, about 9.0, about 9.5, about 10.0, about 10.5, about 11.0, about 11.5, about 12.0, about 12.5, about 13.0, about 13.5, about 14.0, about 14.5, and about 15. In some embodiments, the number of modification sites on the modified protein is selected from the group consisting of 1, 2, 3, 4, 5, 6, 7, 8, 9, 10, and 11.

In some embodiments, of the methods disclosed herein, the method is solvent free. In some embodiments, the method further comprises providing a plasticizer. The proposed technology allows materials to be fabricated without the use of solvents (although plasticizers may still be included in the formulation as desired) which eliminates drying steps, and also material shrinkage and warping as a result of drying after polymerization. This critically enables protein-based plastic parts to be manufactured using compression molding and injection molding.

In some embodiments of the copolymers disclosed herein, the copolymer comprises a weight percent of a modified protein or a protein selected from the group consisting of about 5%, about 6%, about 7%, about 8%, about 9%, about 10%, about 11%, about 12%, about 13%, about 14%, about 15%, about 16%, about 17%, about 18%, about 19%, about 20%, about 21%, about 22%, about 23%, about 24%, about 25%, about 26%, about 27%, about 28%, about 29%, about 30%, about 31%, about 32%, about 33%, about 34%, about 35%, about 36%, about 37%, about 38%, about 39%, about 40%, about 41%, about 42%, about 43%, about 44%, about 45%, about 46%, about 47%, about 48%, about 49%, about 50%, about 51%, about 52%, about 53%, about 54%, about 55%, about 56%, about 57%, about 58%, about 59%, about 60%, about 61%, about 62%, about 63%, about 64%, about 65%, about 66%, about 67%, about 68%, about 69%, about 70%, about 71%, about 72%, about 73%, about 74%, about 75%, about 76%, about 77%, about 78%, about 79%, about 80%, about 81%, about 82%, about 83%, about 84%, about 85%, about 86%, about 87%, about 88%, about 89%, about 90%, about 91%, about 92%, about 93%, about 94%, and about 95%. In some embodiments, the copolymer comprises about 20% to about 80% of a modified protein or of a protein by weight. In some embodiments, the copolymer comprises about 5% to about 35% of a modified protein or of a protein by weight. In some embodiments, the copolymer comprises about 10% to about 20% of a modified protein or of a protein by weight. In some embodiments, the modified protein is a modified whey protein.

In some embodiments of the copolymers disclosed herein, the copolymer comprises a weight percent of a surfactant selected from the group consisting of about 5%, about 6%, about 7%, about 8%, about 9%, about 10%, about 11%, about 12%, about 13%, about 14%, about 15%, about 16%, about 17%, about 18%, about 19%, about 20%, about 21%, about 22%, about 23%, about 24%, about 25%, about 26%, about 27%, about 28%, about 29%, about 30%, about 31%, about 32%, about 33%, about 34%, about 35%, about 36%, about 37%, about 38%, about 39%, about 40%, about 41%, about 42%, about 43%, about 44%, about 45%, about 46%, about 47%, about 48%, about 49%, about 50%, about 51%, about 52%, about 53%, about 54%, about 55%, about 56%, about 57%, about 58%, about 59%, about 60%, about 61%, about 62%, about 63%, about 64%, about 65%, about 66%, about 67%, about 68%, about 69%, about 70%, about 71%, about 72%, about 73%, about 74%, about 75%, about 76%, about 77%, about 78%, about 79%, about 80%, about 81%, about 82%, about 83%, about 84%, about 85%, about 86%, about 87%, about 88%, about 89%, about 90%, about 91%, about 92%, about 93%, about 94%, and about 95%. In some embodiments, the copolymer comprises about 20% to about 80% of a surfactant by weight. In some embodiments, the copolymer comprises about 30% to about 70% of a surfactant by weight. In some embodiments, the copolymer comprises about 15% to about 70% of a surfactant by weight. In some embodiments, the copolymer comprises about 25% to about 45% of a surfactant by weight. In some embodiments, the copolymer comprises about 30% to about 37% of a surfactant by weight. In some embodiments, the surfactant is selected from the group consisting of an ionic surfactant; a surfactant comprising a polymerizable group selected from the group consisting of an acrylate, a siloxane, a glycidyl ether, a vinyl group, and an epoxy group; a non-ionic surfactant; and a zwitterionic surfactant. In some embodiments, the surfactant is an ionic surfactant. In some embodiments, the surfactant is a benzalkonium chloride. In some embodiments of the copolymers disclosed herein, the copolymer comprises a weight percent of a second monomer selected from the group consisting of about 5%, about 6%, about 7%, about 8%, about 9%, about 10%, about 11%, about 12%, about 13%, about 14%, about 15%, about 16%, about 17%, about 18%, about 19%, about 20%, about 21%, about 22%, about 23%, about 24%, about 25%, about 26%, about 27%, about 28%, about 29%, about 30%, about 31%, about 32%, about 33%, about 34%, about 35%, about 36%, about 37%, about 38%, about 39%, about 40%, about 41%, about 42%, about 43%, about 44%, about 45%, about 46%, about 47%, about 48%, about 49%, about 50%, about 51%, about 52%, about 53%, about 54%, about 55%, about 56%, about 57%, about 58%, about 59%, about 60%, about 61%, about 62%, about 63%, about 64%, about 65%, about 66%, about 67%, about 68%, about 69%, about 70%, about 71%, about 72%, about 73%, about 74%, about 75%, about 76%, about 77%, about 78%, about 79%, about 80%, about 81%, about 82%, about 83%, about 84%, about 85%, about 86%, about 87%, about 88%, about 89%, about 90%, about 91%, about 92%, about 93%, about 94%, and about 95%. In some embodiments, the copolymer comprises about 20% to about 80% of a second monomer by weight. In some embodiments, the copolymer comprises about 40% to about 60% of a second monomer by weight. In some embodiments, the second monomer is an acrylate second monomer.

In some embodiments, the copolymer comprises
about 20% to about 80% of a modified protein;
about 20% to about 80% of a surfactant; and
about 20% to about 80% of a second monomer.
In some embodiments, the copolymer comprises
about 20% to about 80% of a modified whey protein;
about 30% to about 70% of a benzalkonium chloride; and
about 20% to about 80% of an acrylate second monomer.
In some embodiments, the copolymer comprises
about 10% to about 20% of a modified protein;
about 30% to about 37% of a surfactant; and
about 40% to about 60% of a second monomer.
In some embodiments, the blend comprises
about 10% to about 20% of a protein;
about 30% to about 37% of a surfactant; and
about 40% to about 60% of a second monomer.

In some embodiments of the methods disclosed herein, polymerization is initiated with heat or irradiation.

In some embodiments of the methods disclosed herein, polymerization is initiated with heat. In some embodiments, a mixture is heated to >75° C. In some embodiments, a mixture is heated to >100° C. In some embodiments, a mixture is heated to >200° C. In some embodiments, a mixture is heated to a temperature selected from the group consisting of about 75° C., about 80° C., about 85° C., about 90° C., about 95° C., about 100° C., about 105° C., about 110° C., about 115° C., about 120° C., about 125° C., about 130° C., about 135° C., about 140° C., about 145° C., about 150° C., about 155° C., about 160° C., about 165° C., about 170° C., about 175° C., about 180° C., about 185° C., about 190° C., about 195° C., about 200° C., about 205° C., about 210° C., about 215° C., about 220° C., about 225° C., about 230° C., about 235° C., about 240° C., about 245° C., about 250° C., about 255° C., about 260° C., about 265° C., about 270° C., about 275° C., about 280° C., about 285° C., about 290° C., about 295° C., about 300° C., about 305° C., about 310° C., about 315° C., about 320° C., about 325° C., about 330° C., about 335° C., about 340° C., about 345° C., and about 350° C. In some embodiments, a mixture is heated to a temperature from about 100° C. to about 275° C. In some embodiments, a mixture is heated to a temperature from about 115° C. to about 135° C. In some embodiments, a mixture is heated to a temperature of about 125° C. In some embodiments, the mixture is used to form a copolymer, a blend, or an article as disclosed above or below.

In some embodiments, of the methods disclosed herein, the mixture further comprises an initiator. In some embodiments, the initiator forms a free radical with heat or irradiation. In some embodiments, the initiator is selected from the group consisting of a peroxide, an aryl ketone, and an azo compound.

In some embodiments, the initiator is an aryl ketone. In some embodiments, the initiator is an azo compound selected from the group consisting of 4,4'-azobis(4-cyanovaleric acid), 4,4'-azobis(4-cyanovaleric acid), 1,1'-azobis(cyclohexanecarbonitrile), 2,2'-azobis(2-methylpropionamidine) dihydrochloride, 2,2'-azobis(2-methylpropionitrile), and 2,2'-azobis(2-methylpropionitrile).

In some embodiments, the initiator is a peroxide selected from the group consisting of ammonium persulfate, potassium persulfate, sodium persulfate, tert-butyl hydroperoxide, tert-butyl peroxyacetate, cumene hydroperoxide, dicumyl peroxide, benzoyl peroxide, tert-amyl peroxide, tert-butyl peroxide, and tert-butyl peroxybenzoate. In some embodiments, the initiator is tert-butyl peroxyacetate. In some embodiments, the initiator is selected from the group consisting of ammonium persulfate, potassium persulfate, and sodium persulfate. In some embodiments, the initiator is ammonium persulfate.

In some embodiments, of the methods disclosed herein, the ratio of the second monomer to the initiator is about 5,000:1 to about 10:1. In some embodiments, the ratio of the second monomer to the initiator is selected from the group consisting of about 5,000:1, about 4,900:1, about 4,800:1, about 4,700:1, about 4,600:1, about 4,500:1, about 4,400:1, about 4,300:1, about 4,200:1, about 4,100:1, about 4,000:1, about 3,900:1, about 3,800:1, about 3,700:1, about 3,600:1, about 3,500:1, about 3,400:1, about 3,300:1, about 3,200:1, about 3,100:1, about 3,000:1, about 2,900:1, about 2,800:1, about 2,700:1, about 2,600:1, about 2,500:1, about 2,400:1, about 2,300:1, about 2,200:1, about 2,100:1, about 2,000:1, about 1,900:1, about 1,800:1, about 1,700:1, about 1,600:1, about 1,500:1, about 1,400:1, about 1,300:1, about 1,200:1, about 1,100:1, about 1,000:1, about 950:1, about 900:1, about 850:1, about 800:1, about 750:1, about 700:1, about 650:1, about 600:1, about 550:1, about 500:1, about 490:1, about 480:1, about 470:1, about 460:1, about 450:1, about 440:1, about 430:1, about 420:1, about 410:1, about 400:1, about 390:1, about 380:1, about 370:1, about 360:1, about 350:1, about 340:1, about 330:1, about 320:1, about 310:1, about 300:1, about 290:1, about 280:1, about 270:1, about 260:1, about 250:1, about 240:1, about 230:1, about 220:1, about 210:1, about 200:1, about 190:1, about 180:1, about 170:1, about 160:1, about 150:1, about 140:1, about 130:1, about 120:1, about 110:1, about 100:1, about 95:1, about 90:1, about 85:1, about 80:1, about 75:1, about 70:1, about 65:1, about 60:1, about 55:1, about 50:1, about 45:1, about 40:1, about 35:1, about 30:1, about 25:1, about 20:1, about 15:1, and about 10:1. In some embodiments, the ratio of the initiator to the second monomer is about 1,000:1 to about 50:1. In some embodiments, the ratio of the initiator to the second monomer is about 500:1 to about 100:1.

In some embodiments, of the methods disclosed herein, the method further comprises providing a catalyst. In some embodiments, the initiator forms a free radical when combined with a catalyst. In some embodiments, the initiator forms a free radical when combined with a catalyst at ambient temperature.

In some embodiments, the catalyst is N,N,N',N'-tetramethylethylene-1,2-diamine (TEMED).

In some embodiments of the copolymers and blends disclosed herein, the ratio of second monomer to catalyst is about 10,000:1 to about 25:1. In some embodiments, the ratio of second monomer to catalyst is selected from the group consisting of about 10,000:1, about 9,900:1, about 9,800:1, about 9,700:1, about 9,600:1, about 9,500:1, about 9,400:1, about 9,300:1, about 9,200:1, about 9,100:1, about 9,000:1, about 8,900:1, about 8,800:1, about 8,700:1, about 8,600:1, about 8,500:1, about 8,400:1, about 8,300:1, about 8,200:1, about 8,100:1, about 8,000:1, about 7,900:1, about 7,800:1, about 7,700:1, about 7,600:1, about 7,500:1, about 7,400:1, about 7,300:1, about 7,200:1, about 7,100:1, about 7,000:1, about 6,900:1, about 6,800:1, about 6,700:1, about 6,600:1, about 6,500:1, about 6,400:1, about 6,300:1, about 6,200:1, about 6,100:1, about 6,000:1, about 5,900:1, about 5,800:1, about 5,700:1, about 5,600:1, about 5,500:1, about 5,400:1, about 5,300:1, about 5,200:1, about 5,100:1, about 5,000:1, about 4,900:1, about 4,800:1, about 4,700:1, about 4,600:1, about 4,500:1, about 4,400:1, about 4,300:1, about 4,200:1, about 4,100:1, about 4,000:1, about 3,900:1, about 3,800:1, about 3,700:1, about 3,600:1, about 3,500:1, about 3,400:1, about 3,300:1, about 3,200:1, about 3,100:1, about 3,000:1, about 2,900:1, about 2,800:1, about 2,700:1, about 2,600:1, about 2,500:1, about 2,400:1, about 2,300:1, about 2,200:1, about 2,100:1, about 2,000:1, about 1,900:1, about 1,800:1, about 1,700:1, about 1,600:1, about 1,500:1, about 1,400:1, about 1,300:1, about 1,200:1, about 1,100:1, about 1,000:1, about 950:1, about 900:1, about 850:1, about 800:1, about 750:1, about 700:1, about 650:1, about 600:1, about 550:1, about 500:1, about 490:1, about 480:1, about 470:1, about 460:1, about 450:1, about 440:1, about 430:1, about 420:1, about 410:1, about 400:1, about 390:1, about 380:1, about 370:1, about 360:1, about 350:1, about 340:1, about 330:1, about 320:1, about 310:1, about 300:1, about 290:1, about 280:1, about 270:1, about 260:1, about 250:1, about 240:1, about 230:1, about 220:1, about 210:1, about 200:1, about 190:1, about 180:1, about 170:1, about 160:1, about 150:1, about 140:1, about 130:1, about 120:1, about 110:1, about 100:1, about 95:1, about 90:1, about 85:1, about 80:1, about 75:1, about 70:1, about 65:1, about 60:1, about 55:1, about 50:1, about 45:1, about 40:1, about 35:1, about 30:1, and about 25:1. In some embodiments, the ratio of second monomer to the catalyst is about 5,000:1 to about 100:1. In some embodiments, the ratio of second monomer to the catalyst is about 1,000:1 to about 200:1.

Physical Properties of Copolymers and Blends

In some embodiments of the copolymers and blends disclosed herein, the elastic modulus (E) of the copolymer at room temperature is greater than about 2 MPa. In some embodiments, the elastic modulus is greater than about 5 MPa. In some embodiments, the elastic modulus is greater than about 15 MPa. In some embodiments, the elastic modulus is about 0.5 MPa to about 250 MPa. In some embodiments, the elastic modulus is selected from the group consisting of about 0.5 MPa, about 1.0 MPa, about 1.5 MPa, about 2.0 MPa, about 2.5 MPa, about 3.0 MPa, about 3.5 MPa, about 4.0 MPa, about 4.5 MPa, about 5.0 MPa, about 5.5 MPa, about 6.0 MPa, about 6.5 MPa, about 7.0 MPa, about 7.5 MPa, about 8.0 MPa, about 8.5 MPa, about 9.0 MPa, about 9.5 MPa, about 10.0 MPa, about 10.5 MPa, about 11.0 MPa, about 11.5 MPa, about 12.0 MPa, about 12.5 MPa, about 13.0 MPa, about 13.5 MPa, about 14.0 MPa, about 14.5 MPa, about 15.0 MPa, about 15.5 MPa, about 16.0 MPa, about 16.5 MPa, about 17.0 MPa, about 17.5 MPa, about 18.0 MPa, about 18.5 MPa, about 19.0 MPa, about 19.5 MPa, about 20.0 MPa, 20.5 MPa, about 21.0 MPa, about 21.5 MPa, about 22.0 MPa, about 22.5 MPa, about 23.0 MPa, about 23.5 MPa, about 24.0 MPa, about 24.5 MPa, about 25.0 MPa, about 25.5 MPa, about 26.0 MPa, about 26.5 MPa, about 27.0 MPa, about 27.5 MPa, about 28.0 MPa, about 28.5 MPa, about 29.0 MPa, about 29.5 MPa, about 30.0 MPa, 30.5 MPa, about 31.0 MPa, about 31.5 MPa, about 32.0 MPa, about 32.5 MPa, about 33.0 MPa, about 33.5 MPa, about 34.0 MPa, about 34.5 MPa, about 35.0 MPa, about 35.5 MPa, about 36.0 MPa, about 36.5 MPa, about 37.0 MPa, about 37.5 MPa, about 38.0 MPa, about 38.5 MPa, about 39.0 MPa, about 39.5 MPa, about 40.0 MPa, 40.5 MPa, about 41.0 MPa, about 41.5 MPa, about 42.0 MPa, about 42.5 MPa, about 43.0 MPa, about 43.5 MPa, about 44.0 MPa, about 44.5 MPa, about 45.0 MPa, about 45.5 MPa, about 46.0 MPa, about 46.5 MPa, about 47.0 MPa, about 47.5 MPa, about 48.0 MPa, about 48.5 MPa, about 49.0 MPa, about 49.5 MPa, about 50.0 MPa, 50.5 MPa, about 51.0 MPa, about 51.5 MPa, about 52.0 MPa, about 52.5 MPa, about 53.0 MPa, about 53.5 MPa, about 54.0 MPa, about 54.5 MPa, about 55.0 MPa, about 55.5 MPa, about 56.0 MPa, about 56.5 MPa, about 57.0 MPa, about 57.5 MPa, about 58.0 MPa, about 58.5 MPa, about 59.0 MPa, about 59.5 MPa, about 60.0 MPa, 60.5 MPa, about 61.0 MPa, about 61.5 MPa, about 62.0 MPa, about 62.5 MPa, about 63.0 MPa, about 63.5 MPa, about 64.0 MPa, about 64.5 MPa, about 65.0 MPa, about 65.5 MPa, about 66.0 MPa, about 66.5 MPa, about 67.0 MPa, about 67.5 MPa, about 68.0 MPa, about 68.5 MPa, about 69.0 MPa, about 69.5 MPa, about 70.0 MPa, 70.5 MPa, about 71.0 MPa, about 71.5 MPa, about 72.0 MPa, about 72.5 MPa, about 73.0 MPa, about 73.5 MPa, about 74.0 MPa, about 74.5 MPa, about 75.0 MPa, about 75.5 MPa, about 76.0 MPa, about 76.5 MPa, about 77.0 MPa, about 77.5 MPa, about 78.0 MPa, about 78.5 MPa, about 79.0 MPa, about 79.5 MPa, about 80.0 MPa, 80.5 MPa, about 81.0 MPa, about 81.5 MPa, about 82.0 MPa, about 82.5 MPa, about 83.0 MPa, about 83.5 MPa, about 84.0 MPa, about 84.5 MPa, about 85.0 MPa, about 85.5 MPa, about 86.0 MPa, about 86.5 MPa, about 87.0 MPa, about 87.5 MPa, about 88.0 MPa, about 88.5 MPa, about 89.0 MPa, about 89.5 MPa, about 90.0 MPa, 90.5 MPa, about 91.0 MPa, about 91.5 MPa, about 92.0 MPa, about 92.5 MPa, about 93.0 MPa, about 93.5 MPa, about 94.0 MPa, about 94.5 MPa, about 95.0 MPa, about 95.5 MPa, about 96.0 MPa, about 96.5 MPa, about 97.0 MPa, about 97.5 MPa, about 98.0 MPa, about 98.5 MPa, about 99.0 MPa, about 99.5 MPa, about 100.0 MPa, 100.5 MPa, about 101.0 MPa, about 101.5 MPa, about 102.0 MPa, about 102.5 MPa, about 103.0 MPa, about 103.5 MPa, about 104.0 MPa, about 104.5 MPa, about 105.0 MPa, about 105.5 MPa, about 106.0 MPa, about 106.5 MPa, about 107.0 MPa, about 107.5 MPa, about 108.0 MPa, about 108.5 MPa, about 109.0 MPa, about 109.5 MPa, about 110.0 MPa, 110.5 MPa, about 111.0 MPa, about 111.5 MPa, about 112.0 MPa, about 112.5 MPa, about 113.0 MPa, about 113.5 MPa, about 114.0 MPa, about 114.5 MPa, about 115.0 MPa, about 115.5 MPa, about 116.0 MPa, about 116.5 MPa, about 117.0 MPa, about 117.5 MPa, about 118.0 MPa, about 118.5 MPa, about 119.0 MPa, about 119.5 MPa, about 120.0 MPa, 120.5 MPa, about 121.0 MPa, about 121.5 MPa, about 122.0 MPa, about 122.5 MPa, about 123.0 MPa, about 123.5 MPa, about 124.0 MPa, about 124.5 MPa, about 125.0 MPa, about 125.5 MPa, about 126.0 MPa, about 126.5 MPa, about 127.0 MPa, about 127.5 MPa, about 128.0 MPa, about 128.5 MPa, about 129.0 MPa, about 129.5 MPa, about 130.0 MPa, 130.5 MPa, about 131.0 MPa, about 131.5 MPa, about 132.0 MPa, about 132.5 MPa, about 133.0 MPa, about 133.5 MPa, about 134.0 MPa, about 134.5 MPa, about 135.0 MPa, about 135.5 MPa, about 136.0 MPa, about 136.5 MPa, about 137.0 MPa, about 137.5 MPa, about 138.0 MPa, about 138.5 MPa, about 139.0 MPa, about 139.5 MPa, about 140.0 MPa, 140.5 MPa, about 141.0 MPa, about 141.5 MPa, about 142.0 MPa, about 142.5 MPa, about 143.0 MPa, about 143.5 MPa, about 144.0 MPa, about 144.5 MPa, about 145.0 MPa, about 145.5 MPa, about 146.0 MPa, about 146.5 MPa, about 147.0 MPa, about 147.5 MPa, about 148.0 MPa, about 148.5 MPa, about 149.0 MPa, about 149.5 MPa, about 150.0 MPa, about 151 MPa, about 152 MPa, about 153 MPa, about 154 MPa, about 155 MPa, about 156 MPa, about 157 MPa, about 158 MPa, about 159 MPa, about 160 MPa, about 161 MPa, about 162 MPa, about 163 MPa, about 164 MPa, about 165 MPa, about 166 MPa, about 167 MPa, about 168 MPa, about 169 MPa, about 170 MPa, about 171 MPa, about 172 MPa, about 173 MPa, about 174 MPa, about 175 MPa, about 176 MPa, about 177 MPa, about 178 MPa, about 179 MPa, about 180 MPa, about 181 MPa, about 182 MPa, about 183 MPa, about 184 MPa, about 185 MPa, about 186 MPa, about 187 MPa, about 188 MPa, about 189 MPa, about 190 MPa, about 191 MPa, about 192 MPa, about 193 MPa, about 194 MPa, about 195 MPa, about 196 MPa, about 197 MPa, about 198 MPa, about 199 MPa, about 200 MPa, about 205 MPa, about 210 MPa, about 215 MPa, about 220 MPa, about 225 MPa, about 230 MPa, about 235 MPa, about 240 MPa, about 245 MPa, and about 250 MPa. In some embodiments, the elastic modulus is about 0.5 MPa to about 225 MPa. In some embodiments, the elastic modulus is about 0.5 MPa to about 200 MPa. In some embodiments, the elastic modulus is about 0.5 MPa to about 100 MPa. In some embodiments, the elastic modulus is about 0.5 MPa to about 75 MPa. In some embodiments, the elastic modulus is about 1 MPa to about 65 MPa. In some embodiments, the elastic modulus is about 6 MPa to about 15 MPa.

In some embodiments, the elastic modulus is measured at about 0% relative humidity (RH), about 1% RH, about 2% RH, about 3% RH, about 4% RH, about 5% RH, about 6% RH, about 7% RH, about 8% RH, about 9% RH, about 10% RH, about 15% RH, about 20% RH, about 25% RH, about 30% RH, about 35% RH, about 40% RH, about 45% RH, about 50% RH, about 55% RH, about 60% RH, about 65% RH, about 70% RH, about 75% RH, about 80% RH, about 85% RH, about 90% RH, about 95% RH, about 96% RH, about 97% RH, about 98% RH, or about 99% RH.

In some embodiments, the elastic modulus is measured at about 4% RH, about 10% RH, about 15% RH, about 20% RH, about 25% RH, about 30% RH, about 35% RH, about 50% RH, or about 80% RH. In some embodiments, the elastic modulus is measured at about 10% RH, about 15% RH, about 20% RH, about 25% RH, or about 30% RH. In some embodiments, the elastic modulus is measured at about 20% RH. In some embodiments, at about 20% RH, the elastic modulus is greater than 50 MPa. In some embodiments, at about 60% RH, the elastic modulus is about 5 MPa to about 75 MPa.

In some embodiments, the elastic modulus is measured at about 40% RH, about 45% RH, about 50% RH, about 55% RH, or about 60% RH. In some embodiments, the elastic modulus is measured at about 50% RH. In some embodiments, at about 50% RH, the elastic modulus is greater than 3 MPa. In some embodiments, at about 50% RH, the elastic modulus is about 1 MPa to about 10 MPa.

In some embodiments, the water content of the polymer is from about 0.1% to about 6% by weight. In some embodiments, the water content of the polymer is about 0.1%, about 0.2%, about 0.3%, about 0.4%, about 0.5%, about 0.6%, about 0.7%, about 0.8%, about 0.9%, about 1.0%, about 1.1%, about 1.2%, about 1.3%, about 1.4%, about 1.5%, about 1.6%, about 1.7%, about 1.8%, about 1.9%, about 2.0%, about 2.1%, about 2.2%, about 2.3%, about 2.4%, about 2.5%, about 2.6%, about 2.7%, about 2.8%, about 2.9%, about 3.0%, about 3.1%, about 3.2%, about 3.3%, about 3.4%, about 3.5%, about 3.6%, about 3.7%, about 3.8%, about 3.9%, about 4.0%, about 4.1%, about 4.2%, about 4.3%, about 4.4%, about 4.5%, about 4.6%, about 4.7%, about 4.8%, about 4.9%, about 5.0%, about 5.1%, about 5.2%, about 5.3%, about 5.4%, about 5.5%, about 5.6%, about 5.7%, about 5.8%, about 5.9%, about 6.0%, about 6.1%, about 6.2%, about 6.3%, about 6.4%, about 6.5%, about 6.6%, about 6.7%, about 6.8%, about 6.9%, about 7.0%, about 7.1%, about 7.2%, about 7.3%, about 7.4%, about 7.5%, about 7.6%, about 7.7%, about 7.8%, about 7.9%, about 8.0%, about 7.1%, about 7.2%, about 7.3%, about 7.4%, about 7.5%, about 7.6%, about 7.7%, about 7.8%, about 7.9%, about 8.0%, about 8.1%, about 8.2%, about 8.3%, about 8.4%, about 8.5%, about 8.6%, about 8.7%, about 8.8%, about 8.9%, about 9.0%, about 9.1%, about 9.2%, about 9.3%, about 9.4%, about 9.5%, about 9.6%, about 9.7%, about 9.8%, about 9.9%, about 10.0%, about 10.1%, about 10.2%, about 10.3%, about 10.4%, about 10.5%, about 10.6%, about 10.7%, about 10.8%, about 10.9%, about 11.0%, about 11.1%, about 11.2%, about 11.3%, about 11.4%, about 11.5%, about 11.6%, about 11.7%, about 11.8%, about 11.9%, about 12.0%, about 12.1%, about 12.2%, about 12.3%, about 12.4%, about 12.5%, about 12.6%, about 12.7%, about 12.8%, about 12.9%, about 13.0%, about 13.1%, about 13.2%, about 13.3%, about 13.4%, about 13.5%, about 13.6%, about 13.7%, about 13.8%, about 13.9%, about 14.0%, about 14.1%, about 14.2%, about 14.3%, about 14.4%, about 14.5%, about 14.6%, about 14:7%, about 14.8%, about 14.9%, about 15.0%, about 15.1%, about 15.2%, about 15.3%, about 15.4%, about 15.5%, about 15.6%, about 15.7%, about 15.8%, about 15.9%, about 16.0% by weight. In some embodiments, the water content of the polymer is from about 0.5% to about 14% by weight.

In some embodiments, the water content of the polymer is from about 0.5% to about 9% by weight. In some embodiments, the water content of the polymer is from about 1% to about 7.5% by weight. In some embodiments, the water content of the polymer is from about 2% to about 5% by weight. In some embodiments, the water content of the polymer is measured at about 50% RH.

In some embodiments, the elastic modulus is measured at about 80% RH, about 85% RH, about 90% RH, about 95% RH, about 96% RH, about 97% RH, about 98% RH, or about 99% RH. In some embodiments, the elastic modulus is measured at about 90% RH. In some embodiments, at about 90% RH, the elastic modulus is greater than 1 MPa. In some embodiments, at about 90% RH, the elastic modulus is about 0.5 MPa to about 9 MPa.

In some embodiments of the copolymers disclosed herein, tensile strength of the copolymer at room temperature is about 1 MPa to about 25 MPa. In some embodiments, the tensile strength is about 2 MPa to about 15 MPa. In some embodiments, the tensile strength is selected from the group consisting of about 2.0 MPa, about 2.5 MPa, about 3.0 MPa, about 3.1 MPa, about 3.2 MPa, about 3.3 MPa, about 3.4 MPa, about 3.5 MPa, about 3.6 MPa, about 3.7 MPa, about 3.8 MPa, about 3.9 MPa, about 4.0 MPa, about 4.1 MPa, 4.2 MPa, about 4.3 MPa, about 4.4 MPa, about 4.5 MPa, about 4.6 MPa, about 4.7 MPa, about 4.8 MPa, about 4.9 MPa, about 5.0 MPa, about 5.1 MPa, about 5.2 MPa, about 5.3 MPa, about 5.4 MPa, about 5.5 MPa, about 5.6 MPa, about 5.7 MPa, about 5.8 MPa, about 5.9 MPa, about 6.0 MPa, about 6.1 MPa, about 6.2 MPa, about 6.3 MPa, about 6.4

MPa, about 6.5 MPa, about 6.6 MPa, about 6.7 MPa, about 6.8 MPa, about 6.9 MPa, about 7.0 MPa, about 7.1 MPa, about 7.2 MPa, about 7.3 MPa, about 7.4 MPa, about 7.5 MPa, about 7.6 MPa, about 7.7 MPa, about 7.8 MPa, about 7.9 MPa, about 8.0 MPa, about 8.1 MPa, about 8.2 MPa, about 8.3 MPa, about 8.4 MPa, about 8.5 MPa, about 8.6 MPa, about 8.7 MPa, about 8.8 MPa, about 8.9 MPa, about 9.0 MPa, about 9.1 MPa, about 9.2 MPa, about 9.3 MPa, about 9.4 MPa, about 9.5 MPa, about 9.6 MPa, about 9.7 MPa, about 9.8 MPa, about 9.9 MPa, about 10.0 MPa, about 10.1 MPa, about 10.2 MPa, about 10.3 MPa, about 10.4 MPa, about 10.5 MPa, about 10.6 MPa, about 10.7 MPa, about 10.8 MPa, about 10.9 MPa, about 11.0 MPa, about 11.1 MPa, about 11.2 MPa, about 11.3 MPa, about 11.4 MPa, about 11.5 MPa, about 11.6 MPa, about 11.7 MPa, about 11.8 MPa, about 11.9 MPa, about 12.0 MPa, about 12.1 MPa, about 12.2 MPa, about 12.3 MPa, about 12.4 MPa, about 12.5 MPa, about 12.6 MPa, about 12.7 MPa, about 12.8 MPa, about 12.9 MPa, about 13.0 MPa, about 13.1 MPa, about 13.2 MPa, about 13.3 MPa, about 13.4 MPa, about 13.5 MPa, about 13.6 MPa, about 13.7 MPa, about 13.8 MPa, about 13.9 MPa, about 14.0 MPa, about 14.1 MPa, about 14.2 MPa, about 14.3 MPa, about 14.4 MPa, about 14.5 MPa, about 14.6 MPa, about 14.7 MPa, about 14.8 MPa, about 14.9 MPa, and about 15.0 MPa. In some embodiments, the tensile strength is about 1 MPa to about 6 MPa.

In some embodiments of the copolymers disclosed herein, toughness of the copolymer at room temperature is about 0.1 $MJ/m^3$ to about 45 $MJ/m^3$. In some embodiments, the toughness is about 0.1 $MJ/m^3$ to about 35 $MJ/m^3$. In some embodiments, the toughness is selected from the group consisting of about 0.1 $MJ/m^3$, about 0.2 $MJ/m^3$, about 0.3 $MJ/m^3$, about 0.4 $MJ/m^3$, about 0.5 $MJ/m^3$, about 0.6 $MJ/m^3$, about 0.7 $MJ/m^3$, about 0.8 $MJ/m^3$, about 0.9 $MJ/m^3$, about 1.0 $MJ/m^3$, about 1.5 $MJ/m^3$, about 2.0 $MJ/m^3$, about 2.5 $MJ/m^3$, about 3.0 $MJ/m^3$, about 3.5 $MJ/m^3$, about 4.0 $MJ/m^3$, about 4.5 $MJ/m^3$, about 5.0 $MJ/m^3$, about 5.5 $MJ/m^3$, about 6.0 $MJ/m^3$, about 6.5 $MJ/m^3$, about 7.0 $MJ/m^3$, about 7.5 $MJ/m^3$, about 8.0 $MJ/m^3$, about 8.5 $MJ/m^3$, about 9.0 $MJ/m^3$, about 9.5 $MJ/m^3$, about 10.0 $MJ/m^3$, about 10.5 $MJ/m^3$, about 11.0 $MJ/m^3$, about 11.5 $MJ/m^3$, about 12.0 $MJ/m^3$, about 12.5 $MJ/m^3$, about 13.0 $MJ/m^3$, about 13.5 $MJ/m^3$, about 14.0 $MJ/m^3$, about 14.5 $MJ/m^3$, about 15.0 $MJ/m^3$, about 15.5 $MJ/m^3$, about 16.0 $MJ/m^3$, about 16.5 $MJ/m^3$, about 17.0 $MJ/m^3$, about 17.5 $MJ/m^3$, about 18.0 $MJ/m^3$, about 18.5 $MJ/m^3$, about 19.0 $MJ/m^3$, about 19.5 $MJ/m^3$, about 20.0 $MJ/m^3$, about 20.5 $MJ/m^3$, about 21.0 $MJ/m^3$, about 21.5 $MJ/m^3$, about 22.0 $MJ/m^3$, about 22.5 $MJ/m^3$, about 23.0 $MJ/m^3$, about 23.5 $MJ/m^3$, about 24.0 $MJ/m^3$, about 24.5 $MJ/m^3$, about 25.0 $MJ/m^3$, about 25.5 $MJ/m^3$, about 26.0 $MJ/m^3$, about 26.5 $MJ/m^3$, about 27.0 $MJ/m^3$, about 27.5 $MJ/m^3$, about 28.0 $MJ/m^3$, about 28.5 $MJ/m^3$, about 29.0 $MJ/m^3$, about 29.5 $MJ/m^3$, about 30.0 $MJ/m^3$, about 30.5 $MJ/m^3$, about 31.0 $MJ/m^3$, about 31.5 $MJ/m^3$, about 32.0 $MJ/m^3$, about 32.5 $MJ/m^3$, about 33.0 $MJ/m^3$, about 33.5 $MJ/m^3$, about 34.0 $MJ/m^3$, about 34.5 $MJ/m^3$, and about 35.0 $MJ/m^3$. In some embodiments, the toughness is about 0.1 $MJ/m^3$ to about 10 $MJ/m^3$.

In some embodiments, the copolymer comprises phase separated domains. In some embodiments, the copolymer comprises microphase separated hard domains. In some embodiments, the copolymer further comprises microphase separated soft domains.

In some embodiments, the copolymer is an elastomer.
In some embodiments, the copolymer is a hard plastic.
In some embodiments, the copolymer is a soft plastic.
In some embodiments, the copolymer is crosslinked.
In some embodiments, the copolymer exhibits long-range order.
In some embodiments, the copolymer is a thermoset plastic.

Exemplary Compositions

In some embodiments, the disclosure relates to a composition, comprising a copolymer disclosed herein, and a solvent.

In some embodiments, the disclosure relates to a composition, comprising a blend disclosed herein, and a solvent.

In some embodiments, the solvent is selected from the group consisting of 1-ethyl-3-methylimidazolium diethyphosphate, isopropanol, ethanol, water, and mixtures thereof. In some embodiments, the solvent comprises water.

In some embodiments, the composition is a liquid at a temperature greater than about 25° C.

In some embodiments, the composition has a melting point less than about 25° C.

Exemplary Articles

In another aspect, the disclosure relates to an article comprising a copolymer disclosed herein.

In some embodiments, an article is formed using a method of making a copolymer, comprising the steps of:
 a) combining a first monomer, a surfactant, and a second monomer, thereby forming a first mixture;
 b) heating the first mixture;
 c) initiating polymerization of the first mixture, thereby forming an article comprising a copolymer comprising
  (i) a plurality of a first monomer, wherein the first monomer is a modified protein comprising a protein and at least one functional group selected from the group consisting of an acrylate, a siloxane, a glycidyl ether, a vinyl group, an epoxy group, and a maleimide group;
  (ii) a plurality of a surfactant; and
  (iii) a plurality of a second monomer, wherein the second monomer is selected from the group consisting of an acrylate, a siloxane, a glycidyl ether, a monomer comprising a vinyl group, a monomer comprising an epoxy group, and a monomer comprising a maleimide group.

In some embodiments, an article is formed using a method of making a copolymer, comprising the steps of:
 a) combining a first monomer, a surfactant, and a second monomer, thereby forming a first mixture;
 b) heating the first mixture;
 c) combining the first mixture with an initiator, thereby forming a second mixture;
 d) initiating polymerization of the second mixture, thereby forming an article comprising a copolymer comprising
  (i) a plurality of a first monomer, wherein the first monomer is a modified protein comprising a protein and at least one functional group selected from the group consisting of an acrylate, a siloxane, a glycidyl ether, a vinyl group, an epoxy group, and a maleimide group;
  (ii) a plurality of a surfactant; and
  (iii) a plurality of a second monomer, wherein the second monomer is selected from the group consisting of an acrylate, a siloxane, a glycidyl ether, a monomer comprising a vinyl group, a monomer comprising an epoxy group, and a monomer comprising a maleimide group.

In another aspect, the disclosure relates to an article comprising a blend disclosed herein.

In some embodiments, an article is formed using a method of making a blend, comprising the steps of:
a) combining a protein, a surfactant, and a second monomer, thereby forming a first mixture;
b) heating the first mixture;
c) initiating polymerization of the first mixture, thereby forming an article comprising a blend comprising
   (i) a plurality of a protein;
   (ii) a plurality of a surfactant; and
   (iii) a plurality of a second monomer, wherein the second monomer is selected from the group consisting of an acrylate, a siloxane, a glycidyl ether, a monomer comprising a vinyl group, a monomer comprising an epoxy group, and a monomer comprising a maleimide group.

In some embodiments, an article is formed using a method of making a blend, comprising the steps of:
a) combining a protein, a surfactant, and a second monomer, thereby forming a first mixture;
b) heating the first mixture;
c) combining the first mixture with an initiator, thereby forming a second mixture;
d) initiating polymerization of the second mixture, thereby forming an article comprising a blend comprising
   (i) a plurality of a protein;
   (ii) a plurality of a surfactant; and
   (iii) a plurality of a second monomer, wherein the second monomer is selected from the group consisting of an acrylate, a siloxane, a glycidyl ether, a monomer comprising a vinyl group, a monomer comprising an epoxy group, and a monomer comprising a maleimide group.

In some embodiments, the first mixture is heated at a temperature >100° C.

In some embodiments, the second mixture is heated at a temperature >100° C. In some embodiments, the second mixture is heated at a temperature of 125° C.

In some embodiments, the polymerization is in a compression mold.

In some embodiments, the article is manufactured using compression molding. In some embodiments, the article is manufactured using injection molding.

EXEMPLIFICATION

The invention now being generally described, it will be more readily understood by reference to the following, which is included merely for purposes of illustration of certain aspects and embodiments of the present invention, and is not intended to limit the invention.

Example 1—Preparing Protein Monomers

A. Materials and Methods.

Poly(ethylene glycol) methyl ether methacrylate (PEGMA, average $M_n$=500 g mol$^{-1}$ or average $M_n$=480 g mol$^{-1}$), hydroxypropyl acrylate (HPA), poly(ethylene glycol) diacrylate (PEGDA, average $M_n$=700 g mol$^{-1}$), methacrylic anhydride, β-lactoglobulin (>95% purity), tetramethylethylenediamine (TEMED), n-butyl acrylate, and azobisisobutyronitrile were purchased from Sigma Aldrich. Ammonium persulfate was purchased from Mallinckrodt Chemicals, while Whey Protein Isolate was purchased from Bipro USA. Butanediol diacrylate and methacrylic anhydride were purchased from Alfa Aesar. Tert-butyl peroxyacetate, and benzalkonium chloride were purchased from Acros Organics and MP Biomedicals, respectively.

B. β-lactoglobulin Purification.

β-lactoglobulin for material synthesis was purified from whey protein isolate via selective pepsin hydrolyzation using a procedure adapted from Naofumi et al[38]. Whey protein isolate was dissolved in water at 20 wt. % protein concentration, and the pH was adjusted to 2 using hydrochloric acid. Pepsin was added at 1 wt. % concentration, and the mixture was incubated at 37° C. overnight. Low molecular weight hydrolysates and impurities were removed through dialysis, and dry β-lactoglobulin was obtained after lyophilization.

C. Methacrylated Protein Synthesis.

To prepare covalently bonded copolymers of the protein and the polyacrylate, amine groups on the protein were reacted with methacrylic anhydride (FIG. 1). Proteins modified to have more than one methacrylamide group can be conjugated to more than one growing polyacrylate chain, and therefore serve as macrocrosslinkers that produce crosslinked networks reinforced by stiff protein domains. On the other hand, polymerization with unmodified proteins results in uncrosslinked blends, where the proteins function only as filler.

Whey protein isolate was chosen as the model crude protein mixture as it is a well-studied, widely available by-product in the dairy industry. Its primary component, β-lactoglobulin, can be easily purified for studies on the effects of feedstock diversity. Polymerizable whey protein and β-lactoglobulin were prepared through an amine-based reaction with methacrylic anhydride to introduce (meth)acryloyl moieties onto biomass-derived proteins (FIG. 1). The presence of methacrylate groups on proteins forms a macromonomer that is reactive in the subsequent free-radical polymerization step and allows for greater control over chemical crosslink density. Under basic conditions, exposed lysine side chains and the protein N-termini are available to react with the anhydride, and the level of methacrylation is varied by changing the amount of anhydride added. Methacrylic acid, a by-product of the amine-anhydride reaction, is not removed from the protein solution as it is polymerizable and has no adverse impact if incorporated into the final material. This eliminates the need for an intermediate purification step.

Figure 2A:
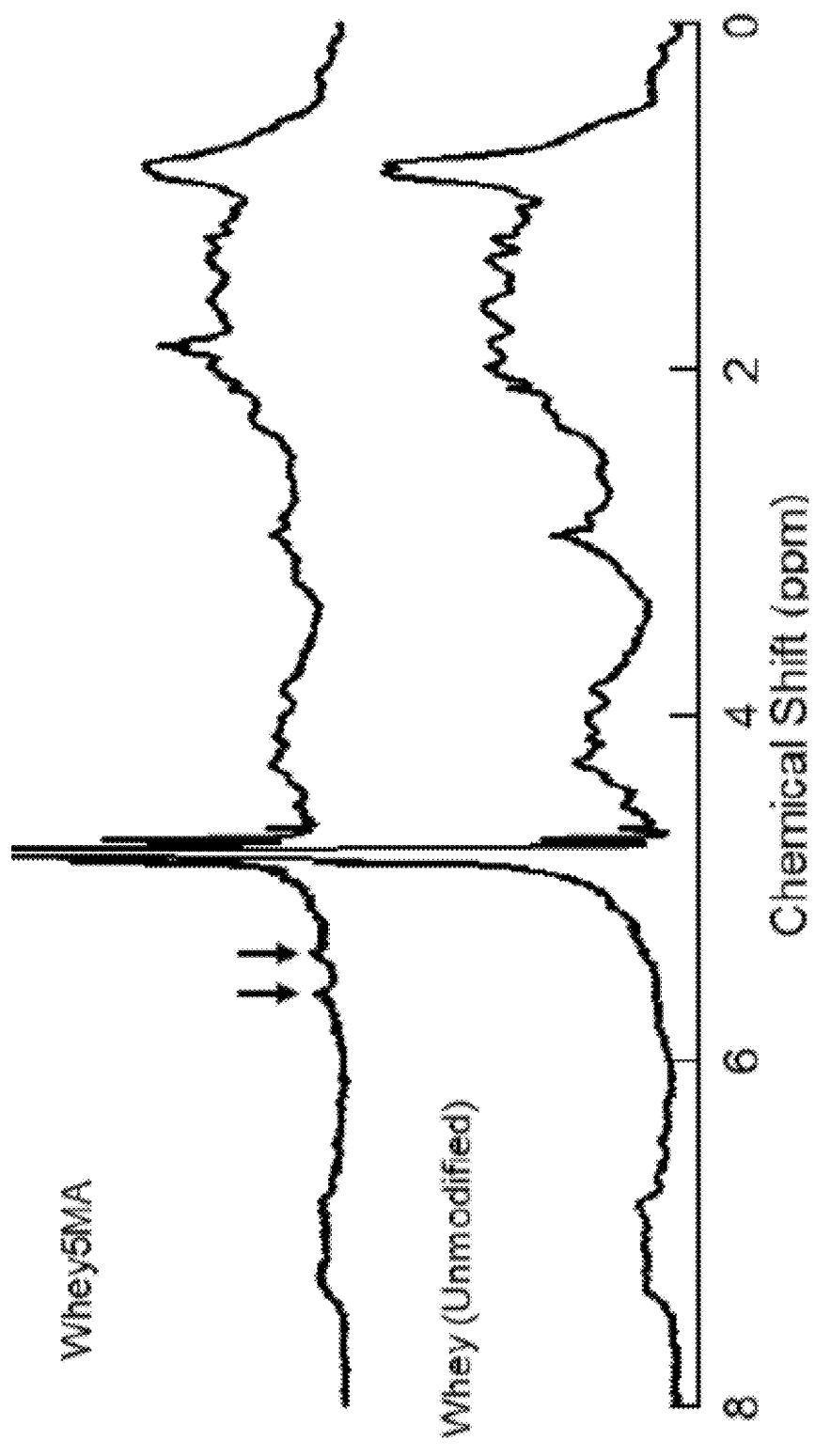
FIG. 2A depicts proton NMR of an exemplary modified protein compared to an unmodified protein.

Proteins were functionalized with methacrylate groups using an anhydride-amine reaction. A 10 wt. % protein solution was prepared in water, and the pH was adjusted to 10-11 using sodium hydroxide. Methacrylic anhydride was added to the protein solution while stirring at anhydride to protein mole ratios of 1.2 to 6, calculated using the molecular weight of β-lactoglobulin. The reaction was carried out overnight under ambient conditions, and the reaction products in solution were used in subsequent polymerization reactions without purification. The nomenclature for modified proteins is defined as follows: Protein-X-MA, where 'Protein' is either whey or BLG (β-lactoglobulin), and 'X' is the mole ratio of methacrylic anhydride to protein, calculated as if the protein is pure p-lactoglobulin. The materials are made up of 20 wt. % protein that were modified at a methacrylic anhydride to protein mole ratio of 1:1.2. Proton NMR spectra of modified whey protein compared to unmodified whey protein are shown in FIG. 2A.

D. Estimating the Degree of Methacrylation.

Figure 2B:
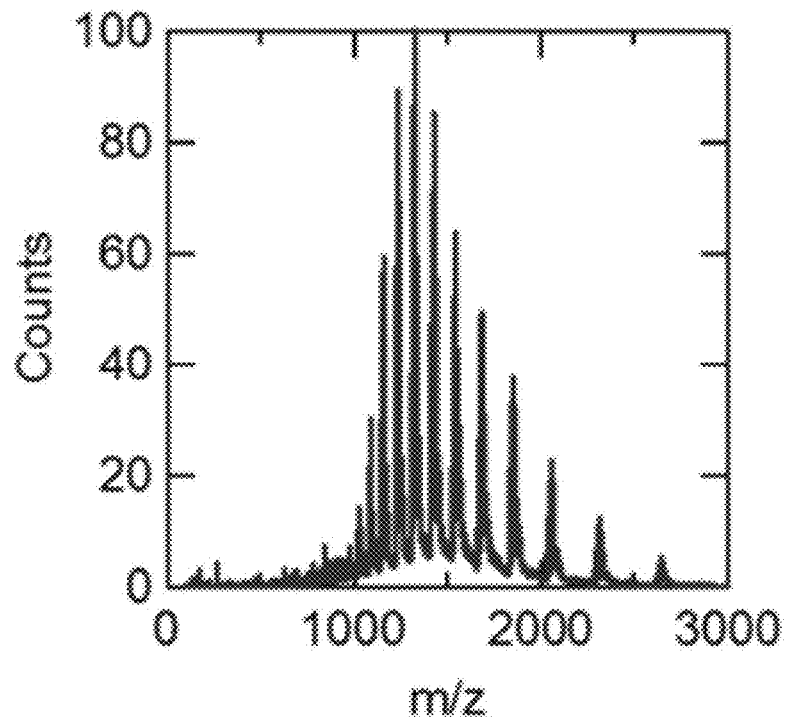
FIG. 2B depicts a representative mass spectrometry signal of modified 3-lactoglobulin before deconvolution.
Figure 2C:
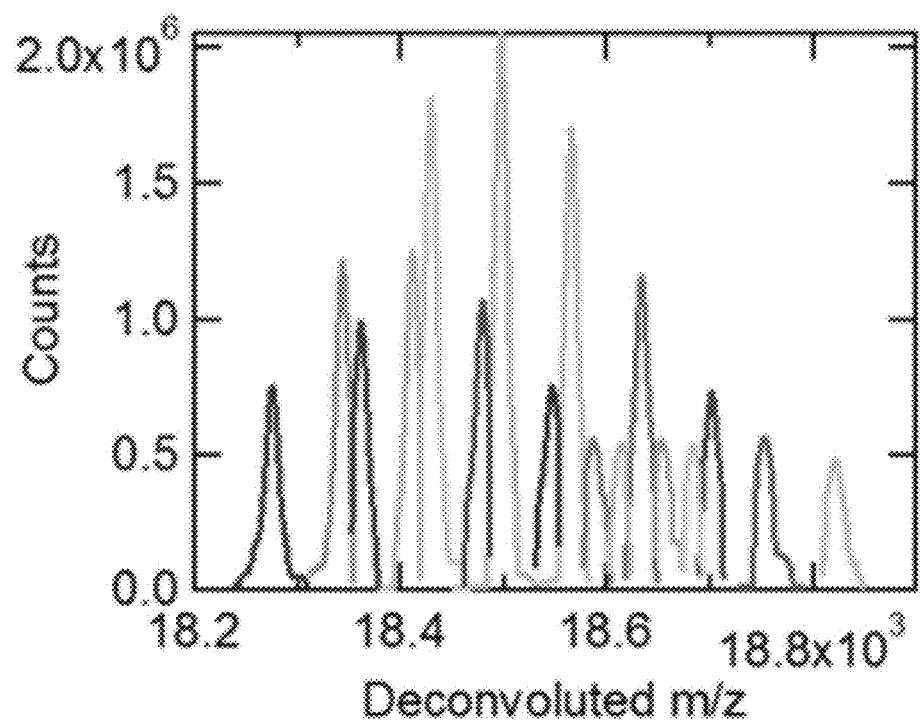
FIG. 2C depicts representative mass spectrometry signals of modified 3-lactoglobulin after deconvolution.
Figure 2D:
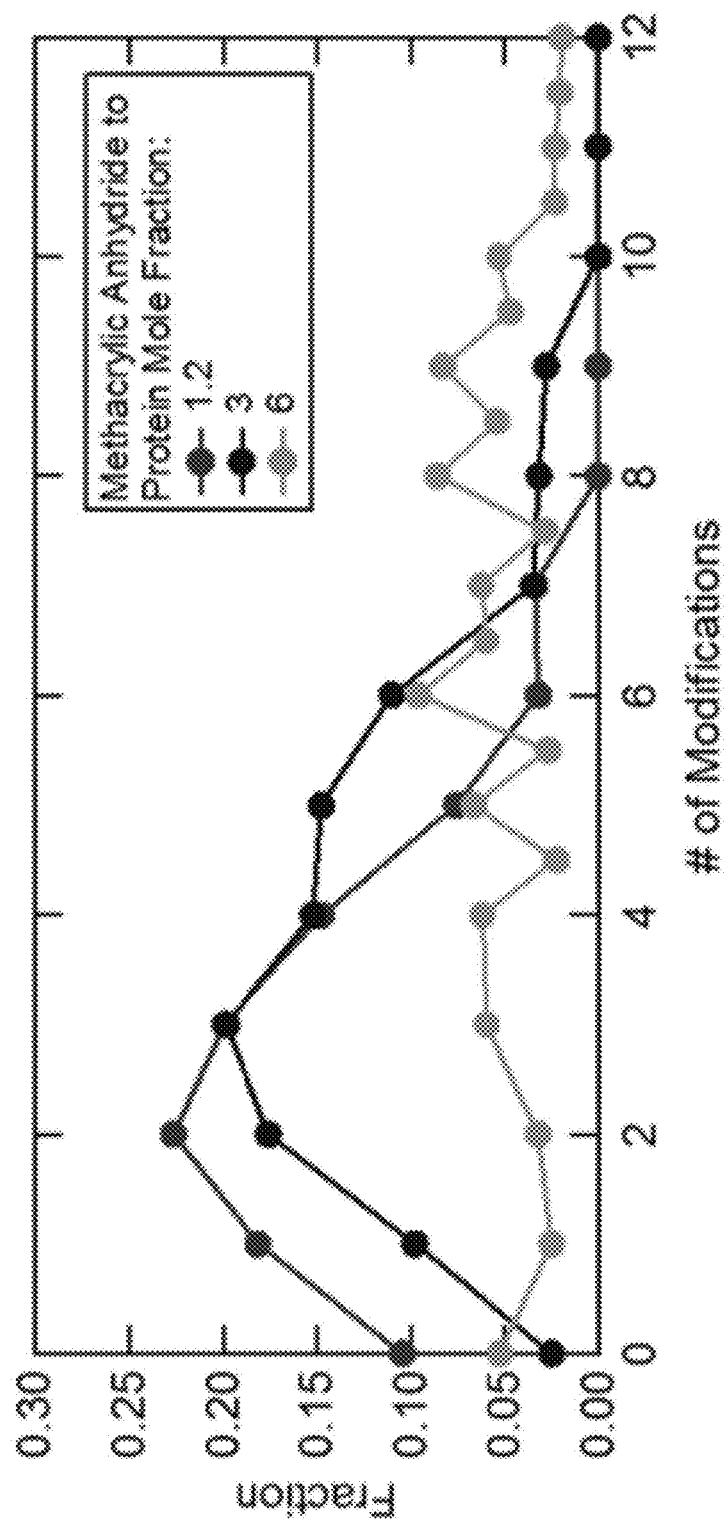
FIG. 2D depicts the distribution of protein methacrylation levels at various methacrylic anhydride to protein mole fractions.

Protein methacrylation, a variable to control chemical crosslink density and material properties, was quantified using model reactions with pure β-lactoglobulin (>95% purity) as the protein reactant. β-Lactoglobulin is the main protein component (approximately 65 wt. %[37]) in whey protein and therefore provides a simple, single-protein approximation for studying the reactivity in whey, which is a complex mixture. Molecular weight quantification on the reaction products was performed using LC-MS, where the raw charge ladder data was deconvoluted using the instrument software (FIGS. 2B and 2C), compared to the unmodified protein, and matched with the number of methacrylic group additions (+68 Da). Relative abundance of the different molecular species obtained from these calculations was used to determine the distribution of modifications (FIG. 2D), which is broad due to the large number of 6-amino group of lysine residues available for the reaction and the non-site-specific nature of the reaction. Methacrylate groups on the proteins and methacrylic acid side products may undergo Michael addition with both primary and secondary amines[38]. Side reactions with methacrylic acid can lead to formation of unpolymerizable amine-methacrylate adducts that increase molecular weights of proteins, and may have contributed to the >100% yields observed. This is less prominent at higher methacrylation levels, as the generation of acid lowers the pH and protonates amines. Similar reactions may also occur with methacrylate groups on proteins, which result in covalent bond formation between two proteins, where the molar mass of the protein complex is a multiple of the unmodified protein molar mass plus the contributions from all modification sites. On the deconvoluted mass spectra, the protein complex is indistinguishable from the monomeric modified protein, unless the number of modifications is not an integer multiple of the number of bridged proteins. Therefore, this side reaction can contribute to peaks corresponding to non-integer number of modifications, as observed in the reaction at the highest methacrylation level (FIG. 2C). The extent of this side reaction is smaller at lower methacrylation levels, as indicated by the absence of non-integer modification sites, and may even be small in general due to steric hindrance. Molecular weights of all reaction products obtained from deconvolution were used to determine number of methacrylate groups on the proteins. The average number of modifications was determined to be 2.6, 3.8, and 6.5 for the three methacrylation levels, methacrylic anhydride to protein mole fractions of 1.2, 3 and 6, respectively.

The degree of methacrylation was estimated using a model methacrylation reaction on pure β-lactoglobulin (>95% purity) and analyzed using liquid chromatography-mass spectrometry (LC-MS) analysis with spectral deconvolution. LC-MS was carried out on an Agilent Poroshell 300SB-C18 column operating at a flow rate of 0.55 mL/min, with water as the running buffer (A) and acetonitrile as the elution buffer (B). The elution gradient was as follows: 0 min, 5% B; 5.2 min, 95% B; 6 min, 95% B; 6.4 min, 95% B; 8 min, 95% B. MS detection was carried out on an Agilent 6100 Single Quadrupole with m/z ranges of 150 to 850 to obtain molecular weights of the reaction product. Degree of methacrylation shown in FIG. 2C was calculated from the deconvolution of the mass spectra with limits for low molecular weight, high molecular weight, and maximum charge set at 18,000 Da, 19,500 Da, and 20 respectively. Reaction products with abundance of 20% or lower (when compared to the most abundant species) were not included in the results.

Example 2—Copolymer Preparation

Figure 3A:
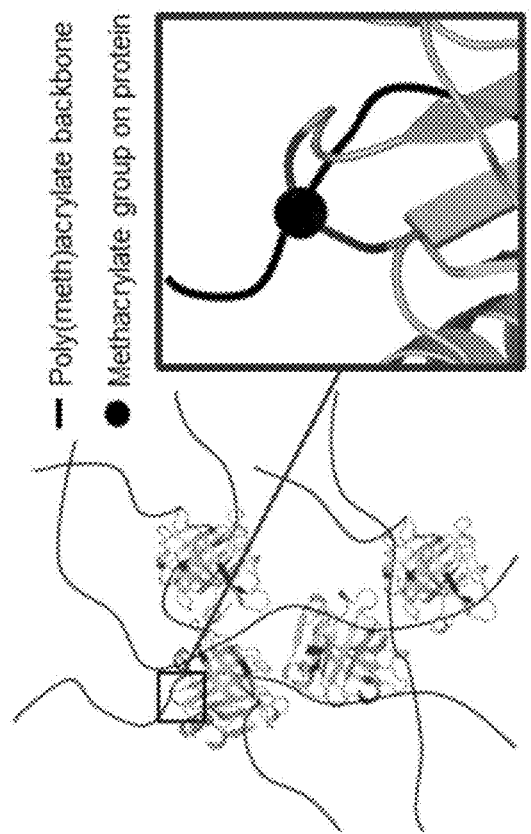
FIG. 3A is a schematic representation of preparing an exemplary copolymer described herein comprising a modified protein monomer and a second monomer.
Figure 3A:
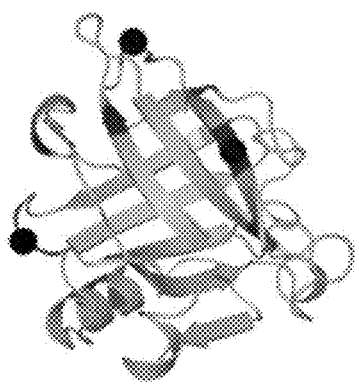

A. Protein-Surfactant Complexes. Protein-surfactant complex was prepared by dissolving whey protein isolate modified with methacrylic anhydride and benzalkonium chloride in water at 1:1 mass ratio and lyophilized. The protein contains methacrylamide groups that allow it to function as a crosslinker when cured (FIG. 3A).

Alternatively, protein-surfactant complexes were prepared by dissolving proteins in water to make 10% w/w protein solutions, followed by addition of benzalkonium chloride. The mixtures were stirred until homogeneous and lyophilized. Complexes with polymerizable proteins were also prepared in a similar manner. Proteins dissolved in aqueous solutions and modified with methacrylic anhydride, as described in Example 1, were mixed with benzalkonium chloride without intermediate purification steps.

B. Protein-Surfactant-Acrylate Copolymers.

A protein-based copolymer was prepared with a non-water soluble monomer, which is expected to reduce the material's overall moisture sensitivity. The monomer n-butyl acrylate (n-BA) was selected due to its low polarity, negligible water absorption and low homopolymer glass transition temperature. By conjugating stiff proteins to rubbery polymer segments, combined advantages of both components in terms of high strength and toughness have been demonstrated in protein-based elastomers. See, for example, FIGS. 4A and 4B. However, copolymerization strategies are usually applied to both water soluble proteins and monomers, or proteins that are directly soluble in the monomers. The immiscibility of protein and n-butyl acrylate at all temperatures and the lack of a good common solvent were the main challenges when formulating materials. Drawing inspiration from studies that show that protein-surfactant complexation imparts organic solvent solubility to proteins[63], a surfactant was selected as a compatibilizer to improve protein-monomer miscibility. Whey protein isolate (WPI) was complexed with benzalkonium chloride (BAC), a cationic surfactant. The protein-surfactant complexes were prepared by mixing the two in water followed by lyophilization (see Example 2A). Miscible blends of protein-surfactant complexes appear as transparent solids after high temperature annealing or melt pressing. At certain compositions, the protein-surfactant complexes form miscible or homogeneous dispersions when mixed with n-butyl acrylate, as shown by the miscible regions in the ternary diagram (FIG. 3D). Miscible mixtures formed viscous, transparent fluids or transparent films after either mixing or compression molding at elevated temperatures. A composition where the protein is fully compatible with the acrylate monomer is selected for copolymerization and for studies on material mechanical properties and structure.

Figure 3B:
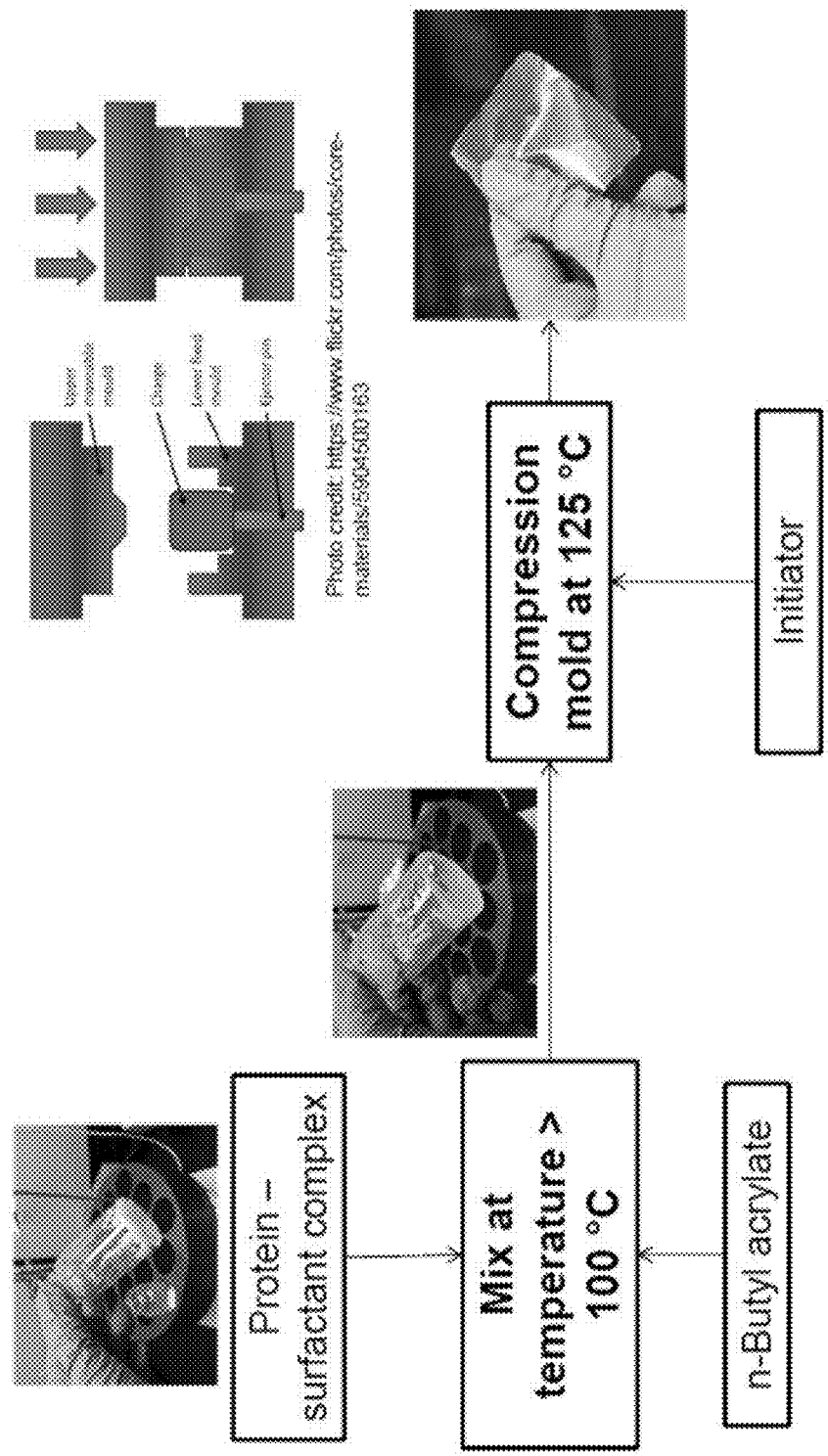
FIG. 3B depicts the process of preparing an exemplary copolymer comprising a modified protein monomer, a surfactant, and a second monomer.
Figure 3D:
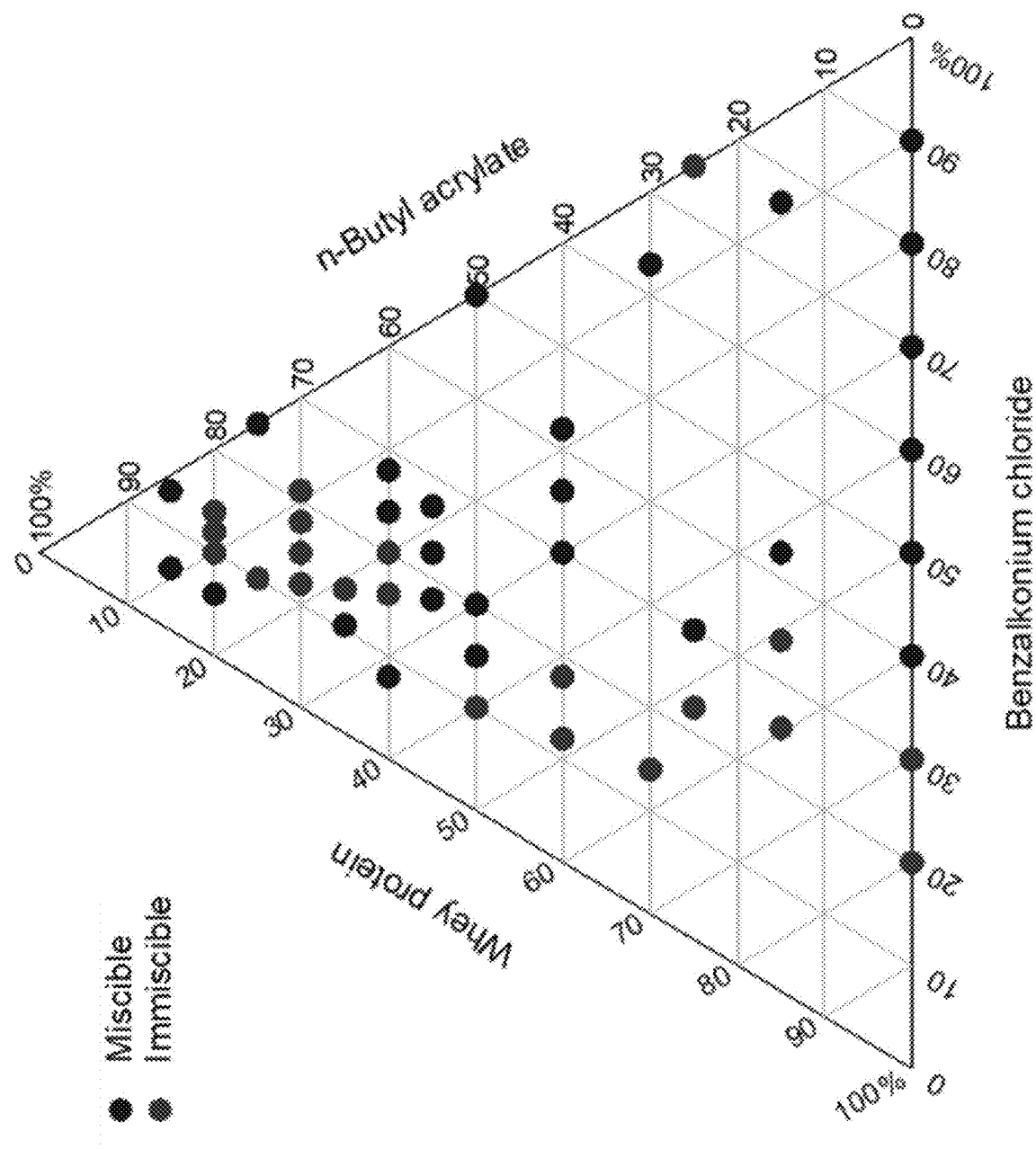
FIG. 3D depicts exemplary copolymers disclosed herein.
Figure 4A:
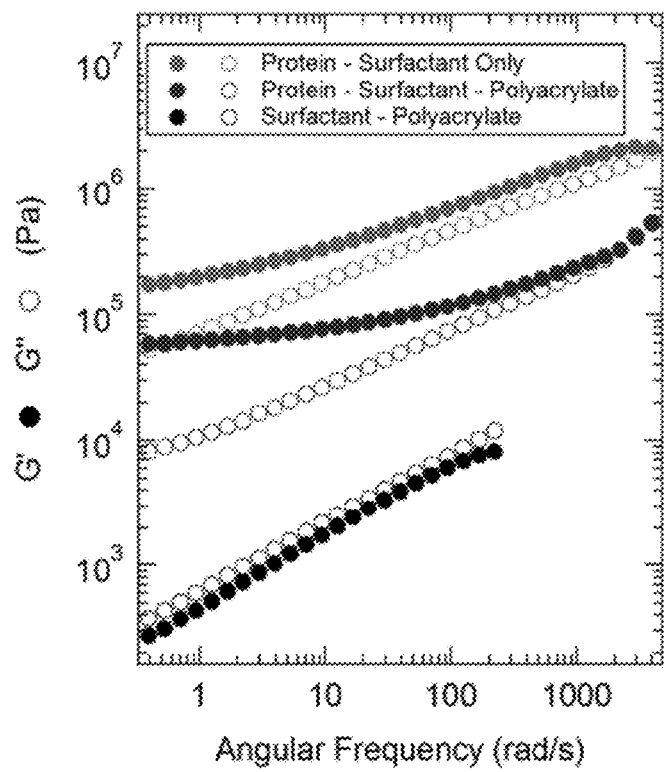
FIG. 4A depicts representative rheological data for exemplary protein copolymers comprising protein-surfactant-polyacrylate compared to a protein-surfactant complex and a surfactant-poly acrylate mixture showing the elastic response (storage modulus G') and viscous behavior (loss modulus G").
Figure 4B:
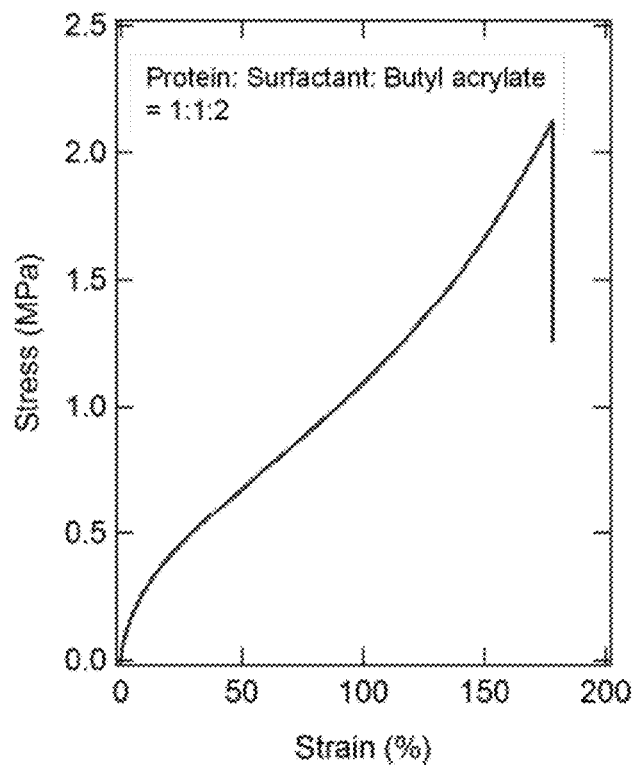
FIG. 4B depicts representative stress-strain curves for an exemplary protein copolymer with a mixture of protein: surfactant:n-butyl acrylate in ratios of 1:1:2.

FIG. 3B shows the process to form a protein-surfactant-acrylate copolymer. FIG. 3D shows exemplary protein-surfactant-acrylate copolymers and ratios of components. The protein-surfactant complex was mixed with n-butyl acrylate at complex to monomer mass ratio of 1:1, and with initiator tert-butyl peroxyacetate at initiator to n-butyl acrylate mole ratio of 1:100. The mixture was pressed into sheets and cured at 120° C. The crosslinked material, after incubation at 23° C. and 50% relative humidity has a modulus of ~4.7 MPa, ultimate tensile strength of ~2.1 MPa, and elongation-at-break of ~180% (FIG. 4B).

Figure 3C:
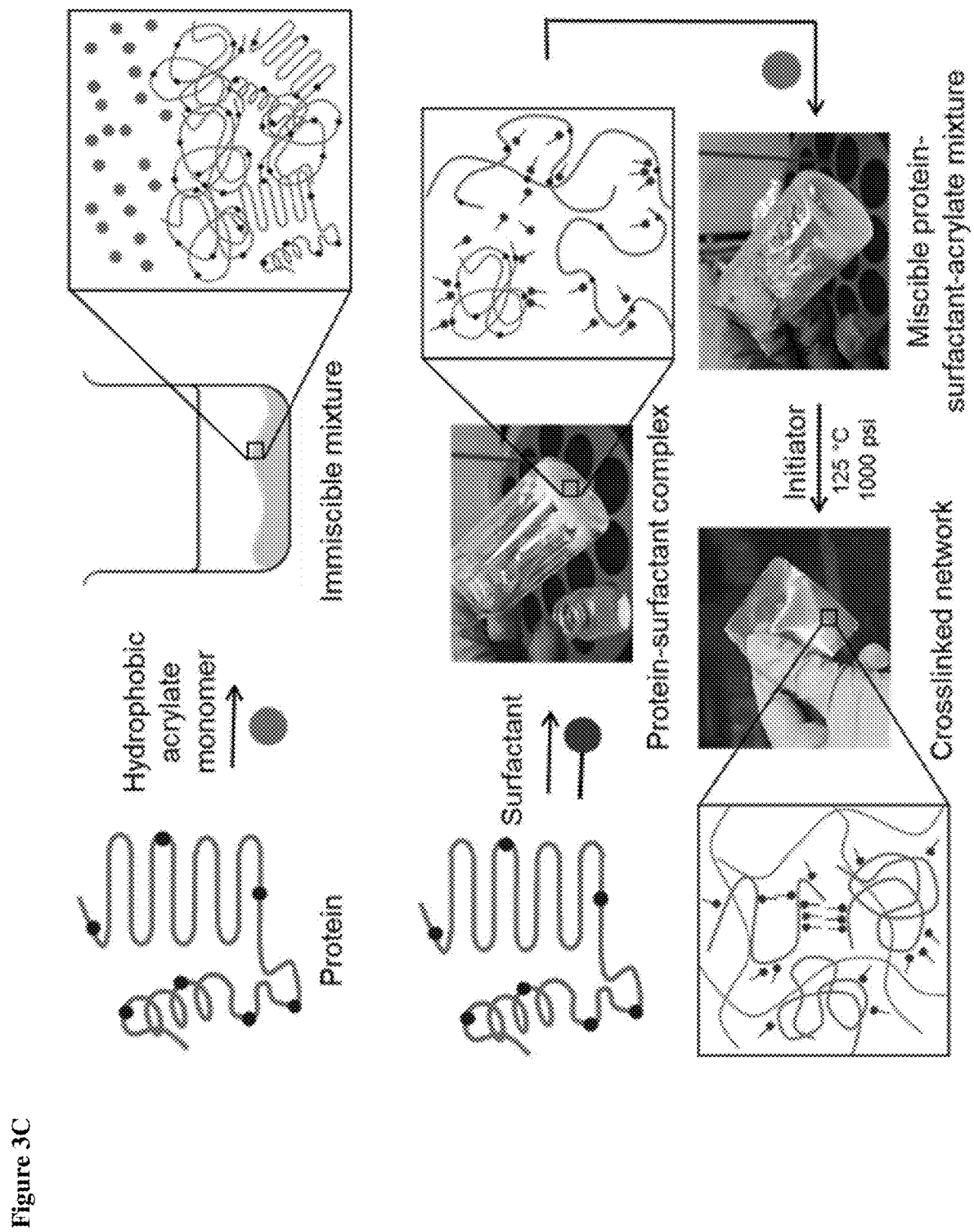
FIG. 3C depicts the process of preparing an exemplary copolymer comprising a modified protein first monomer, a surfactant, and a second monomer.

Elastomeric protein-surfactant-polyacrylate copolymer sheets were prepared by compression molding mixtures of protein-surfactant complexes and co-monomers (second monomers) in the presence of a thermal initiator (FIG. 3C). During compression molding at elevated temperatures, mixtures of protein, surfactant, and acrylate monomers were softened and pressed into sheets, while the polymerization process cures the material. The low vapor pressure surfactant does not participate in polymerization, and is left in the material as a plasticizer. Since the cured material does not contain solvent or volatile components, drying steps, warping and shrinkage challenges are eliminated.

n-Butyl acrylate and poly(ethylene glycol) methyl ether acrylate were passed over basic alumina to remove inhibitors. They were then added to protein-surfactant complexes heated to 110° C. at a monomer to complex mass ratio of 1:1, and thoroughly mixed by manually stirring. Initiator t-butyl peroxyacetate (50 wt % in mineral oil) was added at an initiator to monomer mole ratio of 1:80. The mixture was placed into a flat mold sandwiched with Teflon liners, transferred to a hydraulic press heated to 120° C., and polymerized under a pressure of 1000 psi for 30 minutes. After polymerization, the copolymers were cooled to room temperature under pressure, removed from the mold, and equilibrated at various relative humidity conditions for at least 72 hours prior to mechanical characterization. A Memmert HPP 110 climate control chamber was used to equilibrate samples at 23° C. and 20%, 35% 50%, or 80% relative humidity, while a dessicator with Drierite stored at room temperature was used for the 4% relative humidity condition. A crosslinked poly(butyl acrylate) control was prepared by mixing n-butyl acrylate, butanediol diacrylate, and azobisisobutyronitrile at a monomer to crosslinker to initiator mole ratio of 1:300:80, pipetted in between two glass plates with a 1 mm spacer, and polymerized at 70° C. for 30 minutes.

C. Ternary Diagram Construction

Miscibility of whey protein, benzalkonium chloride, and n-butyl acrylate at various ratios was determined by mixing the protein-surfactant complexes with butyl acrylate at the desired ratios at 110° C. (FIG. 3D). After cooling, homogeneous or optically clear mixtures were designated as miscible, while mixtures that were heterogeneous, opaque or macrophase separated were labelled immiscible. At low acrylate co-monomer (second monomer) concentrations, mixtures appear more solid-like, and were compression molded for miscibility determination. Mixtures that form optically isotropic and transparent films were classified as miscible.

D. Protein-Surfactant-2$^{nd}$ Monomer Copolymers.

Blending experiments were performed with unmodified proteins. Samples were compression molded at 250° F. The protein:surfactant:monomer mass ratio was 1:2:3.

In Table 1, the second monomer was n-butyl-acrylate, and films generally formed blending various proteins, various surfactants, and n-butyl acrylate as a second monomer. The surfactants tested include benzalkonium chloride (BAC), cetylpyridinium chloride (CPC), 1-vinyl-3-dodecylimidazolium bromide (Imid), dioctyl sulfosuccinate (AOT), and sodium oleate (Na oleate).

TABLE 1

Exemplary protein copolymers comprising a protein-surfactant-acrylate formed by compression molding using various surfactants.

|  | pI | BAC | CPC | Imid | AOT | Na oleate |
|---|---|---|---|---|---|---|
| Gelatin A | 7-9 | Film | Film | Film | Film | Film |
| Gelatin B | 4.7-5.2 | Film | Film | Film | Film | Film |
| Whey | 5 | Film | Film | Film | Film | Film |
| Lysozyme | 11 | Film | Film | Film | Film | Film |
| Zein | 6-7 | Film | Film | Film | Film | No film |

In Table 2, films formed after compression molding various monomers and either whey protein isolate mixed with benzalkonium chloride (WPI-BAC) or lysozyme mixed with dioctyl sulfosuccinate (LYZ-AOT). The various monomers tested include n-butyl acrylate (n-BA), poly(ethylene glycol) methyl ether methacrylate (PEGMA), acrylic acid (AA), dimethylacrylamide (DMAA), and styrene.

TABLE 2

Exemplary protein copolymers comprising a protein-surfactant-acrylate formed by compression molding using various second monomers.

| Monomer | Water soluble? | Tg (° C.) | WPI-BAC | LYZ-AOT |
|---|---|---|---|---|
| n-BA | No | −54 | Film | Film |
| PEGMA | Yes | −62 | Film | Film |
| AA | Yes | 105 | Film | Film |
| DMAA | Yes | 89 | Film | Film |
| Styrene | No | 100 | Film | No film |

Example 3—Protein Copolymer Characterization

A. Mechanical Testing.

I. Mechanical Testing on Exemplary Dried Copolymers

The copolymers described herein form thermoset elastomers after drying.

Comparisons of the protein-surfactant-polyacrylate copolymers to protein-surfactant complexes and surfactant-polyacrylate blends show that desirable elastomeric properties require the presence of surfactants and covalent attachment of modified protein to polyacrylate. FIG. 4A depicts representative rheological response for exemplary protein copolymers comprising protein-surfactant-polyacrylate compared to a protein-surfactant complex and a surfactant-polyacrylate mixture showing the elastic response (storage modulus G') and viscous behavior (loss modulus G"). The surfactant-polyacrylate mixture is more fluid-like than solid-like, as shown in the higher loss modulus when compared to storage modulus. The protein-surfactant-polyacrylate comprised partly of protein-surfactant and polyacrylate has moduli in between the two. In the absence of reinforcing fillers, the surfactant-polyacrylate mixture is rubbery and weak at room temperature. Proteins therefore appear to act synergistically with the flexible polyacrylates, as seen in the orders of magnitude improvement in both strength and toughness (FIGS. 4A and 4B), which are typically conflicting qualities in many engineering materials[34].

When the polymer is absent, unplasticized whey protein, like many other commonly investigated dry proteins, is very brittle. Its mechanical properties are not shown due to difficulties in handling and testing it in tension. Protein in the blend is analogous to reinforcing fillers in composites, and polymer composite mechanical properties are typically highly influenced by interfacial interactions between filler and matrix[35]. In the copolymer where proteins are covalently attached to polyacrylate chains and interact with surfactants, external loads may be more efficiently transferred from the polyacrylate matrix to the stiff protein aggregates, leading to enhanced stiffness and strength, as demonstrated with crosslinked nanotube-epoxy composites[36].

Figure 5A:
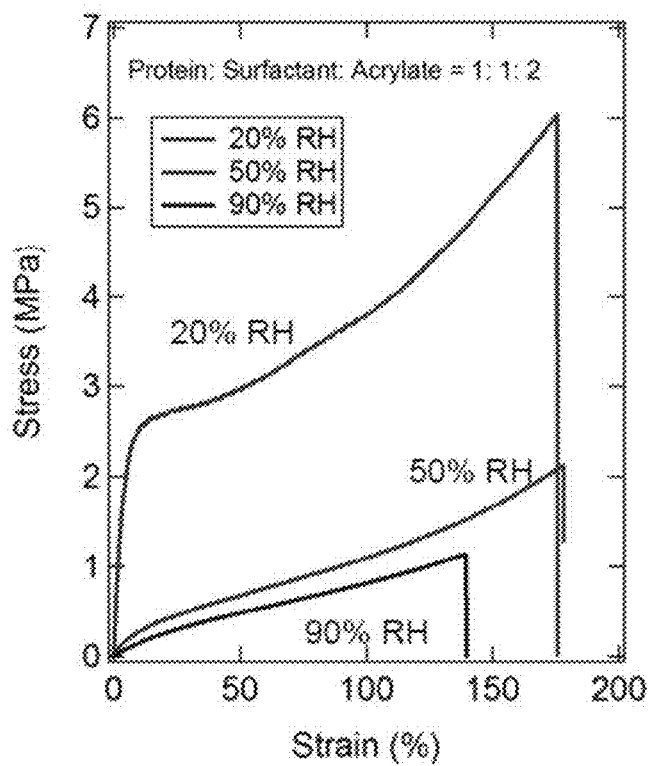
FIG. 5A depicts representative stress-strain curves for exemplary protein copolymers demonstrating the dependence of yield stress and strain hardening on humidity.
Figure 5B:
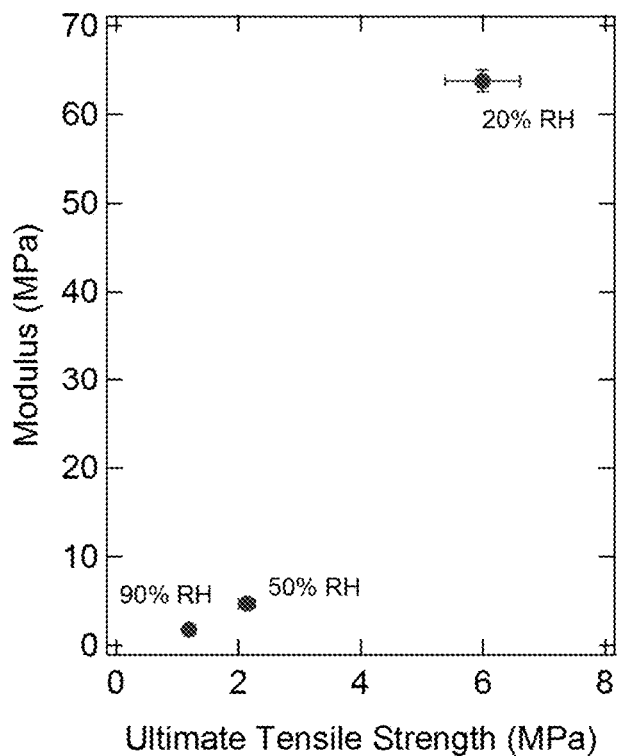
FIG. 5B depicts the dependence of ultimate tensile strength as a function of humidity for exemplary protein copolymers.
Figure 5C:
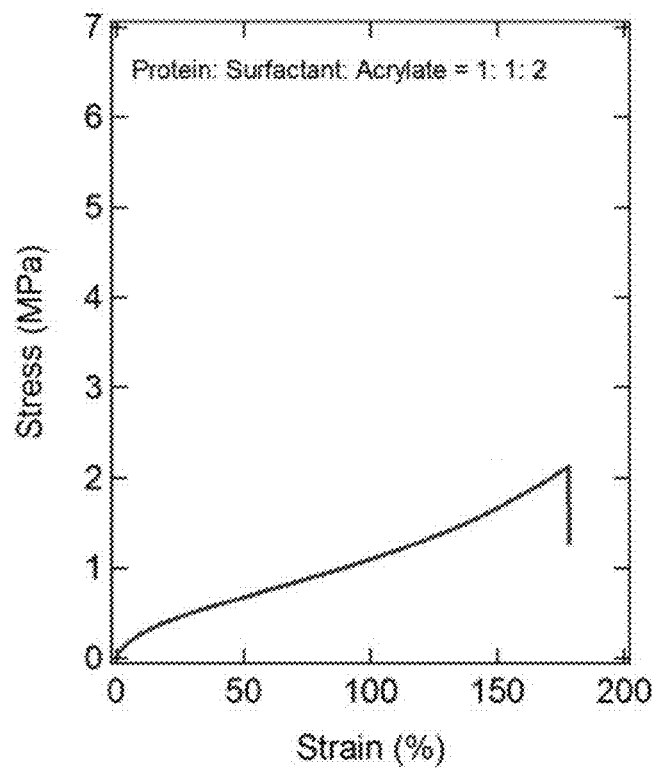
FIG. 5C depicts a representative stress-strain curve for an exemplary protein-surfactant-acrylate copolymer at 50% RH with a water content of 3:4% by mass.
Figure 6:
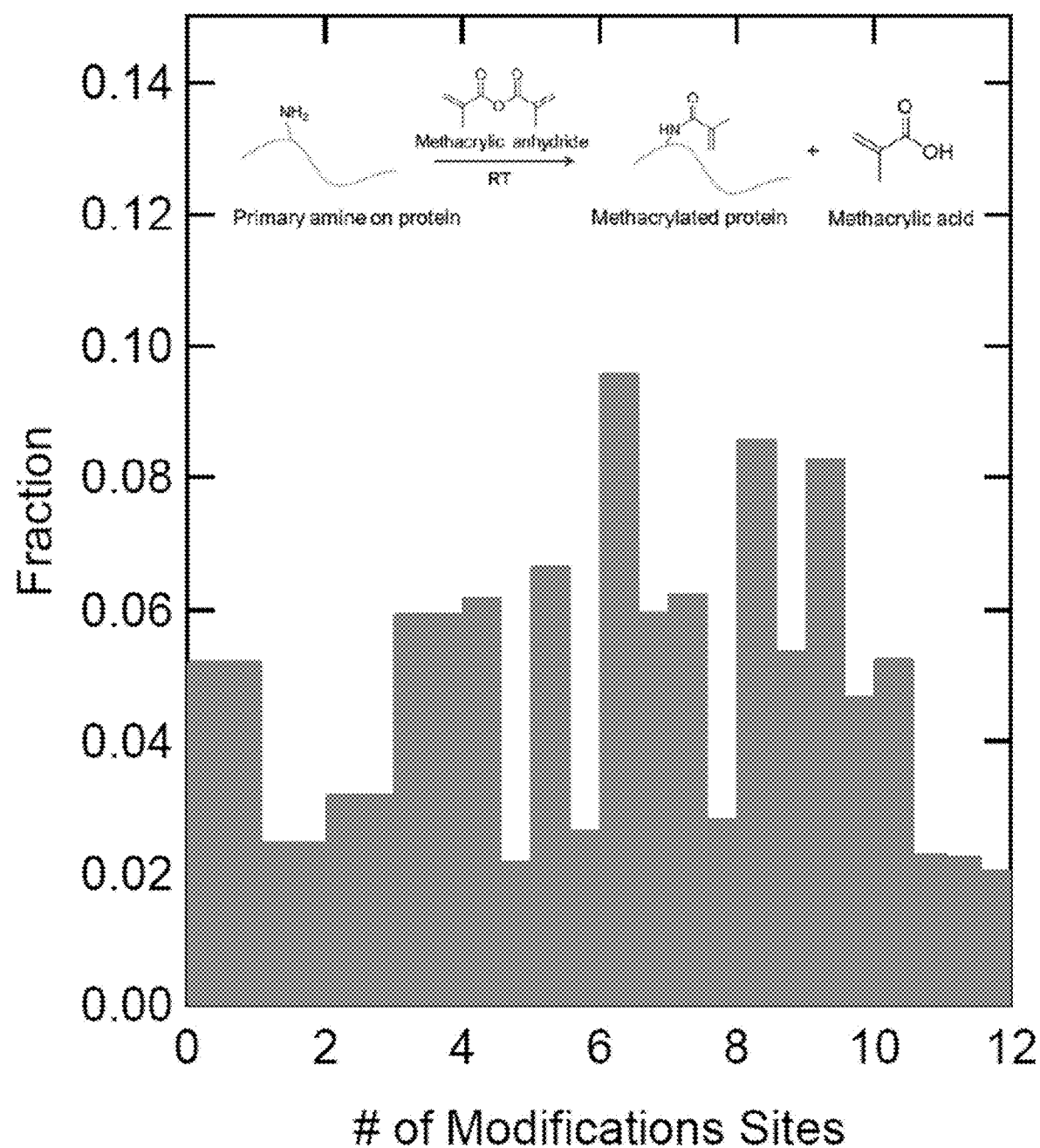
FIG. 6 depicts the number of modification sites on an exemplary modified protein.
Figure 7:
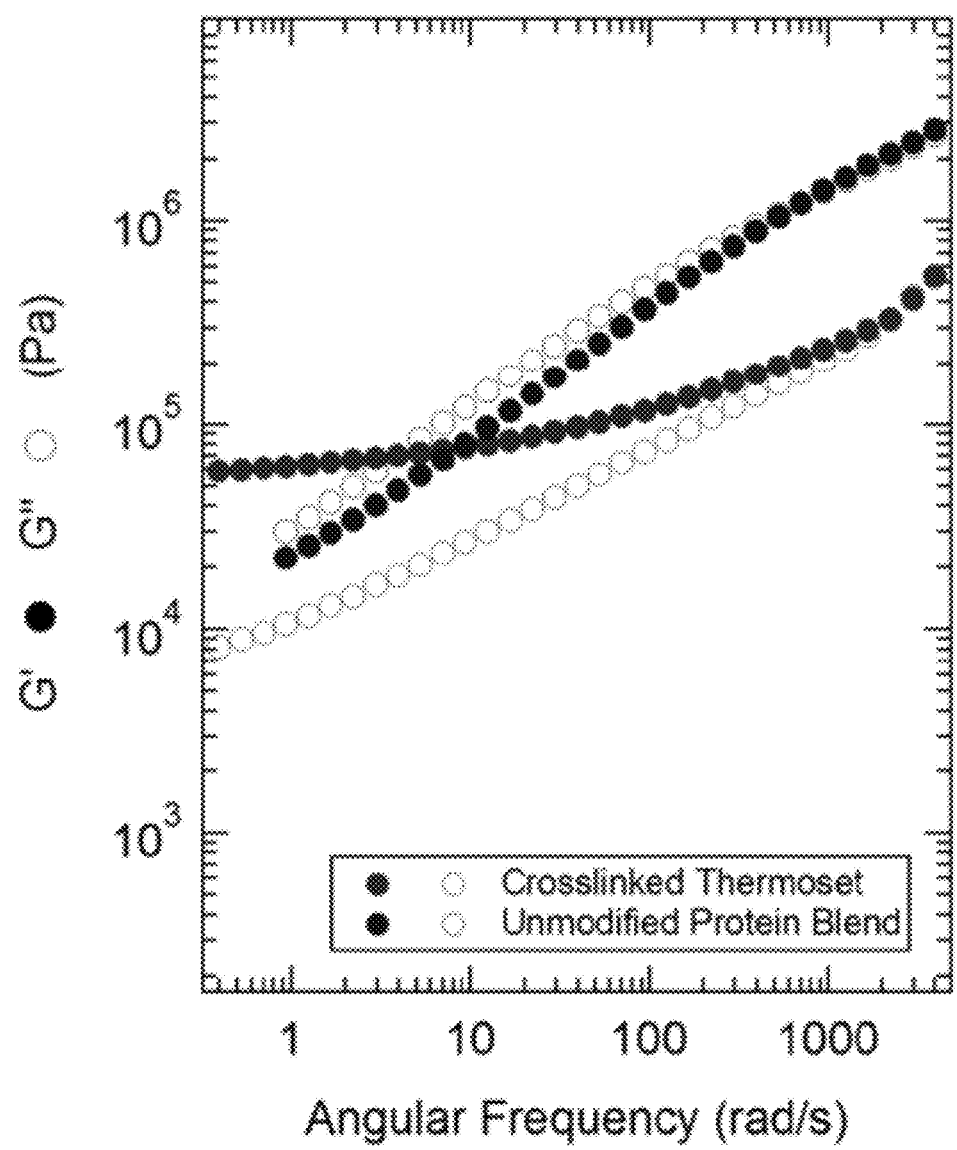
FIG. 7 depicts representative rheological data for an exemplary protein copolymer comprising protein-surfactant-polyacrylate to form a crosslinked thermoset compared to an unmodified protein blend showing the elastic response (storage modulus G') and viscous behavior (loss modulus G").

The protein-surfactant-polyacrylate copolymers retain their stiffness and strength at humid conditions (FIGS. 5A and 5B). The methacrylamide groups on proteins serve as crosslinking points (FIG. 6). The crosslinked thermoset polymer maintains elasticity but is also strong (FIG. 7).

Figure 8:
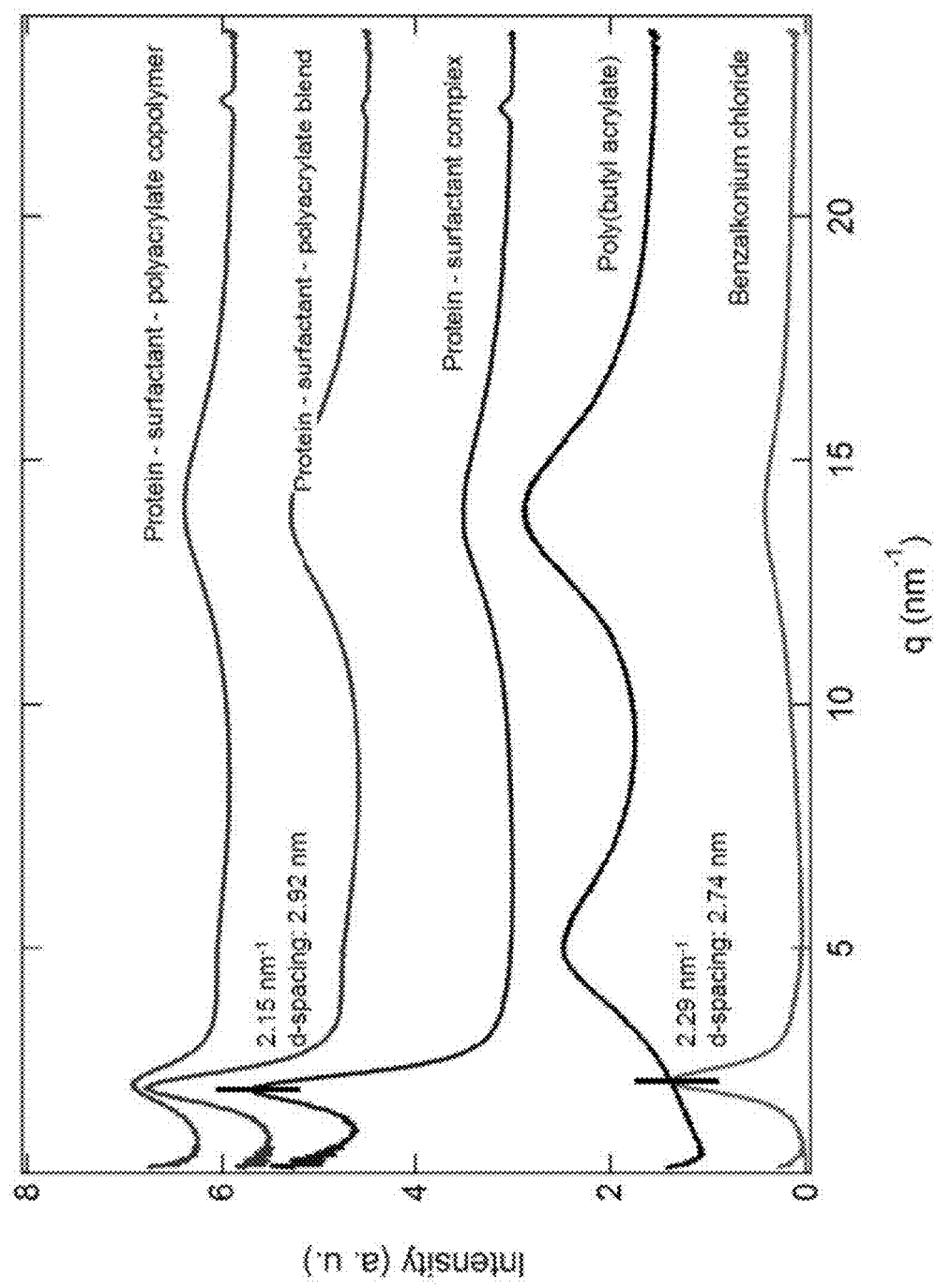
FIG. 8 depicts the disordered nature of an exemplary protein copolymer and an exemplary blend comprising protein-surfactant-polyacrylate compared to a protein-surfactant complex, polyacrylate, and surfactant.

The protein-surfactant-polyacrylate thermoset copolymers may have disordered structures (FIG. 8).

Figure 9:
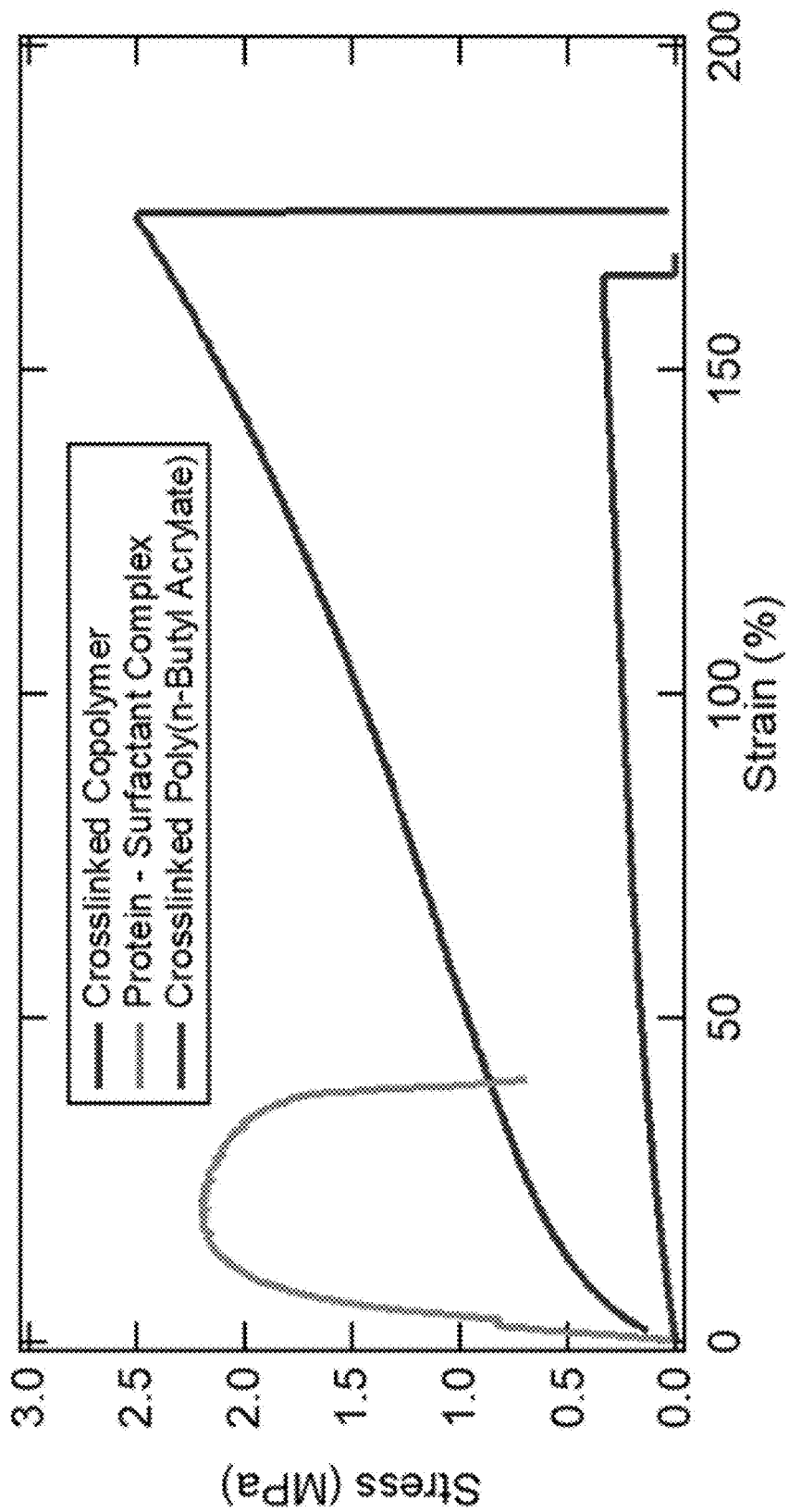
FIG. 9 depicts representative stress-strain curve for an exemplary protein-surfactant complex, an exemplary protein-surfactant-polyacrylate copolymer, and an exemplary crosslinked polyacrylate.

Achieving high strength and toughness in the material requires the presence of both stiff protein domains for reinforcement and rubbery polymer domains for extensibility. On its own, the protein-surfactant complex is stiff but has low elongation-at-break and toughness (FIG. 9, Table 3), properties commonly observed for plasticized protein films. These films were prepared by compression molding, which softens and fuses the WPI-BAC complexes to produce a continuous matrix. On the other hand, poly(n-butyl acrylate) is a liquid at room temperature, with a glass transition temperature of −55° C. Unreinforced poly(n-BA) crosslinked with butanediol diacrylate at a crosslinker to monomer mole ratio of 1:300 produced a soft rubber with low modulus and toughness. A copolymer prepared with proteins with an average of 6 methacrylamide groups per protein was shown to possess both high mechanical strength and extensibility, and is tougher than its constituents. This synergistic combination of a hard and soft component is typically regarded to be central in the design of high performance engineering plastics like polyurethanes. FIG. 9 depicts representative stress-strain curve for an exemplary protein-surfactant complex (WPI-BAC), an exemplary protein-surfactant-poly acrylate copolymer (WPI-BAC-poly(n-BA), averaging 6 methacrylamide groups per protein), and an exemplary crosslinked polyacrylate (poly(n-BA) at 1:300 crosslinker to monomer ratio). All materials were conditioned at 23° C. and 50% relative humidity prior to testing.

TABLE 3

Comparison of mechanical properties. The crosslinked copolymer was prepared using whey protein with an average of 6 methacrylamide functionalities and a protein:surfactant:n-butyl acrylate ratio of 1:1:2. Complexes were prepared at a protein:surfactant ratio of 1:1.

| | Modulus (MPa) | Tensile Strength (MPa) | Elongation-at-Break (%) | Toughness (MJ/m$^2$) |
| --- | --- | --- | --- | --- |
| Crosslinked protein-surfactant-poly(n-butyl acrylate) | 6.0 ± 0.4 | 2.3 ± 0.2 | 166 ± 17 | 2.1 ± 0.4 |
| Protein-surfactant complex | 50 ± 14 | 2.5 ± 0.5 | 35 ± 5 | 0.6 ± 0.3 |
| Crosslinked poly(n-butyl acrylate) | 0.460 ± 0.015 | 0.30 ± 0.07 | 140 ± 30 | 0.27 ± 0.07 |

Figure 10A:
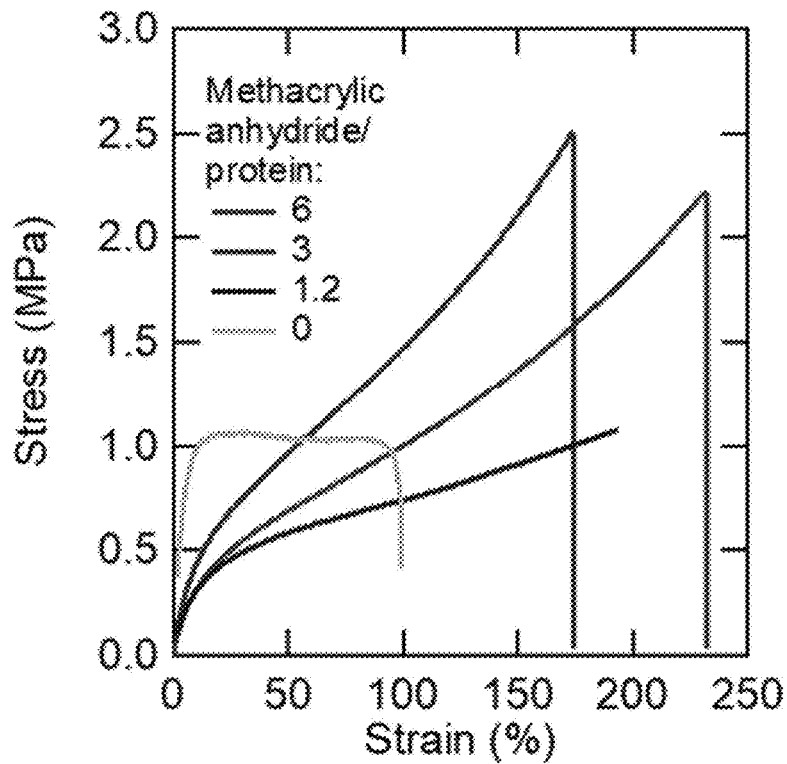
FIG. 10A depicts representative stress-strain curves for exemplary protein-surfactant-polyacrylate blend and exemplary protein-surfactant-polyacrylate copolymers with a range of methacrylation levels.
Figure 10B:
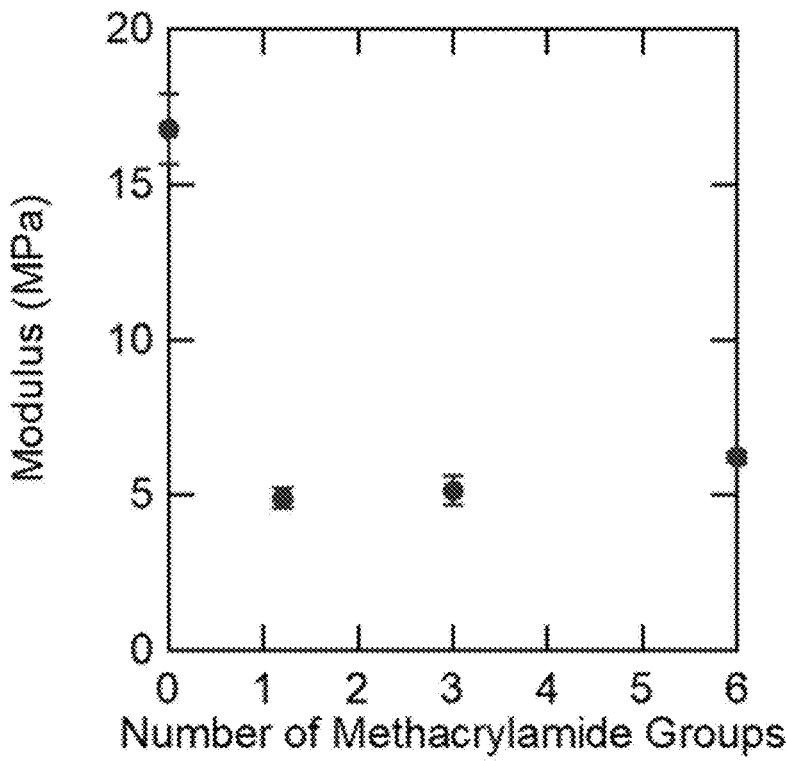
FIG. 10B depicts the dependence of modulus as a function of methacrylation levels for exemplary protein-surfactant-polyacrylate blend and for exemplary protein-surfactant-polyacrylate copolymers.
Figure 10C:
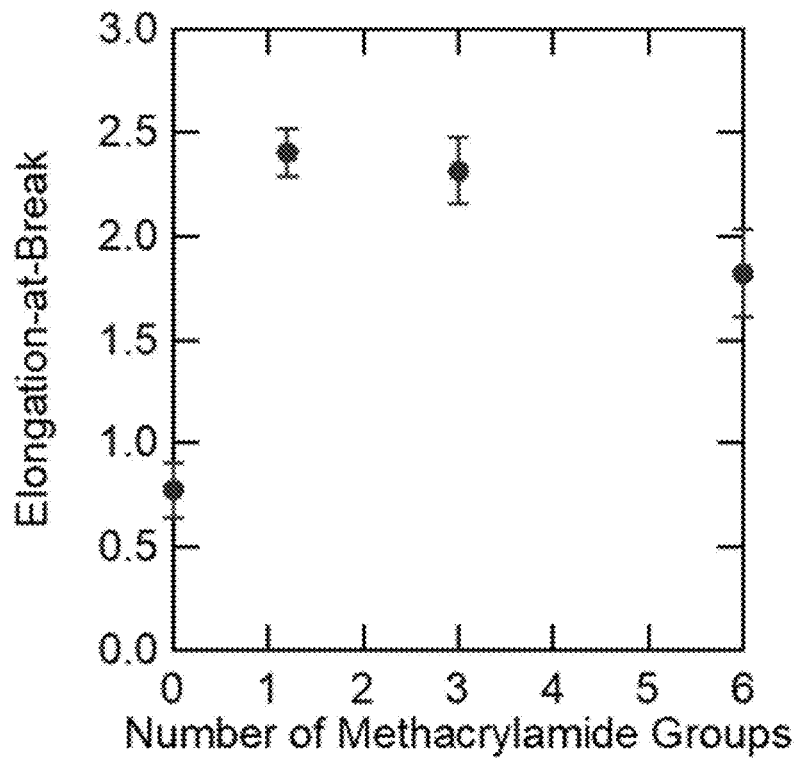
FIG. 10C depicts the dependence of elongation-at-break as a function of methacrylation levels for exemplary protein-surfactant-polyacrylate blend and for exemplary protein-surfactant-poly acrylate copolymers.
Figure 10D:
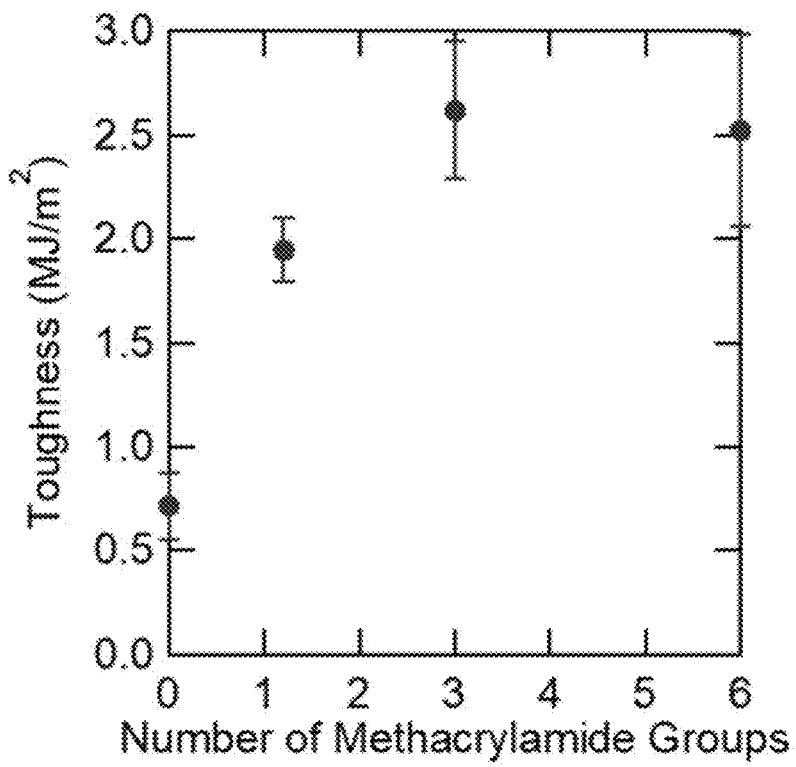
FIG. 10D depicts the dependence of toughness as a function of methacrylation levels for exemplary protein-surfactant-polyacrylate blend and for exemplary protein-surfactant-poly acrylate copolymers.

The presence of methacrylamide groups in proteins as a result of the reaction between whey and methacrylic anhydride heavily influences mechanical properties, as they provide sites for the protein to be covalently attached to the rubbery polyacrylate chains during polymerization. The level of protein functionalization therefore modulates crosslinking density. Characterization of the degree of methacrylation using a reaction with p-lactoglobulin is described above. In the case of a blend, where the protein is unmodified, materials prepared have higher modulus but lower elongation-at-break than all crosslinked materials with varying protein methacrylation levels (FIGS. 10A to 10C). Both tensile strength and toughness initially increase with increasing crosslinking density, but level off at high levels of methacrylation (Table 3, FIG. 10D). Large differences between the blend and all copolymers of various crosslinking densities could arise from structural differences, where proteins in the blend function only as fillers.

II. Effect of Humidity on Mechanical Properties

Figure 11:
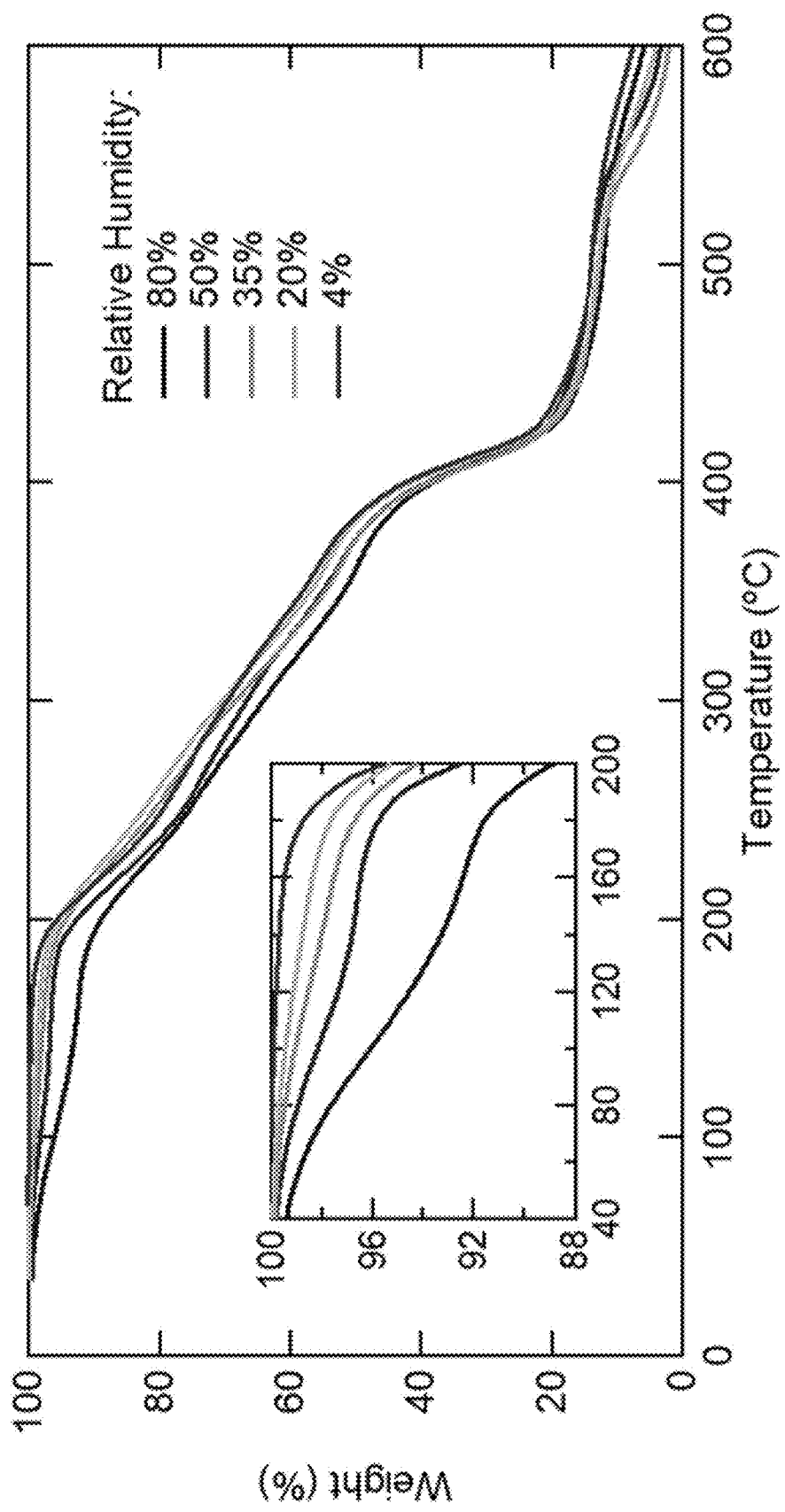
FIG. 11 depicts TGA curves for exemplary protein-surfactant-polyacrylate copolymer at various relative humidity levels.

Miscible blends of proteins and highly hydrophobic monomers enable the preparation of less hygroscopic protein copolymers. n-Butyl acrylate was selected as a model hydrophobic monomer, as its homopolymer absorbs ~0% moisture after incubation at 23° C. and 80% relative humidity. In contrast, solution cast whey protein absorbs 13% moisture under the same conditions. The disparity in moisture absorption between proteins and hydrophobic synthetic polymers highlights the challenge of formulating protein-based materials with consistent properties regardless of environmental conditions, as water can soften materials by swelling or plasticizing polymers to reduce glass transitions. Moisture absorption at 80% relative humidity for a protein-surfactant complex (mass ratio: 1:1) and a copolymerized protein-surfactant-polyacrylate (WPI-BAC-poly(n-BA), mass ratio: 1:1:2) are 11.6% and 7.2% respectively (FIG. 11), showing the positive effect of n-butyl acrylate co-monomer (second monomer) in decreasing the overall water absorption. The inset of FIG. 11 shows mass losses below 200° C. Losses below 150° C. were attributed to absorbed moisture.

Figure 12A:
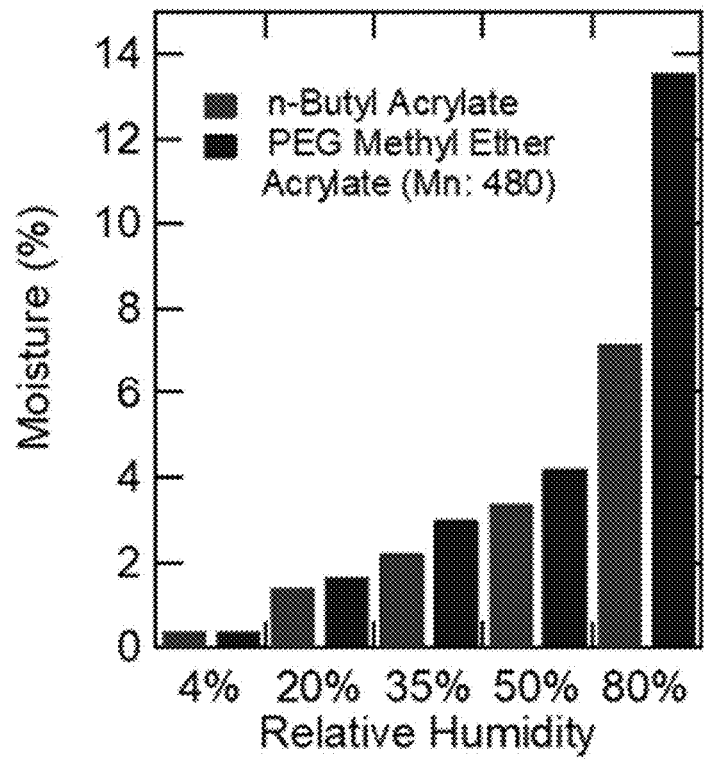
FIG. 12A depicts moisture content of exemplary protein-surfactant-poly acrylate copolymer incubated at 23° C. and various relative humidity levels.
Figure 12B:
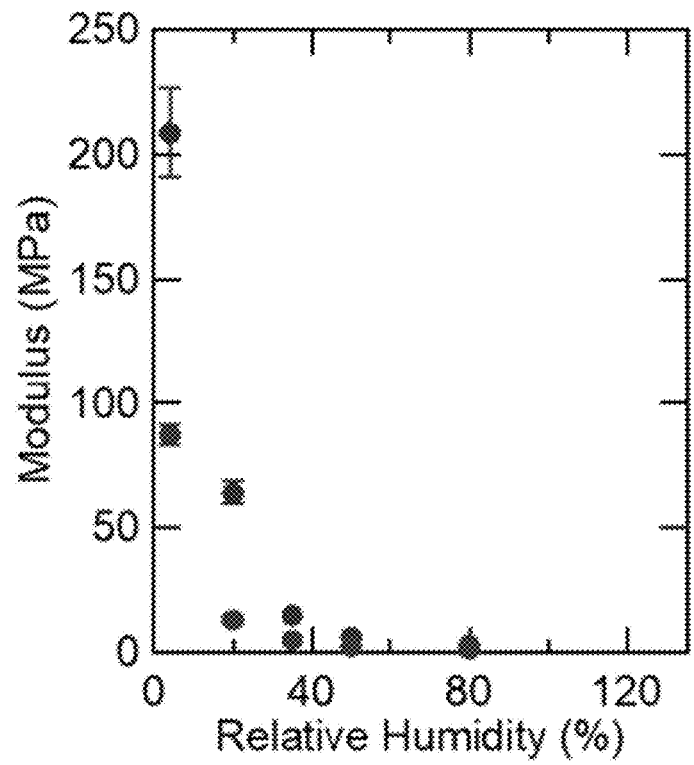
FIG. 12B depicts the dependence of modulus as a function of various relative humidity levels for exemplary protein-surfactant-polyacrylate copolymers.
Figure 12C:
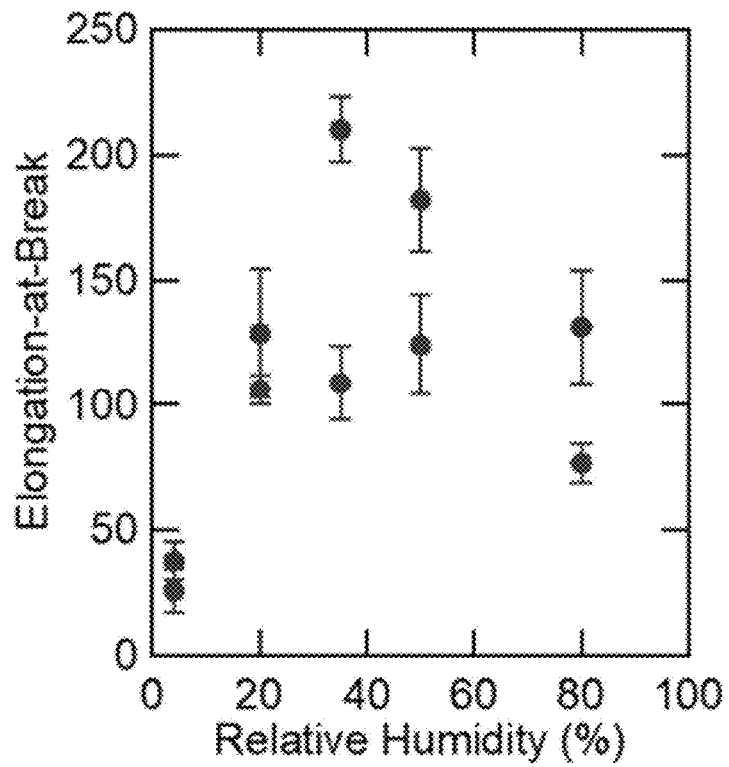
FIG. 12C depicts the dependence of elongation-at-break as a function of various relative humidity levels for exemplary protein-surfactant-polyacrylate copolymers.
Figure 12D:
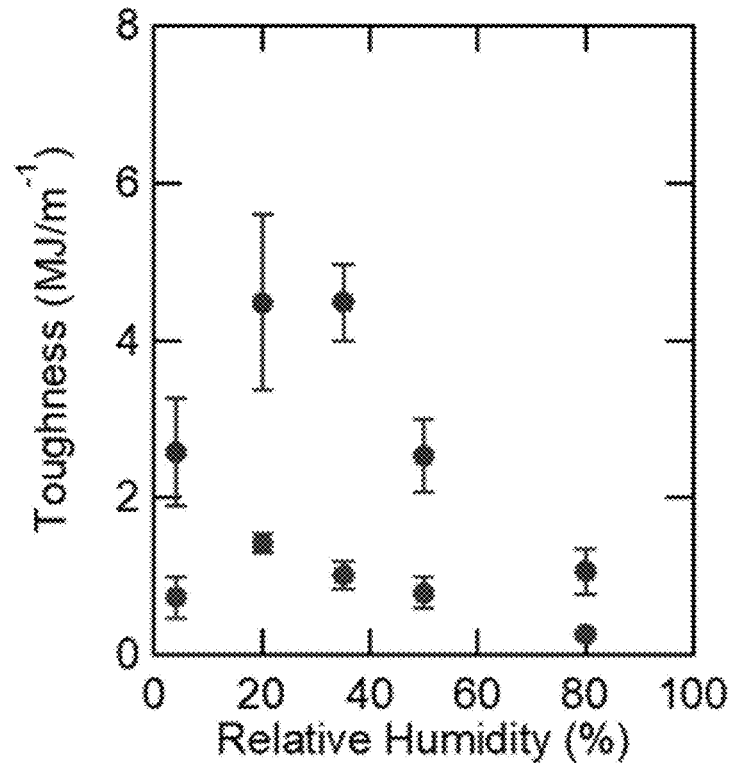
FIG. 12D depicts the dependence of elongation-at-break as a function of various relative humidity levels for exemplary protein-surfactant-polyacrylate copolymers.

To elucidate the role of monomers on moisture absorption and provide a direct comparison to n-butyl acrylate, materials were also prepared with a water soluble monomer, poly(ethylene glycol) methyl ether acrylate. Like butyl acrylate, this monomer has a homopolymer Tg well below room temperature, which eliminates effects of Tg change with water absorption on mechanical property differences. While both types of copolymers absorb the same amount of water after dessication, differences in moisture content increase rapidly with humidity levels (FIG. 12A). At 80% relative humidity, the hydrophilic copolymer absorbs nearly two times more moisture than the n-butyl acrylate based copolymer. Across all conditions, the PEG based hydrophilic copolymer performs worse than the n-butyl acrylate based copolymer. Major differences were observed for dried materials, even though their moisture content was similar. This may be due to differences in monomer size, which has been observed in other studies where the larger monomer was hypothesized to form more homopolymers than copolymers with the protein due to sterics. On the other hand, tensile properties of both copolymers exhibit similar trends with humidity. Both materials soften considerably above 20% relative humidity, and have elongation-at-break and toughness that peak between 20-50% relative humidity (FIGS. 12B-12D). The copolymers maintain their structural integrity and toughness even in high humidity conditions. An optimal relative humidity for toughness exists, as small amounts of water act as plasticizers and raise material extensibility at low humidity levels. Above a certain water content, the markedly softer materials fracture at much lower tensile strengths, resulting in decreased toughness. Similarities in the trends suggest that water absorption in protein domains play a large role in material softening, even while incorporation of a hydrophobic component reduces moisture absorption.

Specimens for uniaxial static tensile testing were cut using an ASTM D1708 microtensile die from Pioneer Dietecs. Samples were tested at a rate of 100% strain/min on a Zwick Z05 machine in tensile mode at ambient conditions. Three specimens were tested for each material, and the averages and standard deviations were reported.

B. Thermal Characterization.

Moisture content in materials was determined using thermogravimetric analysis (TGA) using a TA Instruments Discovery TGA instrument. Samples equilibrated under different conditions were heated under air flow at a rate of 20° C. $min^{-1}$. Total mass loss at 150° C. were attributed to moisture content.

Figure 13:
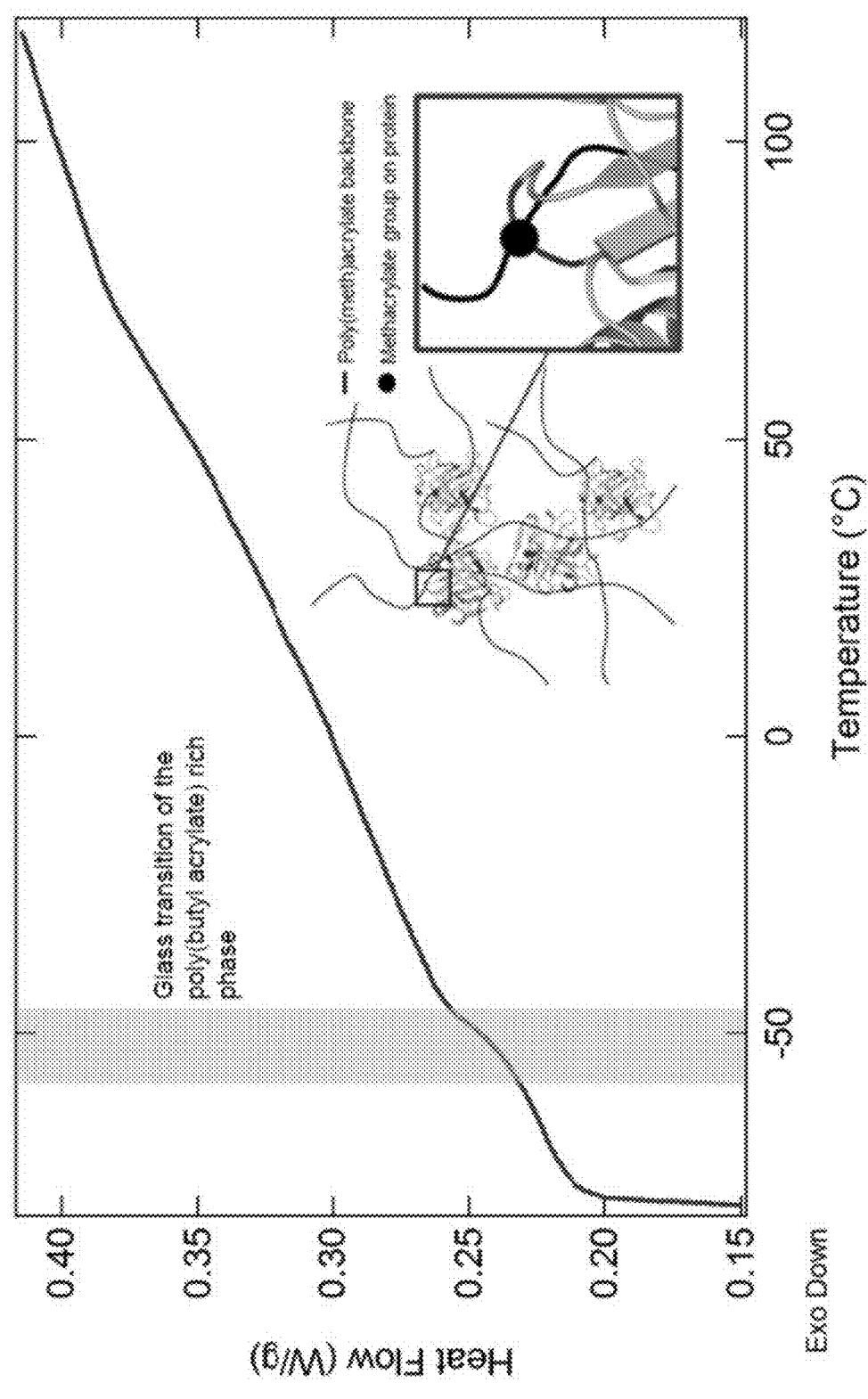
FIG. 13 depicts the microphase separation of an exemplary protein copolymer comprising protein-surfactant-polyacrylate.

Glass transitions and chain relaxations observed using differential scanning calorimetry (DSC) support the presence of phase separated domains in the copolymers. DSC results show that the poly(butyl acrylate) rich phase undergoes a midpoint glass transition at around −50° C. (FIG. 13).

Figure 14A:
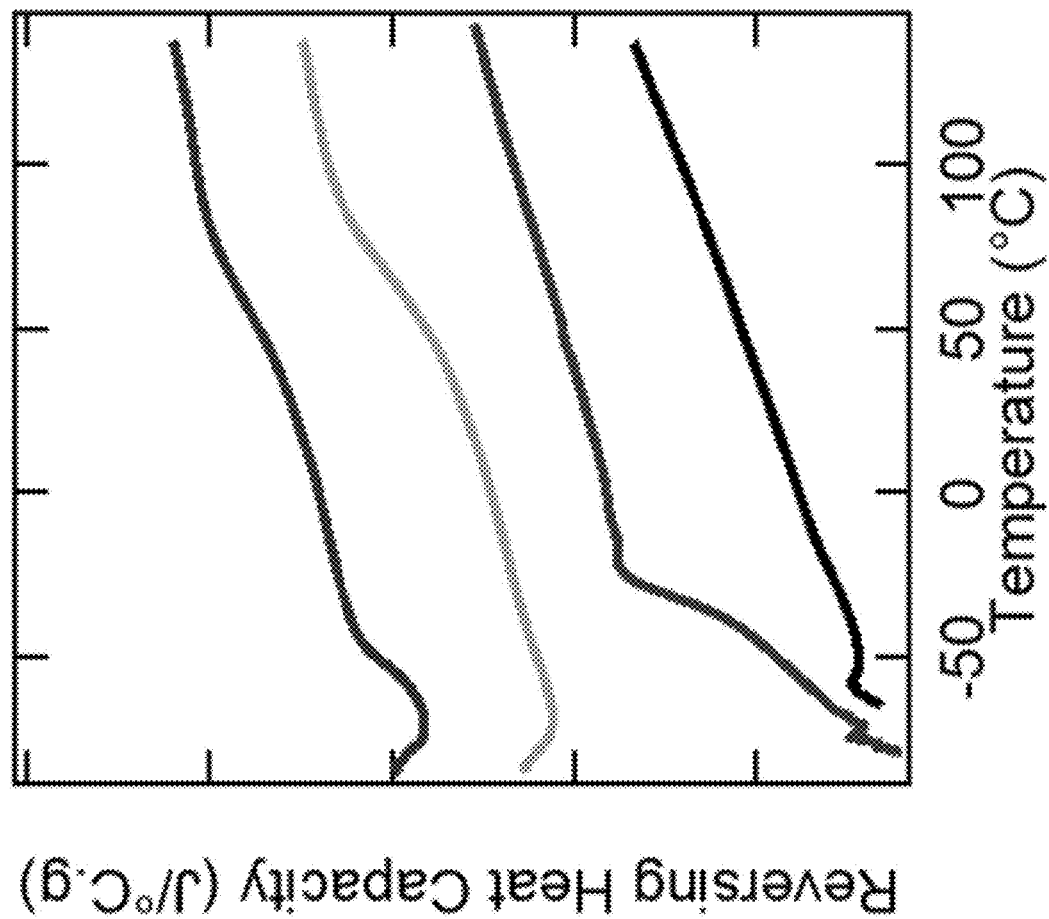
FIG. 14A depicts reversing heat capacity thermograms for exemplary protein copolymer comprising protein-surfactant-polyacrylate, protein-surfactant complex, surfactant, and protein from top to bottom.
Figure 14B:
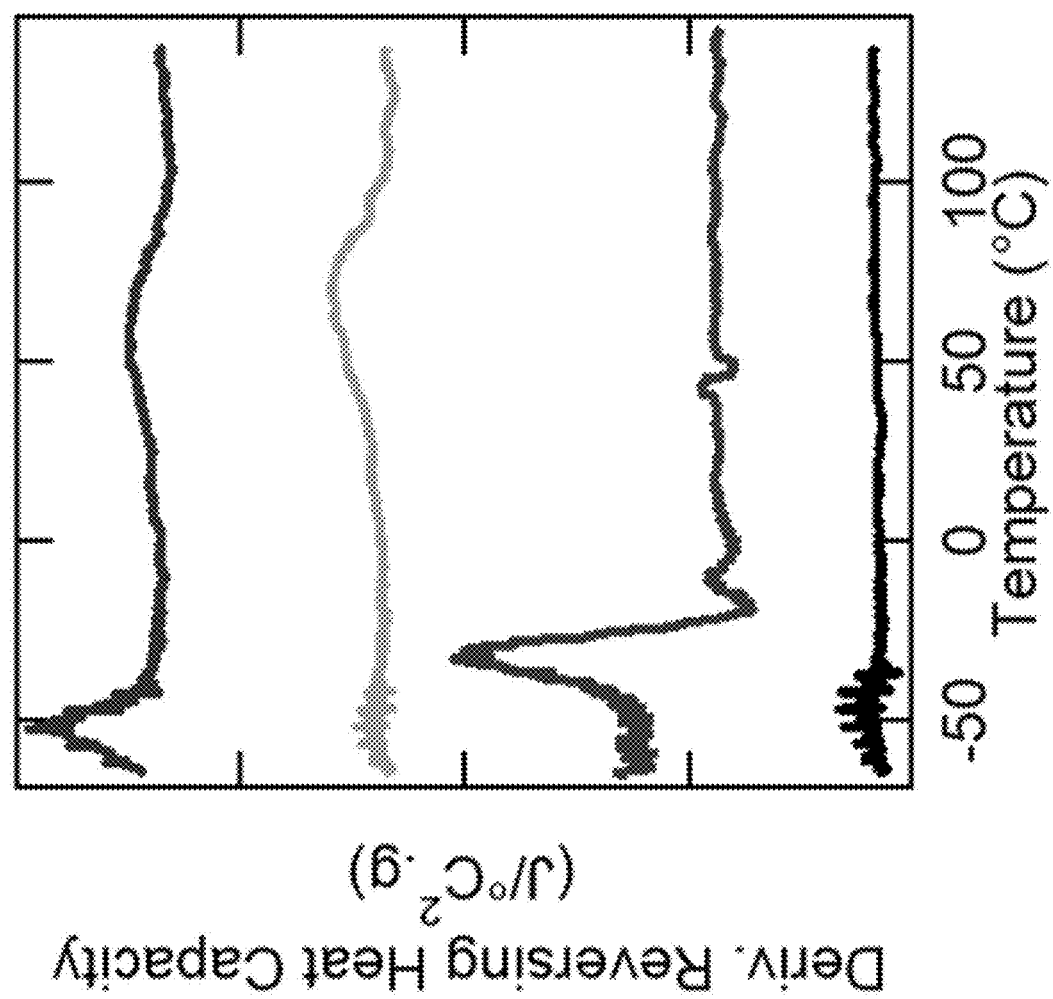
FIG. 14B depicts first order derivative of reversing heat flow versus temperature from modulated DSC runs on for exemplary protein copolymer comprising protein-surfactant-polyacrylate, protein-surfactant complex, surfactant, and protein from top to bottom.

Besides functioning as a compatibilizer, the surfactant also reduces the melting point of proteins and enables the protein mixture to be thermoformed without the use of solvents. Thermal transitions of a desiccated protein-surfactant-polyacrylate copolymer and its constituents are measured with modulated differential scanning calorimetry (MDSC). Materials were dried prior to measurement to demonstrate properties of whey protein, benzalkonium chloride, and acrylate during solvent-free blending and melt polymerization. Glass transitions of the amorphous materials manifest in step changes in their reversing heat capacity and peaks in the first derivative of reversing heat capacity versus temperature (FIGS. 14A and 14B). Dry whey protein does not undergo a glass transition when heated up to 150° C. while the surfactant, BAC, has a midpoint glass transition temperature (Tg) at around −32° C. A binary miscible mixture comprised of 50% protein and 50% surfactant has a single Tg at 68° C., which suggests that the protein is plasticized. Tg's of other proteins have also previously been shown to be high when the protein is dry and are rapidly lowered in the presence of solvent or plasticizer, as a result of disrupted hydrogen bonding and electrostatic interactions, and increased protein chain mobility. While previous studies on surfactants as plasticizers in protein films are limited, some have focused on sodium dodecyl sulfate (SDS) and diacetyl tartaric ester of monoglycerides[64,65]. Their effectiveness as plasticizers have been reported to be low, as shown in the small increases in extensibility when incorporated into compression molded proteins[65], and they are more effective as coplasticizers[66]. On the other hand, the use of ionic surfactants in the synthesis of solvent-free protein melts has demonstrated that protein melting points can be drastically lowered by complexing charged proteins with ionic surfactants with long alkyl tails[67,68]. This inspired the selection of BAC, a low melting point cationic surfactant, as the plasticizer, since the main component of whey protein, β-lactoglobulin, has a small net negative charge at neutral pH (isoelectric point: 5.3)[69,70]. The resulting WPI-BAC protein-surfactant complex not only has a low glass transition temperature, but also softens considerably when heated and mixed with the liquid n-butyl acrylate. Above the blending temperature of 110° C., the miscible three component mixtures can appear as pastes or viscous fluids, and are amenable to molding and melt polymerization.

Thermal properties of the copolymer were analyzed using differential scanning calorimetry (DSC). Modulated DSC was performed using a TA Instruments Discovery DSC. In some experiments, materials were subjected to two heating cycles and one cooling cycle with a temperature ramp rate of 10° C./min from −80° C. to 200° C. with an isothermal dwell of 1 min at the end of each ramp. The second heating ramp was used to determine the transition temperatures. Samples were conditioned at 23° C. and 50% relative humidity prior to tests, and were subjected to a heating and cooling cycle to remove thermal history.

In some experiments, materials were subjected to two heating cycles and one cooling cycle with a temperature ramp rate of 5° C. $min^{-1}$ from −90 to 150° C. and temperature modulation of 2° C. $min^{-1}$ every 60 sec. The second heating ramp was used to determine reversible transition events. The protein:surfactant ratio for the complex is 1:1, while the protein:surfactant:co-monomer (second monomer) ratio for the copolymer is 1:1:2. Copolymer was prepared with protein with an average methacrylamide functionality of 6. All materials were desiccated prior to measurements. Curves are offset for clarity showing protein-surfactant-poly acrylate copolymer (WPI-BAC-polyBA copolymer), protein-surfactant complex (WPI-BAC), surfactant (BAC), and protein (WPI) from top to bottom in FIGS. 14A and 14B.

C. Protein Conformation.

Figure 15:
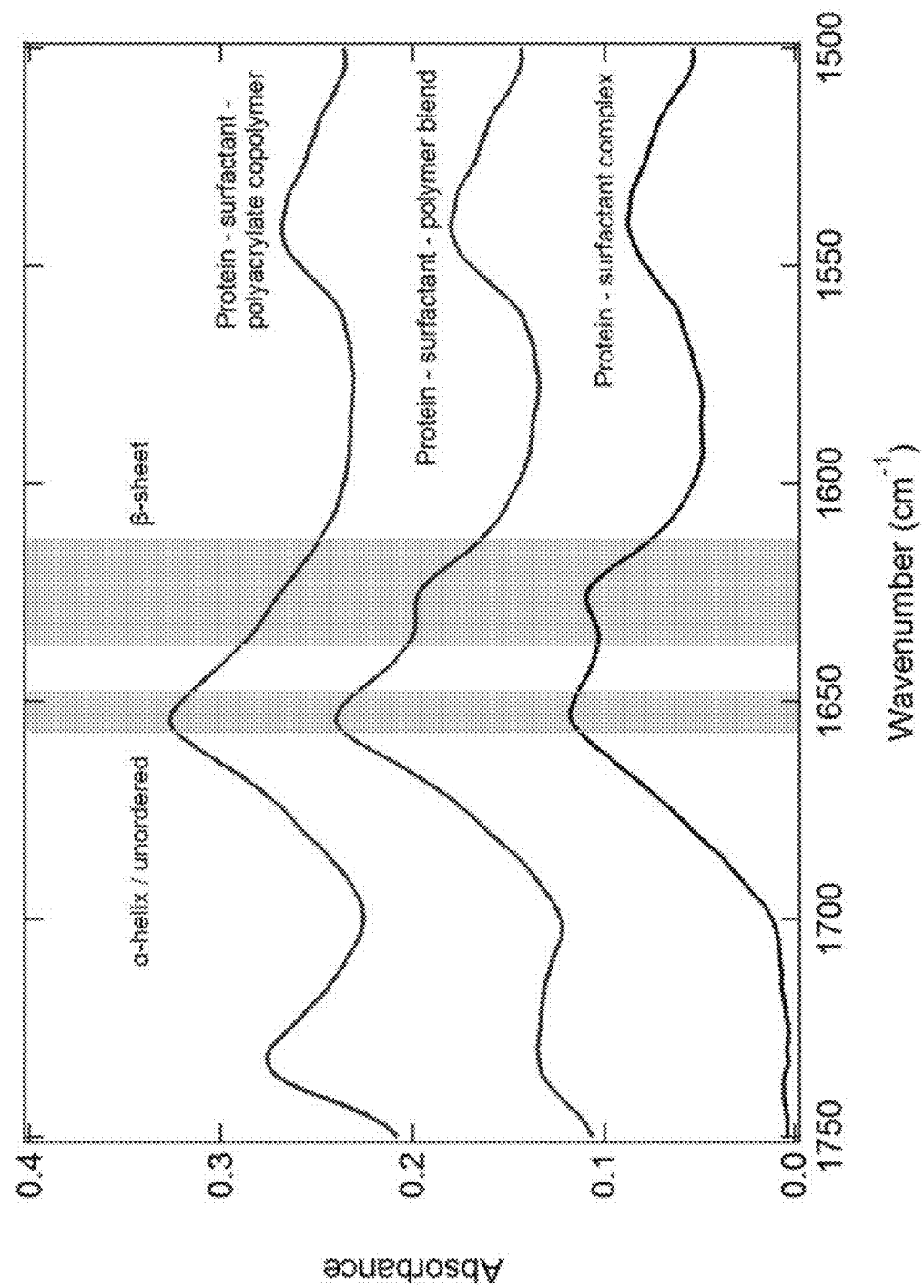
FIG. 15 depicts the protein conformation of an exemplary protein copolymer comprising protein-surfactant-polyacrylate compared to an exemplary protein-surfactant-polymer blend and a protein-surfactant complex.

Protein conformation was measured for the protein-surfactant complex using Fourier transform infrared spectroscopy. The protein conformation was measured after polymerization for the protein-surfactant-polyacrylate copolymer. The amount of β-sheet and turns decreased with the amount of α-helix or unordered regions increased after polymerization (FIG. 15).

D. Morphological Characterization.

I. Small-Angle X-Ray Scattering (SAXS) and Wide-Angle X-Ray Scattering (WAXS)

Figure 16A:
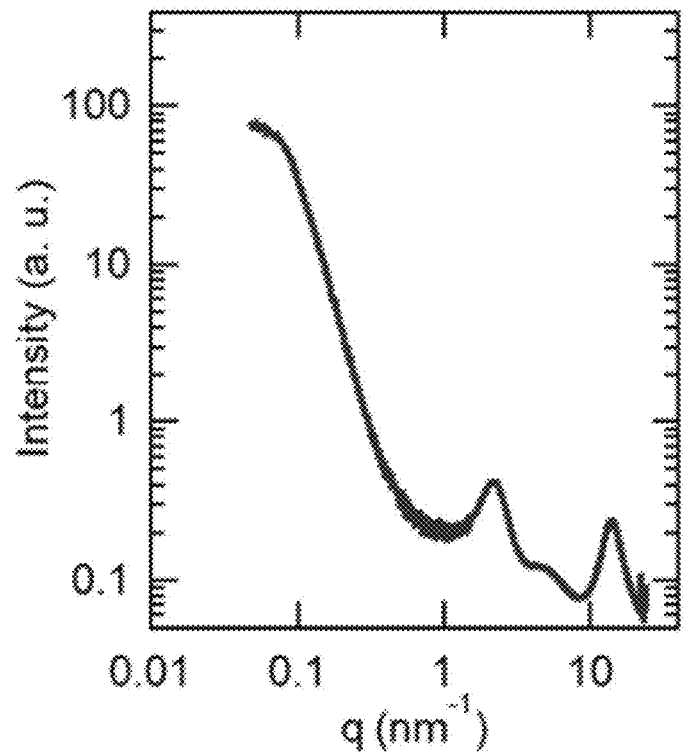
FIG. 16A depicts representative SAXS curve for exemplary protein copolymer comprising protein-surfactant-polyacrylate.
Figure 16B:
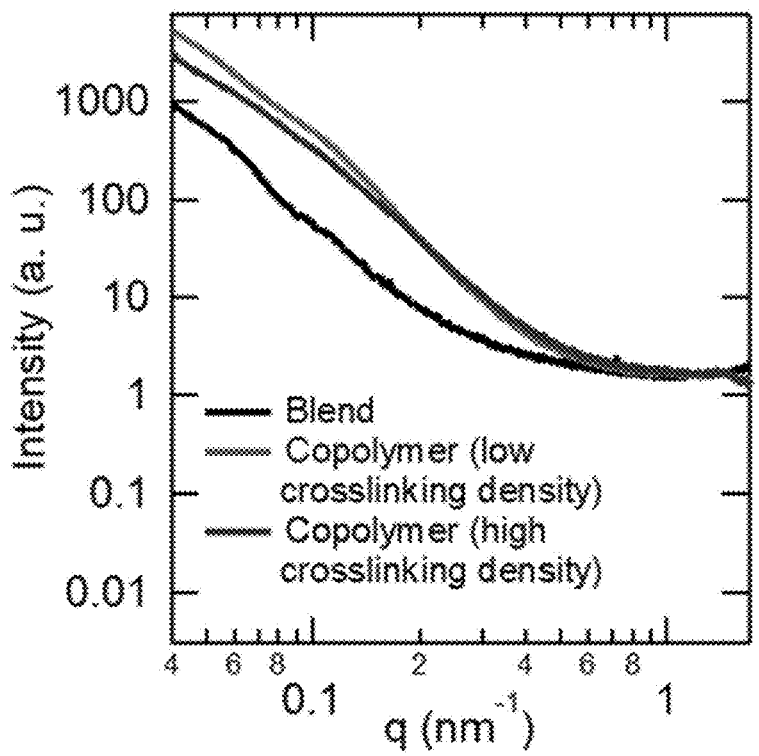
FIG. 16B depicts SAXS curves comparison between a blend and copolymers of various crosslinking densities.
Figure 16C:
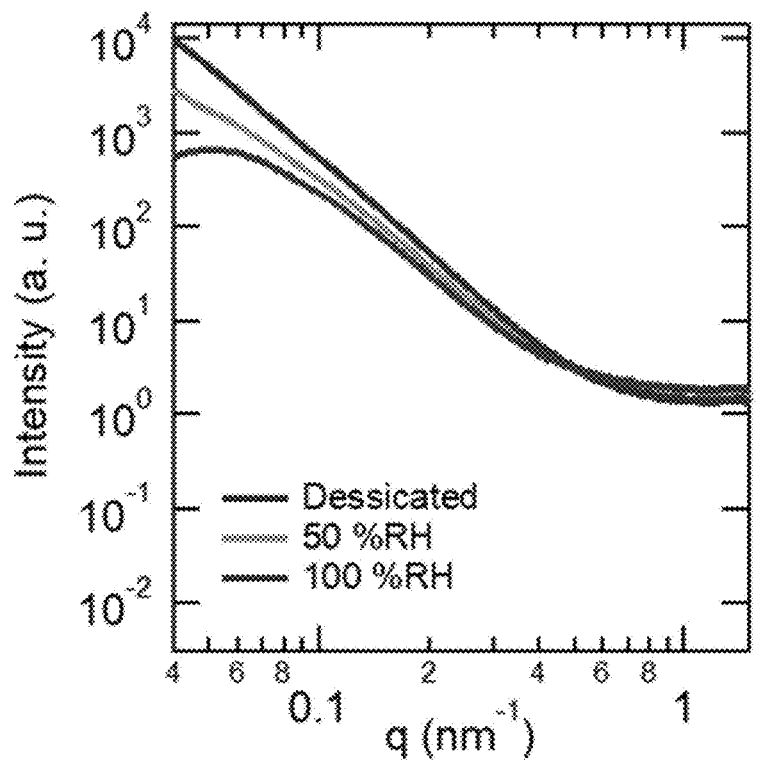
FIG. 16C depicts SAXS curves comparison for exemplary protein copolymer comprising protein-surfactant-polyacrylate conditioned at various relative humidity prior to measurement.
Figure 16D:
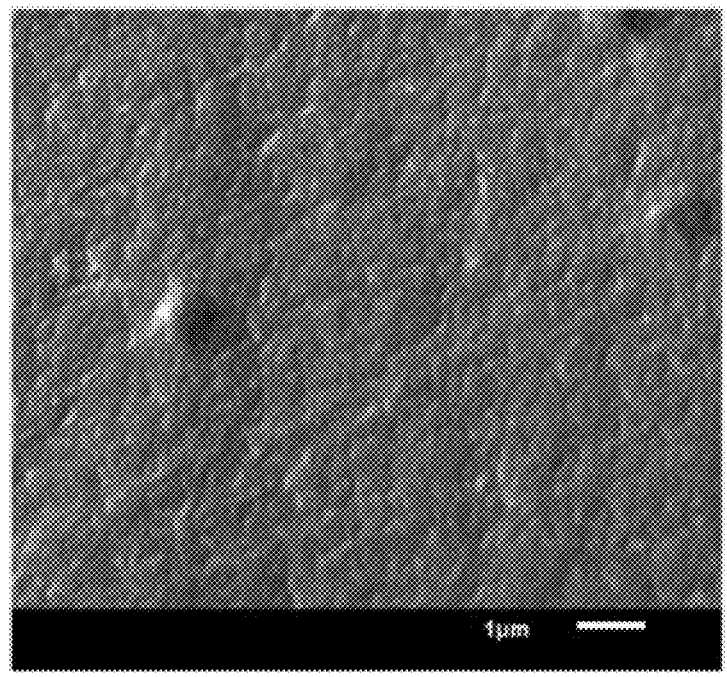
FIG. 16D depicts SEM image of a freeze fractured copolymer surface.

Due to the non-specific nature of protein modification and presence of diverse protein species, the protein-surfactant-polyacrylate copolymers are expected to exhibit microphase separation but not form well-ordered microstructures. The DSC thermogram of the WPI-BAC-poly(n-BA) copolymer (1:1:2 ratio) exhibits features that support the existence of distinct poly(n-BA) and WPI-BAC protein-surfactant transitions at around −52° C. and 57° C. respectively (FIGS. 14A and 14B, top curves). As these two Tg's lie close to that of poly(n-BA) homopolymer and protein-surfactant complex, the hard and soft components are likely microphase separated. The surfactant is likely localized in protein domains, as indicated by the Tg and observations on the immiscibility between surfactant and poly(n-BA) homopolymer. A representative small-angle X-ray scattering (SAXS) intensity curve for a crosslinked copolymer is shown in FIG. 16A. Scattering intensity decreases monotonically with increasing wavenumber, q, with no peaks and features that would be indicative of a characteristic length scale. This is similar to previous observations on copolymerized methacrylated whey protein and hydroxypropyl acrylate (FIG. 8), and indicates a lack of long range order. Similar observations were made across varying material crosslinking densities, temperatures, and equilibration humidity levels (FIGS. 16B and 16C). FIG. 16B depicts comparison of SAXS curves between a blend and copolymers of various crosslinking densities. The blend was prepared with unmodified proteins, while the low and high crosslinking density copolymers were prepared with proteins modified to have roughly 1.2 and 6 methacrylamide groups respectively. FIG. 16C depicts SAXS curves for a crosslinked whey protein isolate-benzalkonium chloride-poly(n-butyl acrylate) conditioned at various relative humidity prior to measurement. Protein:surfactant:co-monomer (second monomer) ratio is 1:1:2, and the proteins are modified to have roughly 6 methacrylamide groups per protein. Scanning electron microscope (SEM) images of a fractured surface of the copolymer depict rough textures and no regular distinct phases (FIG. 16D), which is consistent with observations from SAXS.

Figure 17A:
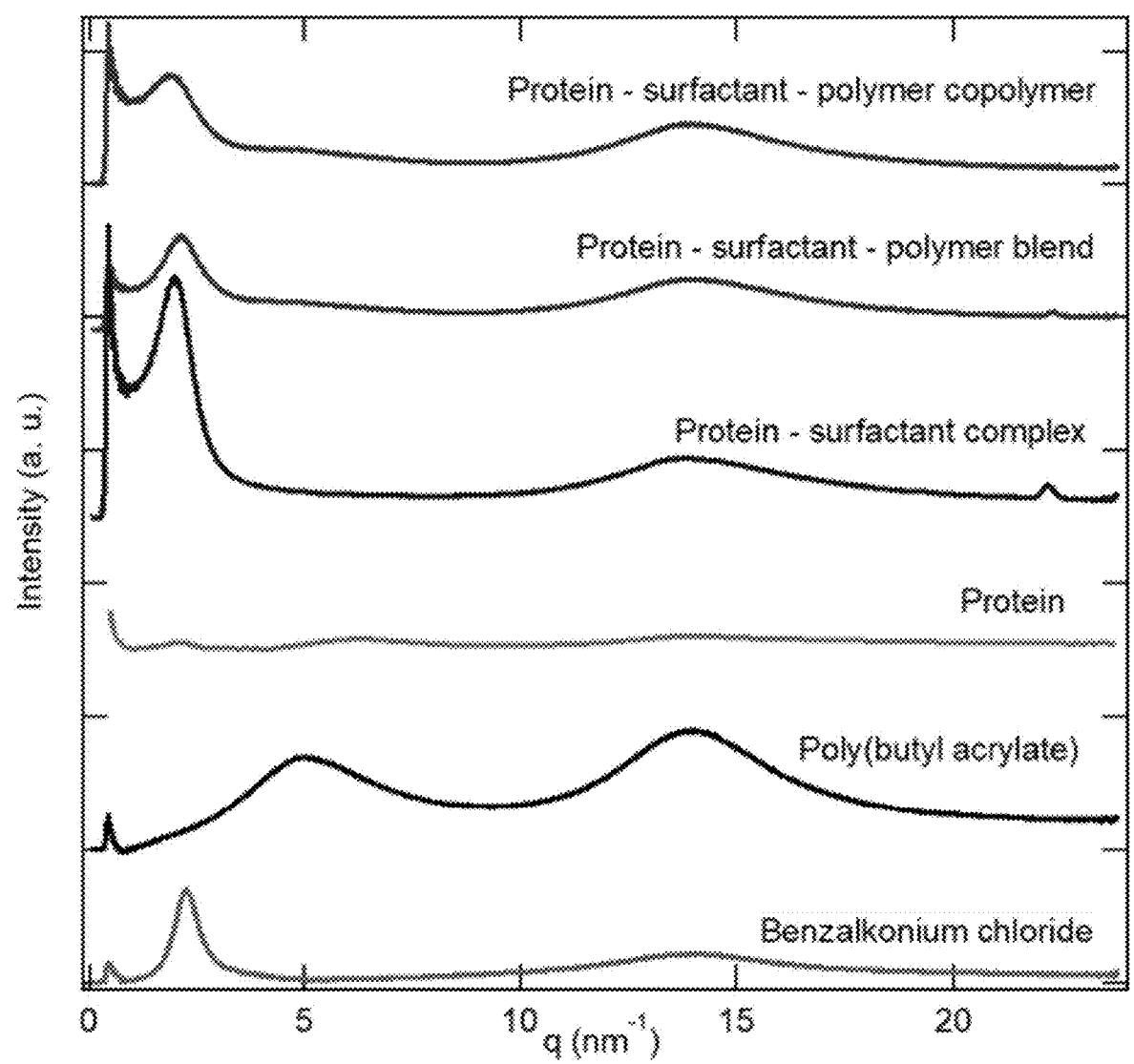
FIG. 17A depicts comparison of WAXS curves for exemplary protein copolymer comprising protein-surfactant-polyacrylate, protein-surfactant-polymer blend, protein-surfactant complex, protein, homopolymer, and surfactant from top to bottom.
Figure 17B:
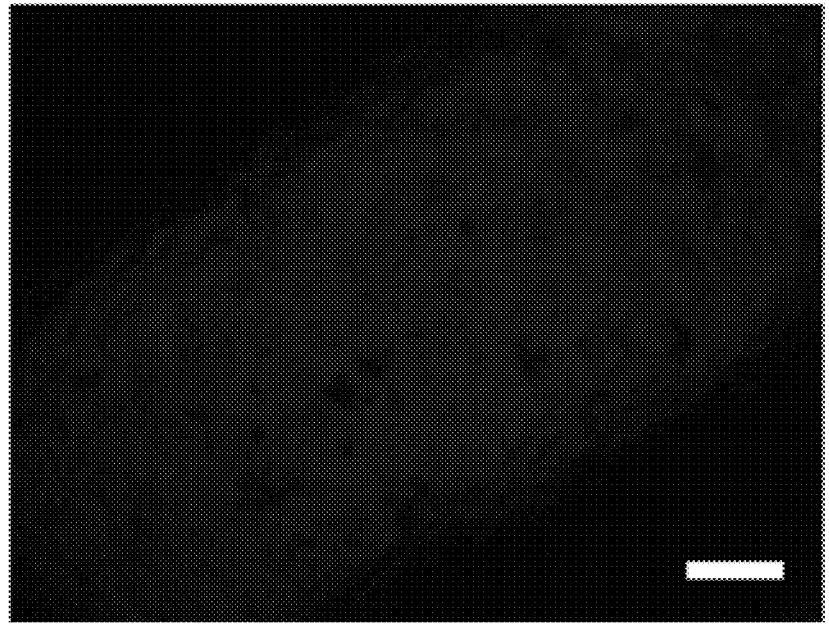
FIG. 17B depicts microscope image under a cross polarizer of exemplary protein-surfactant complex at a mass ratio of 1:1 at 0% strain. Scale bar: 200 μm.
Figure 17C:
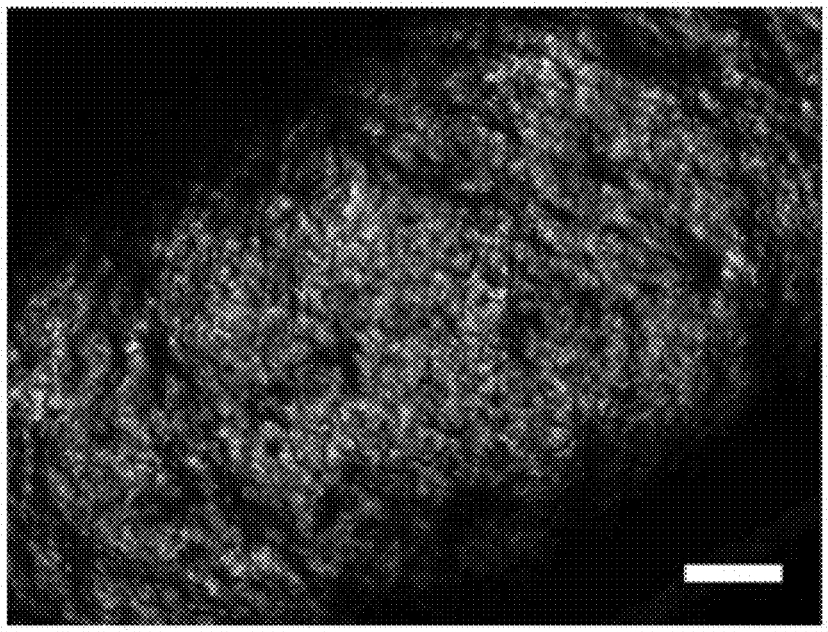
FIG. 17C depicts microscope image under a cross polarizer of exemplary protein-surfactant complex at a mass ratio of 1:1 at 50% strain. Scale bar: 200 μm.
Figure 17D:
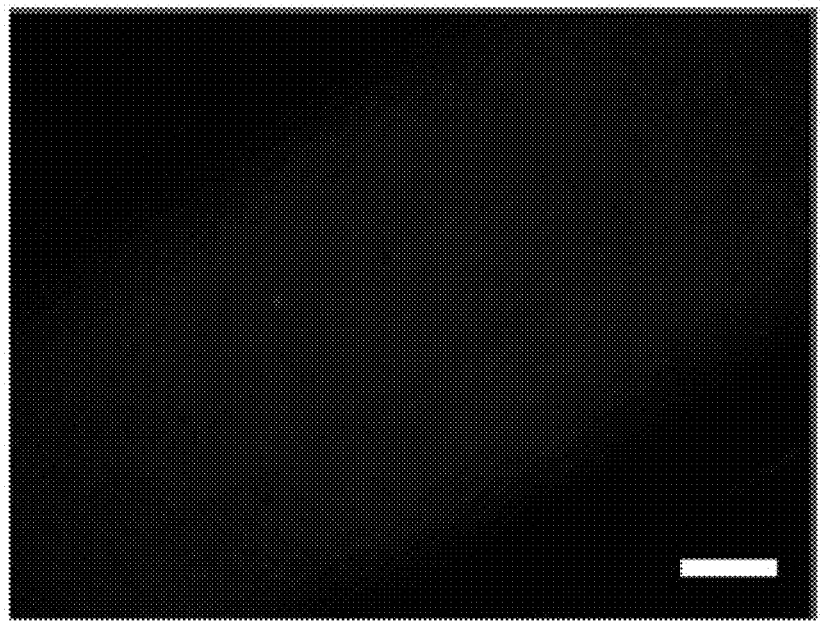
FIG. 17D depicts microscope image under a cross polarizer of exemplary protein copolymer comprising protein-surfactant-polyacrylate at a mass ratio of 1:1:2 at 0% strain. Scale bar: 200 μm.
Figure 17E:
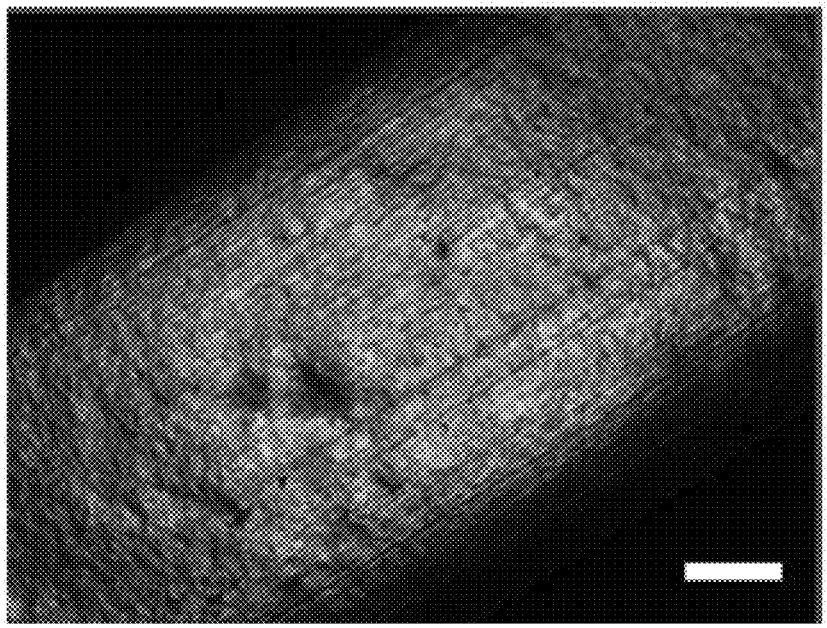
FIG. 17E depicts microscope image under a cross polarizer of exemplary protein copolymer comprising protein-surfactant-polyacrylate at a mass ratio of 1:1:2 at 50% strain. Scale bar: 200 μm.
Figure 18:
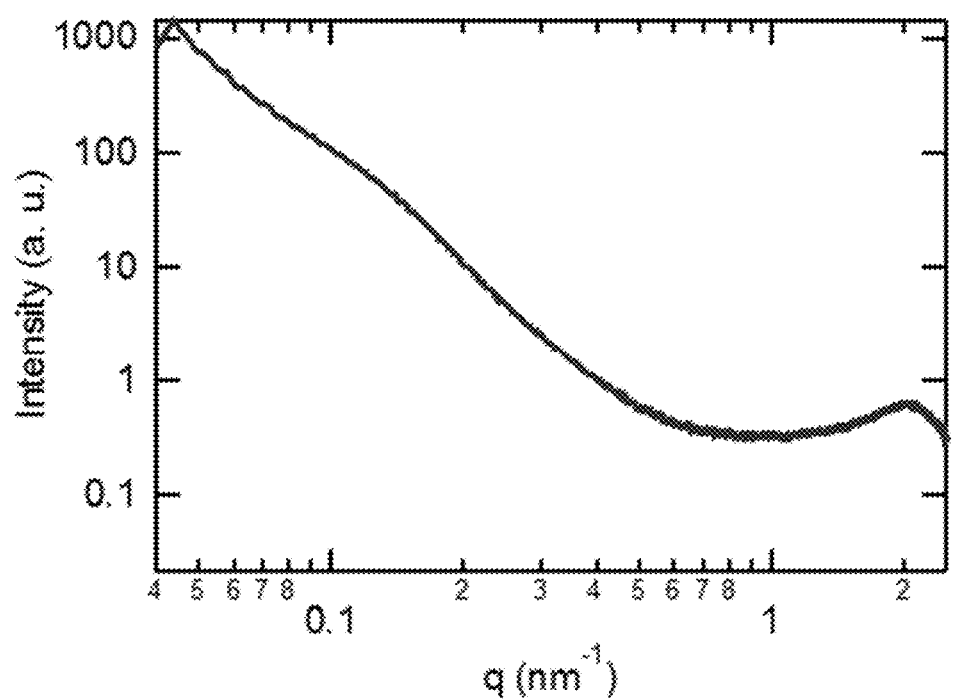
FIG. 18 depicts SAXS curve for exemplary protein-surfactant complex.

Short range ordering in the protein-surfactant complexes and protein-surfactant-polyacrylate blends and copolymers was investigated using wide-angle X-ray scattering (WAXS) in vacuum conditions to understand structure in the absence of water. Broad peaks observed confirm the amorphous nature of all the blends and copolymers. The peak at around 14 $nm^{-1}$ observed in all materials including poly(n-butyl acrylate) homopolymer and benzalkonium chloride correspond to a 0.45 nm spacing, and can be attributed to lateral alkyl tail-tail distances, protein backbone and inter-strand distances. A sharper peak at around 2.3 $nm^{-1}$ (long period of 2.7 nm) is present in all surfactant containing materials. These low wavenumber scattering peaks for the complex, blend, and copolymer were broader and shifted to lower wavenumbers when compared to that of the surfactant (Table 3), suggesting the disruption of surfactant packing upon protein complexation. FIG. 17A depicts comparison of WAXS curves for exemplary protein copolymer comprising protein-surfactant-polyacrylate (WPI-BAC-poly(n-BA) copolymer, 1:1:2 ratio), protein-surfactant-polymer blend (WPI-BAC-poly(n-BA) blend, 1:1:2 ratio), protein-surfactant complex (WPI-BAC, 1:1 ratio), protein (WPI), homopolymer (poly(n-BA)), and surfactant (BAC). The amorphous protein-surfactant complexes and copolymers are isotropic when examined between cross polarizers, but are birefringent upon stretching (FIGS. 17B-17E). This is consistent with the SAXS results (FIG. 18), where the complexes lack molecular ordering when unperturbed. Upon stretching, the complexes can be oriented, which has also been previously observed in plasticized proteins and protein blends[71].

TABLE 4

Comparison of WAXS peak positions for benzalkonium chloride, whey protein-benzalkonium chloride complex, whey protein-benzalkonium chloride-poly(n-butyl acrylate) blend and copolymer.

| Material | Peak Center ($nm^{-1}$) | d-Spacing (nm) | Full Width Half Max (nm) |
| --- | --- | --- | --- |
| Surfactant only | 2.29 | 2.74 | 0.61 |
| Protein-surfactant complex | 1.98 | 3.18 | 0.99 |
| Protein-surfactant-polyacrylate blend | 2.15 | 2.92 | 0.72 |
| Protein-surfactant-polyacrylate copolymer (6 methacrylamide groups per protein) | 2.21 | 2.85 | 0.91 |

Small-angle and wide-angle X-ray scattering (SAXS and WAXS) data were acquired in transmission mode using a Rigaku 002 microfocus X-ray source with Cu Kα radiation (0.154 nm) with a sample-to-detector distance of 109.1 mm. Data was acquired using a DECTRIS Pilatus 300 K hybrid panel array with an exposure time of 5 min for SAXS and 2 min for WAXS. Two-dimensional diffraction images were background-corrected, azimuthally averaged, and plotted as one-dimensional scattering profiles.

Copolymer morphologies were also studied using scanning electron microscopy (SEM). Flat samples were prepared by fracturing in liquid nitrogen, and clamped vertically to observe the fractured surface. Materials were sputter coated with gold, and the microscope images were acquired at a voltage of 15 keV.

II. Attenuated Total Reflection-Infrared Spectroscopy (ATR-FTIR)

Figure 19A:
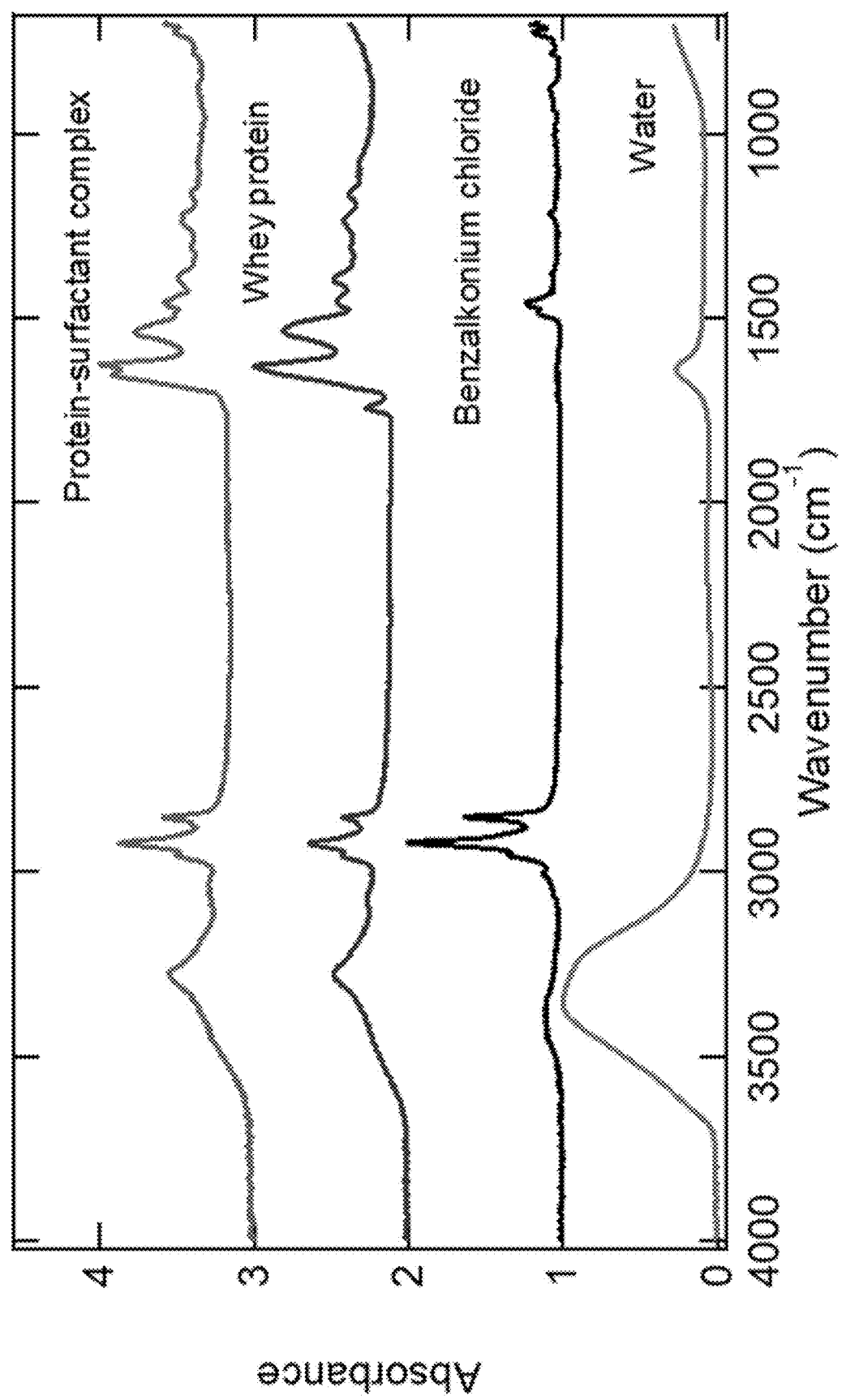
FIG. 19A depicts microscope ATR-FTIR spectra of exemplary protein-surfactant complex, protein, surfactant, and water from top to bottom.
Figure 19B:
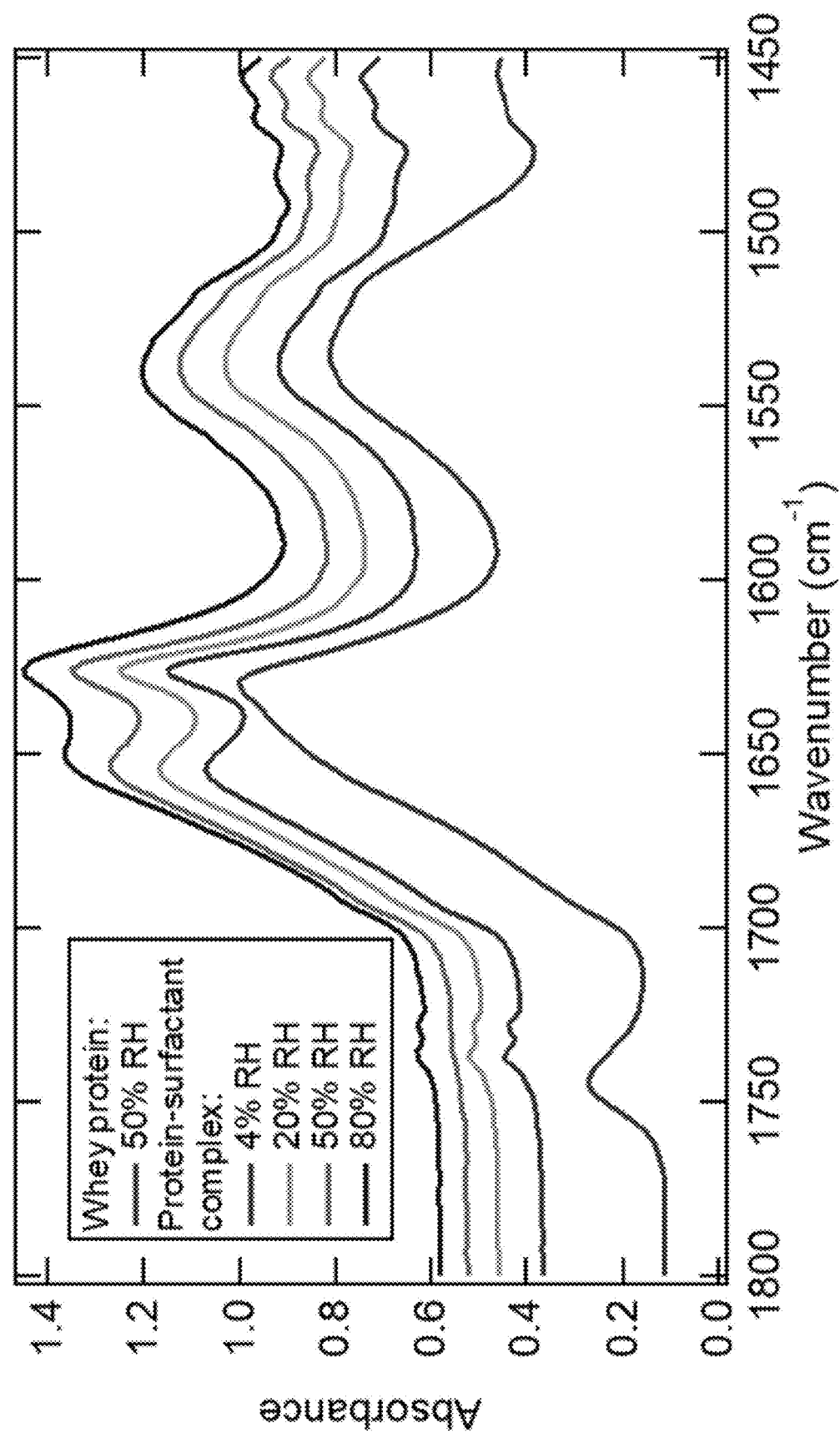
FIG. 19B depicts microscope ATR-FTIR spectra in the amide I and amide II regions of exemplary protein-surfactant complex and protein after incubation at various relative humidity levels.

Structural changes of the protein as a result of surfactant complexation were observed using Attenuated Total Reflection-Fourier Transform Infrared (ATR-FTIR) spectroscopy (FIG. 19A). The intense amide I absorption of proteins (1600-1700 $cm^{-1}$) which originates mainly from C=O stretching with minor contribution from C—N stretching, is known to provide important structural information. Solution cast whey protein has a strong absorption peak at 1630 $cm^{-1}$, consistent with large fractions of β-sheet structures in the protein mixture comprised primarily of β-lactoglobulin (FIG. 19B). Upon complexation and high temperature compression molding with benzalkonium chloride, the amide I band appeared to split into two main components: one at a lower frequency of 1626 $cm^{-1}$ and another at around 1655 $cm^{-1}$. The 1630 $cm^{-1}$ β-structure peak is affected by the strength of hydrogen bond involving the amide carbonyl (C=O), and the lowered frequency suggested the presence of denatured and aggregated proteins with strong intermolecular hydrogen bonds. Relative intensity of the 1655 $cm^{-1}$ band versus the 1626 $cm^{-1}$ band is higher when whey protein was complexed with benzalkonium chloride, indicating a larger presence of random coil or helix structures. These changes may suggest that the process of surfactant blending and compression molding led to the unfolding of proteins, and the formation of denatured protein aggregates with increased intermolecular hydrogen bonding interactions. When the protein-surfactant complex was exposed to high humidity levels (80% relative humidity), a further increase in the higher frequency component relative to the 1626 $cm^{-1}$ band was observed. No major differences were observed in the amide II region (1510-1580 $cm^{-1}$) between the protein and protein-surfactant complexes (FIG. 19B). This region has previously been found to be less sensitive to protein conformation, but is affected by the hydrogen bonding interactions and environment of the N—H group. The similarity between the protein and protein-surfactant complex could therefore be attributed the lack of functional groups that participate in hydrogen bonding in benzalkonium chloride.

Microscope ATR-FTIR data were acquired on a Thermo Fisher Continuum Fourier Transform Infrared Microscope attached to an FTIR6700 bench using a germanium crystal. 64 scans were collected with a resolution of 4 $cm^{-1}$. Samples were conditioned at 23° C. and various levels of relative humidity prior to testing, and measurements were performed at ambient conditions. ATR and atmospheric corrections were applied using the OMNIC software package, and all spectra were min-max normalized. FIG. 19A depicts microscope ATR-FTIR spectra of exemplary protein-surfactant complex (WPI-BAC, 1:1 ratio), protein (WPI), surfactant (BAC), and water from top to bottom. The effects of various relative humidity levels on the amide I and amide II regions for ATR-FTIR spectra of WPI-BAC compared to WPI are show in FIG. 19B.

A method for synthesizing protein-surfactant-polyacrylate thermoset elastomers was demonstrated using whey protein isolate as a model mixture of proteins. Networks made up of protein hard blocks covalently bonded to flexible acrylate polymer chain soft blocks combined with surfactants exhibited desirable performances typically seen in synthetic polymers like polyurethanes. Materials were prepared through the copolymerization of a complex comprising methacrylate groups on proteins and surfactants with acrylate second monomers, where chemical crosslink density was modulated through protein methacrylation levels. An exemplary material comprised a modified whey protein comprising methacrylate groups, an ionic surfactant benzalkonium chloride, and n-butyl acrylate co-monomers (second monomers). Morphological characterizations of the copolymers suggest the formation of microphase separated domains through protein aggregation, the extent of which is influenced by methacrylation level or chemical crosslink density.

A practical and scalable melt polymerization approach to prepare protein copolymers and demonstrated for the first time that surfactants can be used as both plasticizers for proteins and compatiblizers. The use of appropriate surfactants enables mixing of proteins with monomers of wide-ranging polarity and expands the accessible range of material properties for protein-based copolymers. The plasticization capability of surfactants allows the copolymers to be thermoformed and melt polymerized, which is critically enabling for industrial processes such as injection and blow molding. Materials were prepared, for example, by first complexing whey protein with a cationic surfactant benzalkonium chloride. The complexes were shown to be partially miscible with the hydrophobic vinyl monomer n-butyl acrylate in the absence of solvent. Mixtures of a protein, monomer, and surfactant can be thermoformed and cured, while shrinkage issues due to post-processing solvent evaporation are eliminated. Copolymers consisting of a protein-polyacrylate network and surfactant are produced when methacrylamide functionalities are installed onto proteins. As proteins function as macrocrosslinkers, the crosslinking density is modulated by protein modification level. Copolymers in general have lower stiffness but higher elongation-at-break, ultimate tensile strength, and toughness than uncrosslinked blends. The presence of both the stiff protein and flexible polyacrylate domains are crucial for mechanical properties, as individually, these materials are either too brittle or too soft. Copolymers may be microphase separated, as thermal transitions of both the polyacrylate phase and protein-surfactant phase are observed. However, they generally do not have ordered microstructures.

To assess the impact of incorporation of a hydrophobic component into copolymers, a second material was prepared with hydrophilic monomer poly(ethylene glycol) methyl ether acrylate. Moisture absorption of the two types of materials are similar when materials were desiccated, but increases with a larger magnitude for the hydrophilic copolymer at higher humidities. Although n-butyl acrylate is effective at lowering the copolymer's overall moisture absorption, both materials exhibit similar qualitative trends in material softening and have peak toughness at 20-50% relative humidity. Therefore, protein-surfactant complexes represent an important technology for solvent-free processing of protein biomass into hydrophobic polymers, but despite a reduction in water uptake, challenges remain with managing humidity effects on the protein domains.

REFERENCES CITED (1) Qi, H. J.; Boyce, M. C., Stress-strain behavior of thermoplastic polyurethanes. *Mech Mater* 2005, 37 (8), 817-839.
(2) Petrovid, Z. S.; Ferguson, J., Polyurethane elastomers. *Progress in Polymer Science* 1991, 16 (5), 695-836.
(3) Baur, X.; Marek, W.; Ammon, J.; Czuppon, A. B.; Marczynski, B.; Raulfheimsoth, M.; Roemmelt, H.; Fruhmann, G., Respiratory and Other Hazards of Isocyanates. *Int Arch Occ Env Hea* 1994, 66 (3), 141-152.
(4) Figovsky, O.; Shapovalov, L.; Leykin, A.; Birukova, O.; Potashnikova, R., Recent advances in the development of non-isocyanate polyurethanes based on cyclic carbonates. *PUMAGAZINE INT* 2013, 10 (4), 256-263.
(5) Guan, J.; Song, Y.; Lin, Y.; Yin, X.; Zuo, M.; Zhao, Y.; Tao, X.; Zheng, Q., Progress in study of non-isocyanate polyurethane. *Industrial & Engineering Chemistry Research* 2011, 50 (11), 6517-6527.
(6) Wang, Z.; Zhang, X.; Zhang, L. Q.; Tan, T. W.; Fong, H., Nonisocyanate Biobased Poly(ester urethanes) with Tunable Properties Synthesized via an Environment-Friendly Route. *Acs Sustainable Chemistry & Engineering* 2016, 4 (5), 2762-2770.
(7) Ragauskas, A. J.; Williams, C. K.; Davison, B. H.; Britovsek, G.; Cairney, J.; Eckert, C. A.; Frederick, W. J.; Hallett, J. P.; Leak, D. J.; Liotta, C. L., The path forward for biofuels and biomaterials. *science* 2006, 311 (5760), 484-489.
(8) Shen, L.; Worrell, E.; Patel, M., Present and future development in plastics from biomass. *Biofuels, Bioproducts and Biorefining* 2010, 4 (1), 25-40.
(9) Petrović, Z. S., Polyurethanes from vegetable oils. *Polymer Reviews* 2008, 48 (1), 109-155.
(10) Javni, I.; Hong, D. P.; Petrovic, Z. S., Soy-based polyurethanes by nonisocyanate route. *Journal of Applied Polymer Science* 2008, 108 (6), 3867-3875.
(11) Bahr, M.; Mulhaupt, R., Linseed and soybean oil-based polyurethanes prepared via the non-isocyanate route and catalytic carbon dioxide conversion. *Green Chem* 2012, 14 (2), 483-489.
(12) Cinelli, P.; Anguillesi, I.; Lazzeri, A., Green synthesis of flexible polyurethane foams from liquefied lignin. *Eur Polym J* 2013, 49 (6), 1174-1184.
(13) Mulhaupt, R., Green Polymer Chemistry and Bio-based Plastics: Dreams and Reality. *Macromol Chem Phys* 2013, 214 (2), 159-174.
(14) Saito, T.; Perkins, J. H.; Jackson, D. C.; Trammel, N. E.; Hunt, M. A.; Naskar, A. K., Development of lignin-based polyurethane thermoplastics. *Rsc Adv* 2013, 3 (44), 21832-21840.
(15) Skarja, G. A.; Woodhouse, K. A., Structure-property relationships of degradable polyurethane elastomers containing an amino acid-based chain extender. *Journal of Applied Polymer Science* 2000, 75 (12), 1522-1534.
(16) Lee, A.; Deng, Y. L., Green polyurethane from lignin and soybean oil through non-isocyanate reactions. *Eur Polym J* 2015, 63, 67-73.
(17) Mekonnen, T.; Mussone, P.; Bressler, D., Valorization of rendering industry wastes and co-products for industrial chemicals, materials and energy: review. *Crit Rev Biotechnol* 2016, 36 (1), 120-131.
(18) Cuq, B.; Gontard, N.; Guilbert, S., Proteins as agricultural polymers for packaging production. *Cereal Chem* 1998, 75 (1), 1-9.
(19) Jong, L., Characterization of soy protein/styrene-butadiene rubber composites. *Compos Part a-Appl S* 2005, 36 (5), 675-682.
(20) Schmid, M.; Dallmann, K.; Bugnicourt, E.; Cordoni, D.; Wild, F.; Lazzeri, A.; Noller, K., Properties of Whey-Protein-Coated Films and Laminates as Novel Recyclable Food Packaging Materials with Excellent Barrier Properties. *Int J Polym Sci* 2012.
(21) Zhao, R. X.; Torley, P.; Halley, P. J., Emerging biodegradable materials: starch- and protein-based bio-nanocomposites. *J Mater Sci* 2008, 43 (9), 3058-3071.

(22) Poole, A. J.; Church, J. S.; Huson, M. G., Environmentally Sustainable Fibers from Regenerated Protein. *Biomacromolecules* 2009, 10 (1), 1-8.
(23) Kumar, R.; Choudhary, V.; Mishra, S.; Varma, I. K.; Mattiason, B., Adhesives and plastics based on soy protein products. *Ind Crop Prod* 2002, 16 (3), 155-172.
(24) Sothomvit, R.; Olsen, C.; McHugh, T.; Krochta, J., Tensile properties of compression-molded whey protein sheets: determination of molding condition and glycerol-content effects and comparison with solution-cast films. *Journal of Food Engineering* 2007, 78 (3), 855-860.
(25) Galietta, G.; Di Gioia, L.; Guilbert, S.; Cuq, B., Mechanical and thermomechanical properties of films based on whey proteins as affected by plasticizer and crosslinking agents. *Journal of Dairy Science* 1998, 81 (12), 3123-3130.
(26) Hemandez-Izquierdo, V.; Krochta, J., Thermoplastic processing of proteins for film formation—a review. *Journal of food science* 2008, 73 (2), R30-R39.
(27) Silva, N. H. C. S.; Vilela, C.; Marrucho, I. M.; Freire, C. S. R.; Neto, C. P.; Silvestre, A. J. D., Protein-based materials: from sources to innovative sustainable materials for biomedical applications. *Journal of Materials Chemistry B* 2014, 2 (24), 3715-3740.
(28) Patel, R. N., Synthesis of chiral pharmaceutical intermediates by biocatalysis. *Coordin Chem Rev* 2008, 252 (5-7), 659-701.
(29) Russell, A. J.; Berberich, J. A.; Drevon, G. E.; Koepsel, R. R., Biomaterials for mediation of chemical and biological warfare agents. *Annu Rev Biomed Eng* 2003, 5, 1-27.
(30) Rathore, O.; Sogah, D. Y., Nanostructure formation through β-sheet self-assembly in silk-based materials. *Macromolecules* 2001, 34 (5), 1477-1486.
(31) Jin, E. Q.; Reddy, N.; Zhu, * Z. F.; Yang, Y. Q., Graft Polymerization of Native Chicken Feathers for Thermoplastic Applications. *Journal of Agricultural and Food Chemistry* 2011, 59 (5), 1729-1738.
(32) Shi, Z.; Reddy, N.; Hou, X. L.; Yang, Y. Q., Tensile Properties of Thermoplastic Feather Films Grafted with Different Methacrylates. *Acs Sustainable Chemistry & Engineering* 2014, 2 (7), 1849-1856. (33) Kinekawa, Y.-I.; Kitabatake, N., Purification of β-lactoglobulin from whey protein concentrate by pepsin treatment. *Journal of dairy science* 1996, 79 (3), 350-356.
(34) Ritchie, R. O., The conflicts between strength and toughness. *Nature Materials* 2011, 10 (11), 817-822.
(35) Pukanszky, B., Influence of Interface Interaction on the Ultimate Tensile Properties of Polymer Composites. *Composites* 1990, 21 (3), 255-262.
(36) Zhu, J.; Peng, H. Q.; Rodriguez-Macias, F.; Margrave, J. L.; Khabashesku, V. N.; Imam, A. M.; Lozano, K.; Barrera, E. V., Reinforcing epoxy polymer composites through covalent integration of functionalized nanotubes. *Adv Funct Mater* 2004, 14 (7), 643-648.
(37) Kim, Y. A.; Chism, G. W.; Mangino, M. E., Determination of the Beta-Lactoglobulin, Alpha-Lactalbumin and Bovine Serum-Albumin of Whey-Protein Concentrates and Their Relationship to Protein Functionality. *Journal of Food Science* 1987, 52 (1), 124-127.
(38) Mather, B. D.; Viswanathan, K.; Miller, K. M.; Long, T. E., Michael addition reactions in macromolecular design for emerging technologies. *Progress in Polymer Science* 2006, 31 (5), 487-531.
(39) Anker, M.; Stading, M.; Hermansson, A. M., Mechanical properties, water vapor permeability, and moisture contents of beta-lactoglobulin and whey protein films using multivariate analysis. *Journal of Agricultural and Food Chemistry* 1998, 46 (5), 1820-1829.
(40) Langton, M.; Hermansson, A. M., Fine-Stranded and Particulate Gels of Beta-Lactoglobulin and Whey-Protein at Varying Ph. *Food Hydrocolloids* 1992, 5 (6), 523-539.
(41) Diani, J.; Fayolle, B.; Gilormini, P., A review on the Mullins effect. *Eur Polym J* 2009, 45 (3), 601-612.
(42) Lilaonitkul, A.; West, J. C.; Cooper, S. L., Properties of Poly(Tetramethylene Oxide)-Poly(Tetramethylene Terephthalate) Block Polymers. *Journal of Macromolecular Science-Physics* 1976, B 12 (4), 563-597.
(43) Seguela, R.; Prudhomme, J., Effects of Casting Solvents on Mechanical and Structural-Properties of Poly diene-Hydrogenated Polystyrene-Polyisoprene-Polystyrene and Poly styrene-Poly butadiene-Polystyrene Block Copolymers. *Macromolecules* 1978, 11 (5), 1007-1016.
(44) Cantoumet, S.; Desmorat, R.; Besson, J., Mullins effect and cyclic stress softening of filled elastomers by internal sliding and friction thermodynamics model. *Int J Solids Struct* 2009, 46 (11-12), 2255-2264.
(45) Cooper, S. L.; Huh, D. S.; Morris, W. J., Stress-Softening in Crosslinked Block Copolymer Elastomers. *Ind Eng Chem Prod Rd* 1968, 7 (4), 248-&.
(46) Jong, L., Dynamic mechanical properties of soy protein filled elastomers. *J Polym Environ* 2005, 13 (4), 329-338.
(47) Wang, M. J., The role of filler networking in dynamic properties of filled rubber. *Rubber Chem Technol* 1999, 72 (2), 430-448.
(48) Sternstein, S. S.; Zhu, A. J., Reinforcement mechanism of nanofilled polymer melts as elucidated by nonlinear viscoelastic behavior. *Macromolecules* 2002, 35 (19), 7262-7273.
(49) Camberlin, Y.; PAscault, J. P., Quantitative DSC evaluation of phase segregation rate in linear segmented polyurethanes and polyurethaneureas. *Journal of Polymer Science: Polymer Chemistry Edition* 1983, 21 (2), 415-423.
(50) Guan, J.; Porter, D.; Vollrath, F., Thermally Induced Changes in Dynamic Mechanical Properties of Native Silks. *Biomacromolecules* 2013, 14 (3), 930-937.
(51) Ratna, D.; Divekar, S.; Samui, A. B.; Chakraborty, B. C.; Banthia, A. K., Poly(ethylene oxide)/clay nanocomposite: Thermomechanical properties and morphology. *Polymer* 2006, 47 (11), 4068-4074.
(52) Jong, L., Effect of soy protein concentrate in elastomer composites. *Compos Part a-Appl S* 2006, 37 (3), 438-446.
(53) Desper, C. R.; Schneider, N. S.; Jasinski, J. P.; Lin, J. S., Deformation of Microphase Structures in Segmented Polyurethanes. *Macromolecules* 1985, 18 (12), 2755-2761.
(54) Gosal, W. S.; Clark, A. H.; Ross-Murphy, S. B., Fibrillar Ο-lactoglobulin gels: Part 1. Fibril formation and structure. *Biomacromolecules* 2004, 5 (6), 2408-2419.
(55) Bolder, S. G.; Hendrickx, H.; Sagis, L. M. C.; van der Linden, E., Fibril assemblies in aqueous whey protein mixtures. *Journal of Agricultural and Food Chemistry* 2006, 54 (12), 4229-4234.
(56) Schmid, M., Properties of cast films made from different ratios of whey protein isolate, hydrolysed whey protein isolate and glycerol. *Materials* 2013, 6 (8), 3254-3269.
(57) Mekonnen, T.; Mussone, P.; Khalil, H.; Bressler, D., Progress in bio-based plastics and plasticizing modifications. *J Mater Chem A* 2013, 1 (43), 13379-13398.
(58) Gauthier, M. A.; Klok, H.-A., Peptide/protein-polymer conjugates: synthetic strategies and design concepts. *Chemical Communications* 2008, (23), 2591-2611,

(59) Kumiawan, L.; Oiao, G. G.; Zhang, X. Q., Formation of Wheat-Protein-Based Biomaterials through Polymer Grafting and Crosslinking Reactions to Introduce New Functional Properties. *Macromolecular Bioscience* 2009, 9 (1), 93-101, DOI: 10.1002/mabi.200800156

(60) Stenzel, M. H., Bioconjugation Using Thiols: Old Chemistry Rediscovered to Connect Polymers with Nature's Building Blocks. *Acs Macro Lett* 2013, 2 (1), 14-18, DOI: 10.1021/mz3005814

(61) Gao, W. P.; Liu, W. G.; Mackay, J. A.; Zalutsky, M. R.; Toone, E. J.; Chilkoti, A., In situ growth of a stoichiometric PEG-like conjugate at a protein's N-terminus with significantly improved pharmacokinetics. *P Natl Acad Sci USA* 2009,106 (36), 15231-15236, DOI: 10.1073/pnas.0904378106

(62) Huang, A.; Qin, G.; Olsen, B. D., Highly Active Biocatalytic Coatings from Protein-Polymer Diblock Copolymers. *ACS Appl Mater Interfaces* 2015, 7(27), 14660-14669, DOI: 10.1021/acsami.5b01884

(63) Paradkar, V. M.; Dordick, J. S., Mechanism of Extraction of Chymotrypsin into Isooctane at Very-Low Concentrations of Aerosol Ot in the Absence of Reversed Micelles. *Biotechnol Bioeng* 1994, 43 (6), 529-540, DOI 10.1002/bit.260430614.

(64) Gontard, N.; Duchez, C.; Cuq, J. L.; Guilbert, S., Edible Composite Films of Wheat Gluten and Lipids—Water-Vapor Permeability and Other Physical-Properties. *Int J Food Sci Tech* 1994, 29 (1), 39-50

(65) Mo, X.; Sun, X., Plasticization of soy protein polymer by polyol-based plasticizers. *Journal of the American Oil Chemists' Society* 2002, 79 (2), 197-202

(66) Fairley, P.; Monahan, F. J.; German, J. B.; Krochta, J. M., Mechanical properties and water vapor permeability of edible films from whey protein isolate and N-ethylmaleimide or cysteine. *Journal of Agricultural and Food Chemistry* 1996, 44 (12), 3789-3792, DOI 10.1021/jf9601731.

(67) Perriman, A. W.; Mann, S., Liquid Proteins-A New Frontier for Biomolecule-Based Nanoscience. *Acs Nano* 2011, 5 (8), 6085-6091

(68) Liu, K.; Chen, D.; Marcozzi, A.; Zheng, L. F.; Su, J. J.; Pesce, D.; Zajaczkowski, W.; Kolbe, A.; Pisula, W.; Mullen, K.; Clark, N. A.; Herrmann, A., Thermotropic liquid crystals from biomacromolecules. *P Natl Acad Sci USA* 2014, 111 (52), 18596-18600,10.1073/pnas.1421257111.

(69) Bateman, A.; Martin, M. J.; O'Donovan, C.; Magrane, M.; Alpi, E.; Antunes, R.; Bely, B.; Bingley, M.; Bonilla, C.; Britto, R.; Bursteinas, B.; Bye-A-Jee, H.; Cowley, A.; Da Silva, A.; De Giorgi, M.; Dogan, T.; Fazzini, F.; Castro, L. G.; Figueira, L.; Garmiri, P.; Georghiou, G.; Gonzalez, D.; Hatton-Ellis, E.; Li, W. Z.; Liu, W. D.; Lopez, R.; Luo, J.; Lussi, Y.; MacDougall, A.; Nightingale, A.; Palka, B.; Pichler, K.; Poggioli, D.; Pundir, S.; Pureza, L.; Qi, G. Y.; Rosanoff, S.; Saidi, R.; Sawford, T.; Shypitsyna, A.; Speretta, E.; Turner, E.; Tyagi, N.; Volynkin, V.; Wardell, T.; Warner, K.; Watkins, X.; Zaru, R.; Zellner, H.; Xenarios, I.; Bougueleret, L.; Bridge, A.; Poux, S.; Redaschi, N.; Aimo, L.; Argoud-Puy, G.; Auchincloss, A.; Axelsen, K.; Basal, P.; Baratin, D.; Blatter, M. C.; Boeckmann, B.; Bolleman, J.; Boutet, E.; Breuza, L.; Casal-Casas, C.; de Castro, E.; Coudert, E.; Cuche, B.; Doche, M.; Dornevil, D.; Duvaud, S.; Estreicher, A.; Famiglietti, L.; Feuermann, M.; Gasteiger, E.; Gehant, S.; Gerritsen, V.; Gos, A.; Gruaz-Gumowski, N.; Hinz, U.; Hulo, C.; Jungo, F.; Keller, G.; Lara, V.; Lemercier, P.; Lieberherr, D.; Lombardot, T.; Martin, X.; Masson, P.; Morgat, A.; Neto, T.; Nouspikel, N.; Paesano, S.; Pedruzzi, I.; Pilbout, S.; Pozzato, M.; Pruess, M.; Rivoire, C.; Roechert, B.; Schneider, M.; Sigrist, C.; Sonesson, K.; Staehli, S.; Stutz, A.; Sundaram, S.; Tognolli, M.; Verbregue, L.; Veuthey, A. L.; Wu, C. H.; Arighi, C. N.; Arminski, L.; Chen, C. M.; Chen, Y. X.; Garavelli, J. S.; Huang, H. Z.; Laiho, K.; McGarvey, P.; Natale, D. A.; Ross, K.; Vinayaka, C. R.; Wang, Q. H.; Wang, Y. Q.; Yeh, L. S.; Zhang, J.; Consortium, U., UniProt: the universal protein knowledgebase. *Nucleic Acids Res* 2017, 45 (D1), D158-D169,10.1093/nar/gkw1099.

(70) Magdassi, S.; Vinetsky, Y.; Relkin, P., Formation and structural heat-stability of beta-lactoglobulin/surfactant complexes. *Colloid Surface B* 1996, 6 (6), 353-362, Doi 10.1016/0927-7765(96)01266-0.

(71) Barone, J. R.; Dangaran, K.; Schmidt, W. F., Blends of cysteine-containing proteins. *Journal of Agricultural and Food Chemistry* 2006, 54 (15), 5393-5399,10.1021/jf0532381.

INCORPORATION BY REFERENCE

The contents of the articles, patents, and patent applications, and all other documents and electronically available information mentioned or cited herein, are hereby incorporated by reference in their entirety to the same extent as if each individual publication was specifically and individually indicated to be incorporated by reference. Applicants reserve the right to physically incorporate into this application any and all materials and information from any such articles, patents, patent applications, or other physical and electronic documents.

EQUIVALENTS

The invention has been described broadly and generically herein. Those of ordinary skill in the art will readily envision a variety of other means and/or structures for performing the functions and/or obtaining the results and/or one or more of the advantages described herein, and each of such variations and/or modifications is deemed to be within the scope of the present invention. More generally, those skilled in the art will readily appreciate that all parameters, dimensions, materials, and configurations described herein are meant to be exemplary and that the actual parameters, dimensions, materials, and/or configurations will depend upon the specific application or applications for which the teachings of the present invention is/are used. Those skilled in the art will recognize, or be able to ascertain using no more than routine experimentation, many equivalents to the specific embodiments of the invention described herein. It is, therefore, to be understood that the foregoing embodiments are presented by way of example only and that, within the scope of the appended claims and equivalents thereto, the invention may be practiced otherwise than as specifically described and claimed. The present invention is directed to each individual feature, system, article, material, kit, and/or method described herein. In addition, any combination of two or more such features, systems, articles, materials, kits, and/or methods, if such features, systems, articles, materials, kits, and/or methods are not inconsistent, is included within the scope of the present invention. Further, each of the narrower species and subgeneric groupings falling within the generic disclosure also form part of the invention. This includes the generic description of the invention with a proviso or negative limitation removing any subject matter from the genus, regardless of whether or not the excised material is specifically recited herein.

We claim:

1. A copolymer comprising:
   (i) a first monomer, wherein the first monomer is a modified protein comprising a protein and at least one functional group selected from the group consisting of an acrylate, a siloxane, a glycidyl ether, a vinyl group, an epoxy group, and a maleimide group;
   (ii) a surfactant selected from:
      (a) the group consisting of sodium dodecyl sulfate, ammonium dodecyl sulfate, sodium laurate, sodium lauryl ether sulfate, sodium stearate, sodium dodcylbenzenesulfonate, poly(ethylene glycol) 4-nonylphenyl-3-sulfopropyl ether potassium salt, sodium oleate, dioctyl sulfosuccinate benzalkonium chloride, benzethonium chloride, cetylpyridinium chloride, cetyltrimethylammonium bromide, cetryltrimethylammonium chloride, didecyldimethylammonium chloride, dioctadecyldimethylammonium bromide, docosyltrimethylammonium chloride, octenidine dihydrochloride, 1-vinyl-3-dodecylimidazolium bromide, polypropylene glycol (PPG) monomethacrylate phosphate ester, polyoxyethylene alkylphenyl ether ammonium sulfate, polyoxyalkylene alkenyl ether ammonium sulfate, polyethylene glycol octylphenyl ether, lauryldimethylamine oxide, myristamine oxide, sodium lauroamphoacetate, 3-[(3-cholamidopropyl)dimethylammonio]-1-propanesulfonate, cocamidopropyl betaine, cocamidopropyl hydroxysultaine, phosphatidylcholine, phosphatidylethanolamine, phosphatidylinositol, phophatidic acid, dipalmitoylphosphatidylcholine, and soy lecithin, and a mixture of any of them, and
      (b) the group consisting of

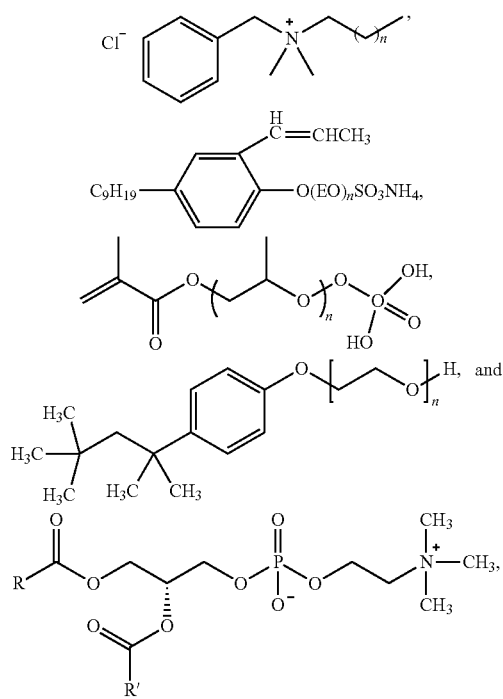

wherein n is an integer from 2 to 22; and R and R' are fatty acid residues; and
   (iii) a second monomer, wherein the second monomer is selected from the group consisting of a monomer comprising an acrylate, a monomer comprising a siloxane, a monomer comprising a glycidyl ether, a monomer comprising a vinyl group, a monomer comprising an epoxy group, and a monomer comprising a maleimide group.

2. The copolymer of claim 1, wherein the first monomer comprises an acrylate.

3. The copolymer of claim 1, wherein the protein is selected from the group consisting of gelatin A, gelatin B, whey protein concentrate, whey protein isolate, β-lactoglobulin, α-lactalbumin, serum albumin, immunoglobin, casein, wheat, silk, soy, zein, algal proteins, fish proteins, lysozyme, synthetic proteins, protein hydrolysates from agricultural crops, recombinant proteins, and a mixture of any of them.

4. The copolymer of claim 1, wherein the modified protein comprises an acrylamide; and the acrylamide is formed from an anhydride and an unmodified protein comprising an amine.

5. The copolymer of claim 1, wherein the modified protein is charged.

6. The copolymer of claim 1, wherein the surfactant is selected from the group consisting of sodium dodecyl sulfate, ammonium dodecyl sulfate, sodium laurate, sodium lauryl ether sulfate, sodium stearate, sodium dodcylbenzenesulfonate, poly(ethylene glycol) 4-nonylphenyl-3-sulfopropyl ether potassium salt, sodium oleate, dioctyl sulfosuccinate, and a mixture of any of them.

7. The copolymer of claim 1, wherein the second monomer is selected from the group consisting of acrylamide, dimethylacrylamide, methyl methacrylate, ethyl acrylate, n-butyl acrylate, glycidyl methacrylate, hydroxyl ethyl methacrylate, ethylene glycol diacrylate, acrylic acid, methacrylic acid, poly(ethylene glycol) methyl ether methacrylate (PEGMA), hydroxypropyl acrylate (HPA), poly(ethylene glycol) diacrylate (PEGDA), 2-vinyl pyridine, 4-vinyl pyridine, p-divinylbenzene, m-divinylbenzene, stylene, styrene, trivinlytrimethylcyclotrisiloxane, tetravinyltetramethylcyclotetrasiloxane, trivinyltrimethylcyclo-trisilazane, tetravinyltetramethylcyclotetrasilazane, and a mixture of any of them.

8. The copolymer of claim 1, wherein the ratio of first monomer to second monomer is about 10,000:1 to about 0.1:1.

9. A method of making a copolymer, comprising the steps of:
   a) combining a first monomer, a surfactant, and a second monomer, thereby forming a mixture;
   b) initiating polymerization of the mixture, thereby forming a copolymer comprising
      (i) a first monomer, wherein the first monomer is a modified protein comprising a protein and at least one functional group selected from the group consisting of an acrylate, a siloxane, a glycidyl ether, a vinyl group, an epoxy group, and a maleimide group;
      (ii) a surfactant selected from:
         (a) the group consisting of sodium dodecyl sulfate, ammonium dodecyl sulfate, sodium laurate, sodium lauryl ether sulfate, sodium stearate, sodium dodcylbenzenesulfonate, poly(ethylene glycol) 4-nonylphenyl-3-sulfopropyl ether potassium salt, sodium oleate, dioctyl sulfosuccinate benzalkonium chloride, benzethonium chloride, cetylpyridinium chloride, cetyltrimethylammonium bromide, cetryltrimethylammonium chloride, didecyldimethylammoniium chloride, dioctadecyldimethylammonium bromide, docosyltrimethylammonium chloride, octenidine dihydrochloride, 1-vinyl-3-dodecylimidazolium bromide, polypropylene glycol (PPG) monomethacrylate phosphate ester, polyoxyethylene alkylphenyl ether ammonium sulfate, polyoxyalkylene alkenyl ether ammonium sulfate, polyethylene glycol octylphenyl ether, lauryldimethylamine oxide, myristamine oxide, sodium lauroamphoacetate, 3-[(3-cholamidopropyl)dimethylammonio]-1-propanesulfonate, cocamidopropyl betaine, cocamidopropyl hydroxysultaine, phosphatidylcholine, phosphatidylethanolamine, phosphatidylinositol, phophatidic acid, dipalmitoylphosphatidylcholine, and soy lecithin, and a mixture of any of them, and (b) the group consisting of

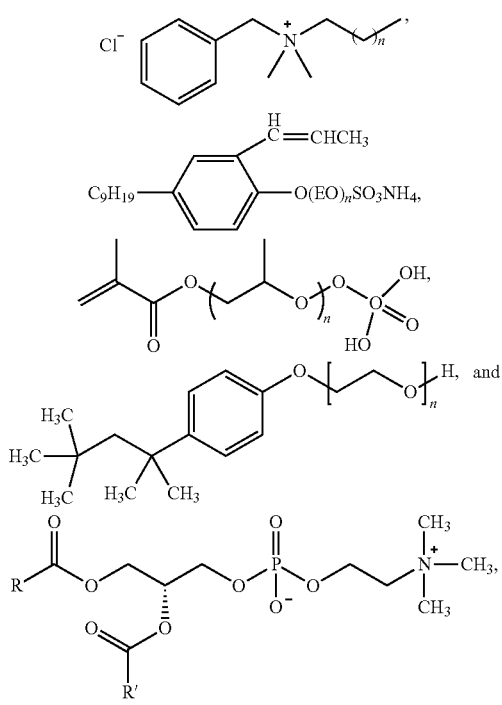

wherein n is an integer from 2 to 22; and R and R' are fatty acid residues; and (iii) a second monomer, wherein the second monomer is selected from the group consisting of a monomer comprising an acrylate, a monomer comprising a siloxane, a monomer comprising a glycidyl ether, a monomer comprising a vinyl group, a monomer comprising an epoxy group, and a monomer comprising a maleimide group.

10. The method of claim 9, wherein the protein is selected from the group consisting of gelatin A, gelatin B, whey protein concentrate, whey protein isolate, β-lactoglobulin, α-lactalbumin, serum albumin, immunoglobin, casein, wheat, silk, soy, zein, algal proteins, fish proteins, lysozyme, synthetic proteins, protein hydrolysates from agricultural crops, recombinant proteins, and a mixture of any of them.

11. The method of claim 9, wherein the surfactant is an ionic surfactant selected from the group consisting of sodium dodecyl sulfate, ammonium dodecyl sulfate, sodium laurate, sodium lauryl ether sulfate, sodium stearate, sodium dodcylbenzenesulfonate, poly(ethylene glycol) 4-nonylphenyl-3-sulfopropyl ether potassium salt, sodium oleate, dioctyl sulfosuccinate, and a mixture of any of them.

12. The method of claim 9, wherein the second monomer is selected from the group consisting of acrylamide, dimethylacrylamide, methyl methacrylate, ethyl acrylate, n-butyl acrylate, glycidyl methacrylate, hydroxyl ethyl methacrylate, ethylene glycol diacrylate, methacrylic acid, poly(ethylene glycol) methyl ether methacrylate (PEGMA), hydroxypropyl acrylate (HPA), poly(ethylene glycol) diacrylate (PEGDA), 2-vinyl pyridine, 4-vinyl pyridine, p-divinylbenzene, m-divinylbenzene, stylene, styrene, trivinlytrimethylcyclotrisiloxane, tetravinyltetramethylcyclotetrasiloxane, trivinyltrimethylcyclotrisilazane, and tetravinyltetramethylcyclotetrasilazane, and a mixture of any of them.

13. The copolymer of claim 1, wherein the surfactant is selected from benzalkonium chloride, benzethonium chloride, cetylpyridinium chloride, cetyltrimethylammonium bromide, cetryltrimethylammonium chloride, didecyldimethylammoniium chloride, dioctadecyldimethylammonium bromide, docosyltrimethylammonium chloride, octenidine dihydrochloride, 1-vinyl-3-dodecylimidazolium bromide, and a mixture of any of them.

14. The copolymer of claim 1, wherein the surfactant is selected from polypropylene glycol (PPG) monomethacrylate phosphate ester, polyoxyethylene alkylphenyl ether ammonium sulfate, polyoxyalkylene alkenyl ether ammonium sulfate, polyethylene glycol octylphenyl ether, lauryldimethylamine oxide, myristamine oxide, sodium lauroamphoacetate, 3-[(3-cholamidopropyl)dimethylammonio]-1-propanesulfonate, cocamidopropyl betaine, cocamidopropyl hydroxysultaine, phosphatidylcholine, phosphatidylethanolamine, phosphatidylinositol, phophatidic acid, dipalmitoylphosphatidylcholine, and soy lecithin, and a mixture of any of them.

15. The copolymer of claim 1, wherein the surfactant is selected from the group consisting of

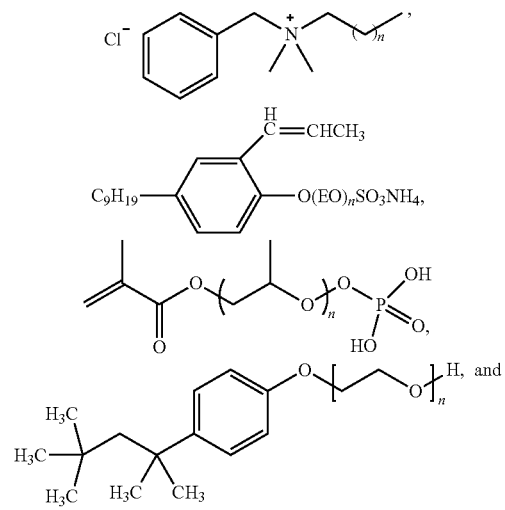

-continued
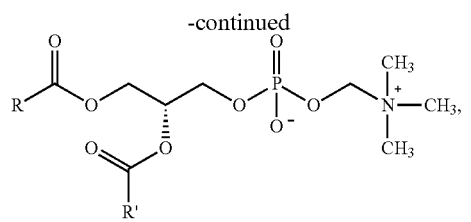
wherein n is an integer from 2 to 22; and R and R' are fatty acid residues.
* * * * *